(12) United States Patent
Sullivan et al.

(10) Patent No.: US 10,570,147 B2
(45) Date of Patent: Feb. 25, 2020

(54) BICYCLIC COMPOUNDS AND METHODS OF USE

(71) Applicant: BioTheryX, Inc., Chappaqua, NY (US)

(72) Inventors: Robert Sullivan, Vista, CA (US); Paul E. Erdman, San Diego, CA (US); Eduardo Torres, San Diego, CA (US); Leah Fung, San Diego, CA (US); Kyle W. H. Chan, San Diego, CA (US); Frank Mercurio, Rancho Santa Fe, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/000,108

(22) Filed: Jun. 5, 2018

(65) Prior Publication Data

US 2018/0354967 A1    Dec. 13, 2018

Related U.S. Application Data

(60) Provisional application No. 62/519,003, filed on Jun. 13, 2017.

(51) Int. Cl.
| | | |
|---|---|---|
| *A61K 31/4015* | (2006.01) | |
| *A61K 31/407* | (2006.01) | |
| *C07D 495/04* | (2006.01) | |
| *A61P 29/00* | (2006.01) | |
| *A61P 37/00* | (2006.01) | |

(52) U.S. Cl.
CPC ............ *C07D 495/04* (2013.01); *A61P 29/00* (2018.01); *A61P 37/00* (2018.01)

(58) Field of Classification Search
CPC . A61K 31/4015; A61K 31/407; C07D 495/04

USPC ...... 514/412, 443; 548/453, 513; 549/50, 54
See application file for complete search history.

(56) References Cited

FOREIGN PATENT DOCUMENTS

| CA | 2761845 A1 * | 11/2010 | ........... C07D 495/04 |
|---|---|---|---|
| EP | 1 964 842 | 9/2008 | |
| EP | 2 083 011 | 7/2009 | |
| EP | 2 431 371 | 3/2012 | |

OTHER PUBLICATIONS

Carey, 1992, 8.15 Sulfonate esters as substrates in nucleophilic substitution reactions, in Organic Chemistry Second Edition, McGraw-Hill, Inc., New York , pp. 328-331.
Greene et al., eds., Protective Groups in Organic Synthesis; John Wiley & Sons, Inc., New York, 1999.
McMurray, 2000, Organic Chemistry Fifth Edition, Brooks/Cole, Pacific Grove, CA, pp. 398, 408.
McOmie ed., Protective Groups in Organic Chemistry, Plenum Press, London and New York, 1973.
Streitwieser et al., 1981, 8.10 Leaving Groups, in Introduction to Organic Chemistry Second Edition, Macmillan Publishing Co., Inc., New York, pp. 169-171.
International Search Report and Written Opinion dated Aug. 21, 2018 in application No. PCT/US2018/036276.

* cited by examiner

*Primary Examiner* — Matthew P Coughlin
*Assistant Examiner* — Sagar Patel
(74) *Attorney, Agent, or Firm* — Knobbe, Martens, Olson & Bear, LLP

(57) ABSTRACT

The present invention provides compounds that modulate protein function, specifically phosphodiesterase 4 (PDE4). The invention provides methods of treating, ameliorating, and/or preventing diseases, disorders, and conditions associated with PDE4. Compositions, including in combination with other inflammatory mediators, are also provided.

30 Claims, No Drawings

BICYCLIC COMPOUNDS AND METHODS OF USE

BACKGROUND OF THE INVENTION

Field of the Invention

Compounds, methods of making such compounds, pharmaceutical compositions and medicaments comprising such compounds, and methods of using such compounds to treat, prevent or diagnose diseases, disorders, or conditions associated with phosphodiesterase 4 (PDE4) malfunction are provided.

Description of the Related Technology

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

For example, phosphodiesterase 4 (PDE4) is involved in the cytokine production of inflammatory cells, angiogenesis, and the functional properties of other cell types such as keratinocytes, in part, through degradation of cyclic adenosine monophosphate (cAMP). cAMP is an important second messenger that regulates inflammatory responses. Accordingly, inhibitors of PDE4 may block the synthesis of several pro-inflammatory cytokines and chemokines, such as tumor necrosis factor alpha, interleukin 23, CXCL9, and CXCL10 in multiple cell types, and may interfere with the production of leukotriene B4, inducible nitric oxide synthase, and matrix metalloproteinases. This interference reduces certain inflammatory processes, such as dendritic cell infiltration, epidermal skin thickening, and joint destruction, for example in psoriasis and other inflammatory and/or autoimmune diseases such as arthritis, ankylosing spondylitis, osteoarthritis, rheumatoid arthritis, Behcet's disease, inflammatory bowel diseases (e.g., Crohn's disease and ulcerative colitis), psoriasis, atopic dermatitis, and contact dermatitis.

Psoriasis is an autoimmune skin disease caused by pro-inflammatory cytokines, interferon gamma (IFN-γ) and TNF-α. The psoriatic immune response involves monocytes, dendritic cells, neutrophils and T cells, which all contribute to aberrant keratinocyte proliferation. PDE4 inhibition may reduce production of multiple mediators including TNF-α, IFN-γ, CXCL9 (monokine induced by IFN-γ, or MIG), CXCL10 (IFN-γ-induced protein of 10 kDa, or IP-10), IL-2, IL-12, IL-23, macrophage inflammatory protein-1-alpha (MIP-1α), monocyte chemoattractant protein-1 and granulocyte macrophage-colony stimulating factor (GM-CSF) from PBMCs. Thus, there is a need for small molecule PDE4 inhibitors.

SUMMARY OF THE INVENTION

The compounds disclosed in the present application have been discovered to exert surprising and unexpected biological effects. In particular, the compounds disclosed in the present application may reduce inflammation, cellular cAMP levels, and inhibit PDE4.

Some embodiments provide a compound of Formula (I), Formula (II), or a pharmaceutically acceptable salt of any of the foregoing,

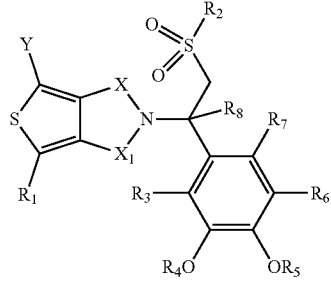

Formula (I)

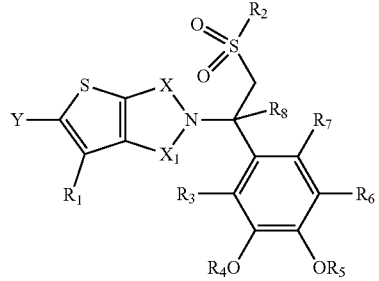

Formula (II)

In some embodiments, X and $X_1$ are each independently $CH_2$, C=O, SO, $SO_2$, or $CH_2CO$.

In some embodiments, Y is H, deuterium, halogen, or an optionally substituted $C_1$-$C_6$ alkyl.

In some embodiments, $R_1$ is H, deuterium, hydroxy, halogen, nitro, cyano, optionally substituted $C_1$-$C_6$ alkoxy, —$NH_2$, —$NHR_{1A}$, —$NR_{1A}R_{1B}$, —$NHC(O)R_{1C}$, —$NR_{1A}C(O)R_{1C}$, —$NHSO_2R_{1C}$, —$NR_{1A}SO_2R_{1C}$, —$N[C(O)R_{1A}][C(O)R_{1C}]$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl.

In some embodiments, $R_{1A}$, $R_{1B}$, and $R_{1C}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl.

In some embodiments, $R_2$ is hydroxy, —$NH_2$, —$NHR_{1A}$, —$NR_{1A}R_{1B}$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl.

In some embodiments, $R_3$, $R_6$, and $R_7$ are independently selected from a hydrogen, a deuterium, a halogen, an optionally substituted $C_1$-$C_6$ alkyl, an optionally substituted $C_1$-$C_6$ alkoxy, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl.

In some embodiments, $R_4$ and $R_5$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl.

In some embodiments, $R_4$ and $R_5$, together with the atoms to which they are attached, form an optionally substituted 5 or 6 membered heterocyclyl.

In some embodiments, $R_8$ is hydrogen or deuterium. In some embodiments, $R_8$ is hydrogen. In other embodiments, $R_8$ is deuterium.

In some embodiments, when $R_2$ is an optionally substituted $C_1$-$C_6$ alkyl, at least one of $R_4$ and $R_5$ is an optionally substituted $C_3$-$C_6$ cycloalkyl, an optionally substituted 3 to 10 membered heterocyclyl, an optionally substituted $C_6$-$C_{10}$ aryl, an optionally substituted 5 to 10 membered heteroaryl, or $R_4$ and $R_5$, together with the atoms to which they are attached, form an optionally substituted 5 or 6 membered heterocyclyl. In some embodiments, when $R_2$ is an optionally substituted $C_1$-$C_4$ alkyl or $NH(C_1$-$C_6$ alkyl), at least one of $R_4$ and $R_5$ is an optionally substituted cyclopropyl. In some embodiments, when $R_4$ and $R_5$ are each independently an optionally substituted $C_1$-$C_6$ alkyl, $R_2$ is an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments, $R_2$, $R_4$, and $R_5$ are not all an optionally substituted $C_1$-$C_6$ alkyl.

In some embodiments, $R_2$ is hydroxy, —$NH_2$, —$NHR_{1A}$, or —$NR_{1A}R_{1B}$, and $R_4$ and $R_5$ are each independently an optionally substituted $C_1$-$C_6$ alkyl, or $R_4$ and $R_5$, together with the atoms to which they are attached, form an optionally substituted 5 or 6 membered heterocyclyl.

In some embodiments, when a $C_1$-$C_6$ alkyl, a $C_1$-$C_6$ alkoxy, a $C_3$-$C_6$ cycloalkyl, a $C_6$-$C_{10}$ aryl, a 3 to 10 membered heterocyclyl, or a 5 to 10 membered heteroaryl is substituted, the substituted substituents are independently selected from a deuterium, an oxo, a halogen, cyano, a nitro, an optionally substituted $C_1$-$C_6$ alkyl, an optionally substituted $C_1$-$C_6$ haloalkyl, an optionally substituted $C_1$-$C_6$ alkoxy, an optionally substituted $C_3$-$C_6$ cycloalkyl, an optionally substituted $C_6$-$C_{10}$ aryl, an optionally substituted 3 to 10 membered heterocyclyl, an optionally substituted 5 to 10 membered heteroaryl, —$C(O)R_A$, —$C(O)OR_A$, —$C(O)NR_BR_C$, —$OR_A$, —$OC(O)R_A$, —$OC(O)NR_BR_C$, —$OS(O)R_A$, —$OS(O)_2R_A$, —$OS(O)NR_BR_C$, —$OS(O)_2NR_BR_C$, —$NR_BR_C$, —$NR_AC(O)R_A$, —$NR_AC(O)OR_A$, —$NR_AC(O)NR_BR_C$, —$NR_AS(O)R_A$, —$NR_AS(O)_2R_A$, —$NR_AS(O)NR_BR_C$, —$NR_AS(O)_2NR_BR_C$, —$SR_A$, —$S(O)R_A$, —$S(O)_2R_A$, —$S(O)NR_BR_C$, and —$S(O)_2NR_BR_C$.

In some embodiments, each $R_A$, $R_B$, and $R_C$ are independently selected from a hydrogen, an unsubstituted $C_1$-$C_6$ alkyl, an unsubstituted $C_2$-$C_6$ alkenyl, an unsubstituted $C_3$-$C_6$ cycloalkyl, an unsubstituted 3 to 10 membered heterocyclyl, an unsubstituted $C_6$-$C_{10}$ aryl, and an unsubstituted 5 to 10 membered heteroaryl.

In some embodiments, $R_B$ and $R_C$, together with the nitrogen atom to which they are attached, form an optionally substituted 3 to 10 membered heterocyclyl.

In some embodiments, Y is H. In some embodiments, Y is deuterium. In some embodiments, Y is halogen. In some embodiments, Y is an optionally substituted $C_1$-$C_6$ alkyl.

In some embodiments, one of X and $X_1$ is $CH_2$ and the other is C=O. In some embodiments, X and $X_1$ are each $CH_2$. In some embodiments, X and $X_1$ are each C=O. In some embodiments, one of X and $X_1$ is $CH_2$ and the other is SO. In some embodiments, one of X and $X_1$ is $CH_2$ and the other is $SO_2$. In some embodiments, one of X and $X_1$ is $CH_2$ and the other is $CH_2CO$. In some embodiments, one of X and $X_1$ is C=O and the other one of X and $X_1$ is SO. In some embodiments, one of X and $X_1$ is C=O and the other one of X and $X_1$ is $SO_2$. In some embodiments, one of X and $X_1$ is C=O and the other is $CH_2CO$.

In some embodiments, $R_1$ is —$NHR_{1A}$, —$NR_{1A}R_{1B}$, —$NHC(O)R_{1C}$ or —$NR_{1A}C(O)R_{1C}$. In some embodiments, $R_1$ is —$N[C(O)R_{1A}][C(O)R_{1C}]$. In some embodiments, $R_1$ is —$NHC(O)R_{1C}$. In some embodiments, $R_{1A}$, $R_{1B}$, and $R_{1C}$ are independently an optionally substituted $C_1$-$C_6$ alkyl or an optionally substituted $C_3$-$C_6$ cycloalkyl. In some embodiments, $R_{1C}$ is an optionally substituted $C_1$-$C_6$ alkyl. In some embodiments, $R_{1C}$ is an unsubstituted $C_1$-$C_6$ alkyl.

In some embodiments, $R_3$, $R_6$, and $R_7$ are independently selected from a hydrogen, a halogen, and an optionally substituted $C_1$-$C_6$ alkyl. In some embodiments, $R_3$, $R_6$, and $R_7$ are each hydrogen.

In some embodiments, $R_2$ is an optionally substituted $C_1$-$C_6$ alkyl and one of $R_4$ and $R_5$ is an optionally substituted $C_1$-$C_6$ alkyl and the other is an optionally substituted $C_3$-$C_6$ cycloalkyl or an optionally substituted 3 to 10 membered heterocyclyl.

In some embodiments, $R_2$ is an unsubstituted $C_1$-$C_6$ alkyl and one of $R_4$ and $R_5$ is an unsubstituted $C_1$-$C_6$ alkyl and the other is an optionally substituted $C_3$-$C_6$ cycloalkyl or an optionally substituted 3 to 10 membered heterocyclyl.

In some embodiments, $R_2$ is an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl, and $R_4$ and $R_5$ are independently an optionally substituted $C_1$-$C_6$ alkyl.

In some embodiments, $R_2$ is an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl, and $R_4$ and $R_5$ are independently unsubstituted $C_1$-$C_6$ alkyl.

In some embodiments, $R_2$ is hydroxy, —$NH_2$, —$NHR_{1A}$, or —$NR_{1A}R_{1B}$, and $R_{1A}$ and $R_{1B}$ are each independently an optionally substituted $C_1$-$C_6$ alkyl or an optionally substituted $C_6$-$C_{10}$ aryl.

In some embodiments, $R_4$ and $R_5$, together with the atoms to which they are attached, form an optionally substituted 5 or 6 membered heterocyclyl.

In some embodiments, $R_4$ and $R_5$, together with the atoms to which they are attached, form an unsubstituted 5 or 6 membered heterocyclyl.

In some embodiments, $R_4$ and $R_5$, together with the atoms to which they are attached, form an unsubstituted 5 membered heterocyclyl.

In some embodiments, $R_4$ and $R_5$, together with the atoms to which they are attached, form an unsubstituted 6 membered heterocyclyl.

In some embodiments, the compound Formula (I) or the compound of Formula (II) is selected from:

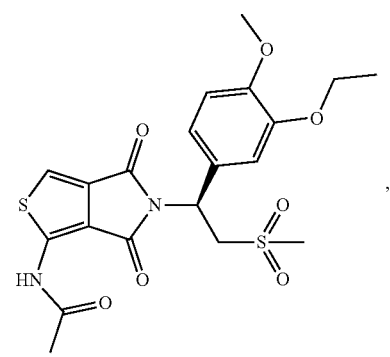,
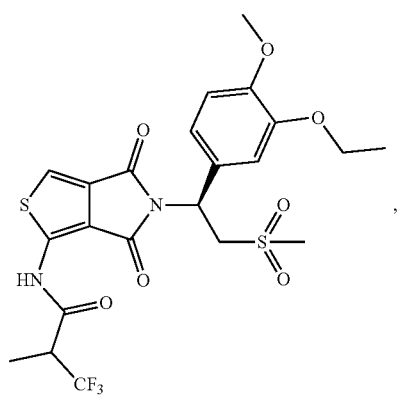,
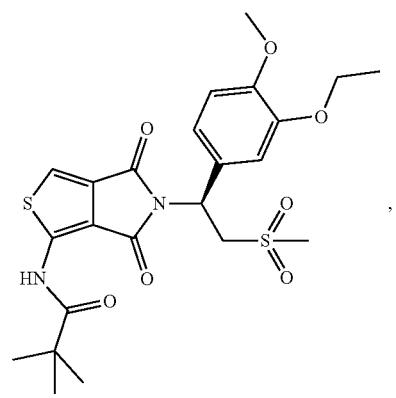,
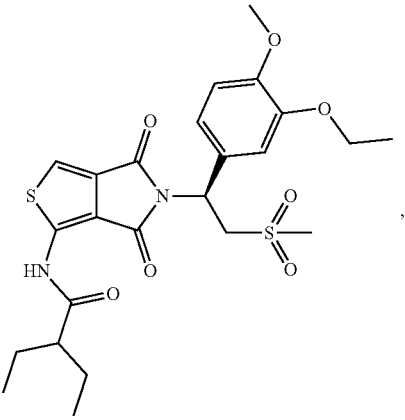,
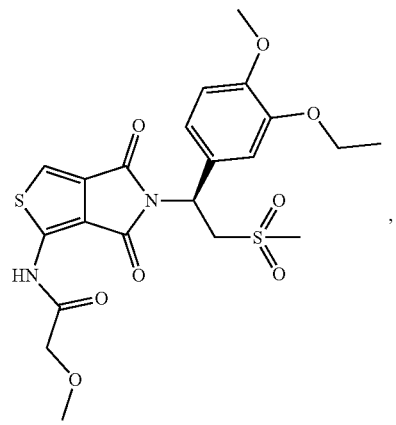,
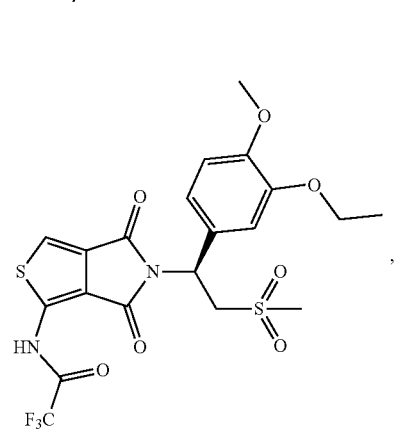,
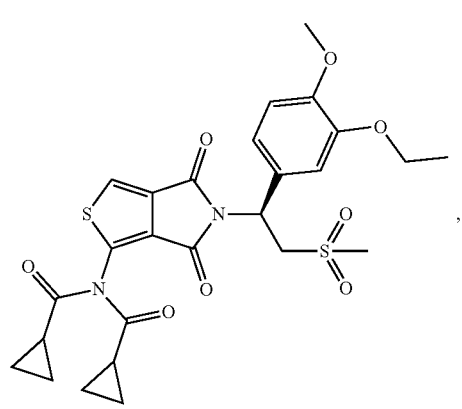,
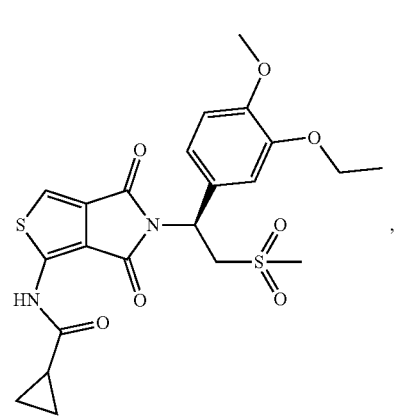, -continued -continued

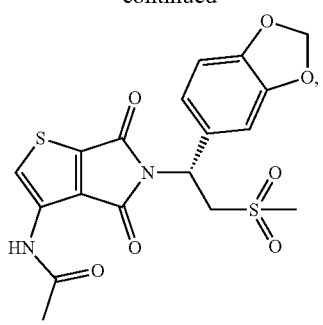
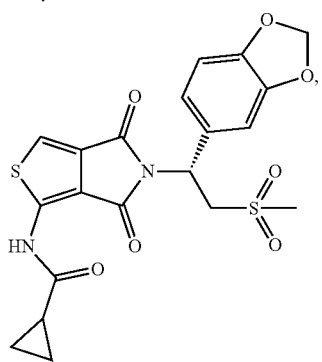
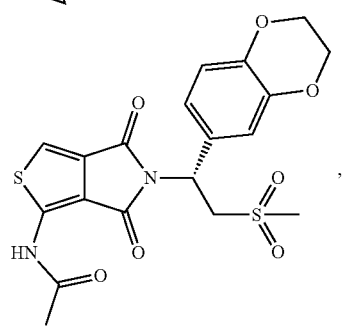
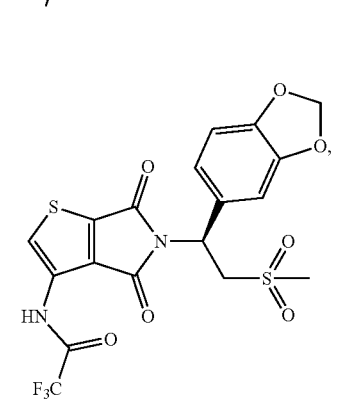
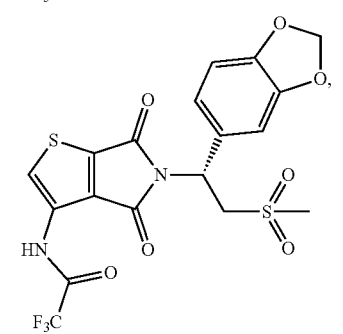
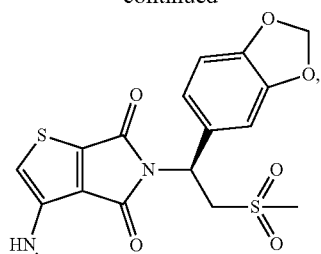
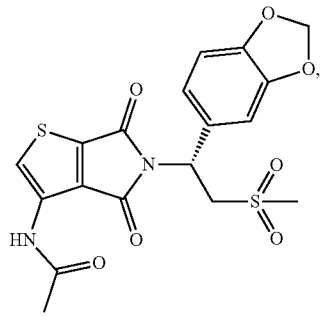
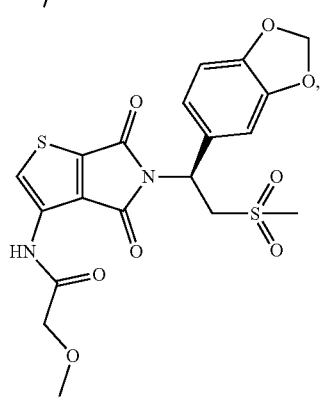
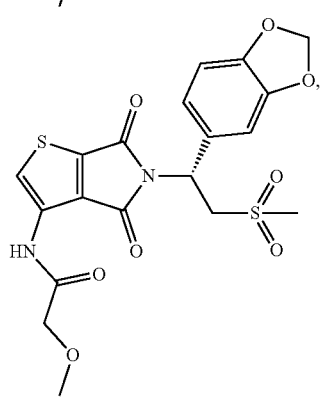
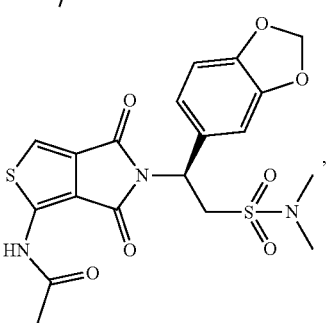

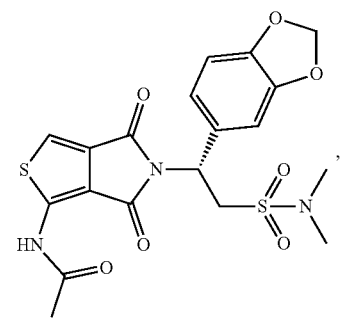

,

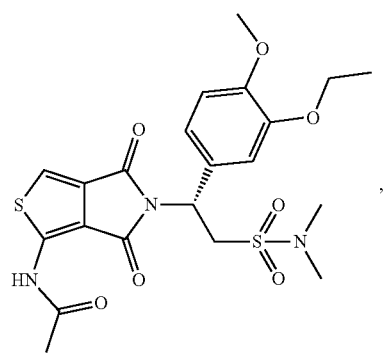

,

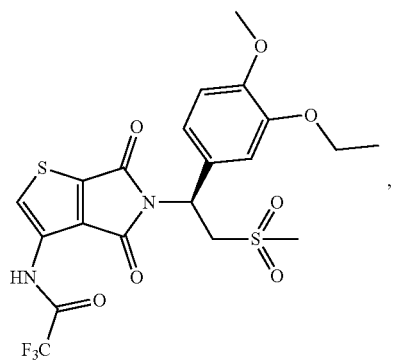

,

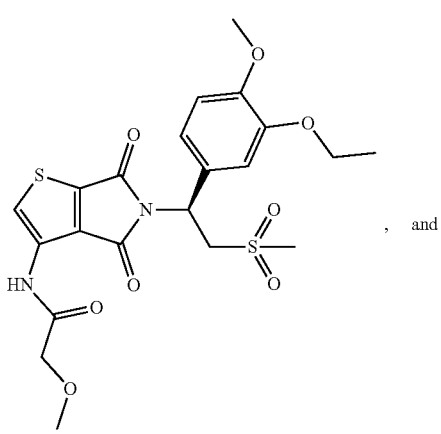

, and

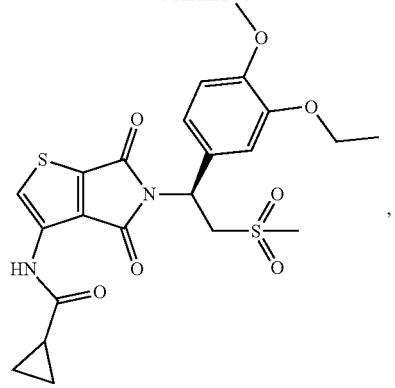

or a pharmaceutically acceptable salt of any of the foregoing.

In some embodiments, the compound is a pharmaceutically acceptable salt.

Some embodiments provide a pharmaceutical composition comprising a compound of any of Formula (I), Formula (II), or a pharmaceutically acceptable salt of any of the foregoing, and at least one pharmaceutically acceptable carrier.

In some embodiments, the composition is formulated for oral, parenteral, topical, ophthalmic, inhalation, nasal, or intravenous administration. In some embodiments, the composition is formulated as a tablet or capsule.

In some embodiments, the pharmaceutical composition further comprises a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is anti-inflammatory agent or an immunosuppressive agent.

Some embodiments provide a method of treating, ameliorating, or preventing a disease, disorder, or condition associated with TNF-α, INF-γ, IL-2, IL-17, IL-23, or a combination thereof, comprising administering a therapeutically effective amount of a compound of any one of Formula (I), Formula (II), or a pharmaceutically acceptable salt of any of the foregoing, or a composition comprising any one of Formula (I) or Formula (II) to a subject in need thereof.

In some embodiments, the disease, disorder, or condition is selected from the group consisting of arthritis, ankylosing spondylitis, osteoarthritis, rheumatoid arthritis, Behcet's disease, inflammatory bowel diseases (e.g., Crohn's disease and ulcerative colitis), psoriasis, psoriatic arthritis, atopic dermatitis, contact dermatitis, and combinations thereof.

Some embodiments provide a method of treating, ameliorating, or preventing a disease, disorder, or condition associated with PDE4, comprising administering a therapeutically effective amount of a compound of any one of Formula (I), Formula (II), or a pharmaceutically acceptable salt of any of the foregoing, or a composition comprising any one of Formula (I) or Formula (II) to a subject in need thereof.

In some embodiments, the disease, disorder, or condition is selected from the group consisting of arthritis, ankylosing spondylitis, osteoarthritis, rheumatoid arthritis, Behcet's disease, inflammatory bowel diseases (e.g., Crohn's disease and ulcerative colitis), psoriasis, psoriatic arthritis, atopic dermatitis, contact dermatitis, and combinations thereof.

In some embodiments, the compound or composition is administered in combination with a second therapeutic agent.

In some embodiments, the second therapeutic agent is selected from the group consisting of anti-inflammatory agents, anti-cancer agents, immunostimulatory agents, and immunosuppressive agents. In some embodiments, the second therapeutic agent is an anti-inflammatory agent or an immunosuppressive agent.

Some embodiments provide a method of decreasing expression of a protein selected from TNF-α, INF-γ, IL-2, IL-17, IL-23, or a combination thereof, comprising contacting a cell with a compound of any one of Formula (I) or Formula (II), or a pharmaceutically acceptable salt of any of the foregoing. In some embodiments, the protein is TNF-α.

Some embodiments provide a method of inhibiting PDE4 activity, comprising contacting a cell with a compound of any one of Formula (I) or Formula (II), or a pharmaceutically acceptable salt of any of the foregoing.

Some embodiments provide a method of treating psoriasis, comprising topically administering a therapeutically effective amount of a composition comprising any one of Formula (I) or Formula (II), or a pharmaceutically acceptable salt of any of the foregoing, to a subject in need thereof.

In some embodiments, the subject is known to possess wild-type PDE4. In some embodiments, the subject is known to possess wild-type TNF-α. In some embodiments, the subject is known to possess wild-type INF-γ, IL-2, IL-17, or IL-23. In some embodiments, the subject is known to possess aberrant PDE4. In some embodiments, the subject is known to possess aberrant TNF-α. In some embodiments, the subject is known to possess aberrant INF-γ, IL-2, IL-17, or IL-23.

In some embodiments, the cell is known to possess wild-type PDE4. In some embodiments, the cell is known to possess wild-type TNF-α. In some embodiments, the cell is known to possess wild-type INF-γ, IL-2, IL-17, or IL-23. In some embodiments, the cell is known to possess aberrant PDE4. In some embodiments, the cell is known to possess aberrant TNF-α. In some embodiments, the cell is known to possess aberrant INF-γ, IL-2, IL-17, or IL-23.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DETAILED DESCRIPTION

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed.

The section headings used herein are for organizational purposes only and are not to be construed as limiting the subject matter described.

The term "protein malfunction," as used herein, refers to a protein or proteins not properly performing its intended biological function. For example, overexpression or underexpression and mutations in structure/function constitute a protein malfunction. Likewise, a protein or proteins that are expressed normally, and function normally, but are unable to perform their intended biological function (i.e., suppress tumor growth) are also malfunctioning proteins.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" an optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or an unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

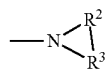

Whenever a group is described as being "an optionally substituted" that group may be an unsubstituted or substituted with one or more of the indicated substituents. Likewise, when a group is described as being "an unsubstituted or substituted" if substituted, the substituent may be selected from one or more the indicated substituents. If no substituents are indicated, it is meant that the indicated "an optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or an unsubstituted. Substituted alkyl groups include, but are not limited to benzyl, substituted benzyl, aminoalkyl, substituted aminoalkyl, carboxyalkyl, alkoxyalkyl, and the like.

As used herein, "alkenyl" refers to an alkyl group, as defined herein, that contains in the straight or branched hydrocarbon chain one or more double bonds. An alkenyl group may be an unsubstituted or substituted. Typical alkyl groups include, but are in no way limited to, vinyl, allyl, 1-propenyl, and 2-propenyl.

As used herein, "alkynyl" refers to an alkyl group as defined herein, that contains in the straight or branched hydrocarbon chain one or more triple bonds. An alkynyl group may be an unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged, or spiro fashion. Cycloalkyl groups can contain 3 to 10 atoms in the ring(s) or 3 to 8 atoms in the ring(s). A cycloalkyl group may be an unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused, bridged, or spiro fashion. A cycloalkenyl group may be an unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused, bridged, or spiro fashion. A cycloalkynyl group may be an unsubstituted or substituted.

As used herein, "carbocyclyl" or "cyclic hydrocarbyl" refers to all carbon ring systems. Such systems can be unsaturated, can include some unsaturation, or can contain some aromatic portion, or be all aromatic. Carbocyclyl group can contain from 3 to 30 carbon atoms. A carbocyclyl group may be an unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or an unsubstituted.

As used herein, "heterocyclyl" refers to mono- or polycyclic ring systems including at least one heteroatom (e.g., O, N, S), and up to five heteroatoms, for example, 1, 2, 3, 4, or 5 heteroatoms. Such systems can be unsaturated, can include some unsaturation, or can contain some aromatic portion, or be all aromatic. A heterocyclyl group can contain from 3 to 30 atoms. A heterocyclyl group may be an unsubstituted or substituted. Examples of heterocycles include, but are not limited to oxirane, aziridine, thiirane, diazidiridine, oxaziridine, azetidine, oxetane, thietane, oxazetidine, pyrrolidine, tetrahydrofuran, tetrahydrothiophene, imidazoline, pyrazolidine, oxazolidine, isoxazolidine, thiazolidine, isothiazolidine, dioxolane, dithiolane, piperidine, tetrahydropyran, thiane, piperazine, morpholine, thiomorpholine, dioxane, dithiane, azepine, diazepine, oxepane, dioxapane, oxazepane, thiazepane, thiepane, azocane, diazocane, oxocane, dioxocane, thiocane, dithiocane, oxazacane, and thiazacane. A heterocyclyl group may be substituted or unsubstituted.

As used herein, "heteroaryl" refers to a monocyclic or multicyclic aromatic ring system (a ring system having a least one ring with a fully delocalized pi-electron system) that contain(s) at least heteroatom, that is, an element other than carbon, including but not limited to, nitrogen, oxygen, and sulfur, and at least one aromatic ring and up to five heteroatoms, for example, 1, 2, 3, 4, or 5 heteroatoms. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or an unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may an optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused, bridged, or spiro fashion. Additionally, any nitrogens in a heteroalicyclic may be quaternized. Heteroalicyclyl or heteroalicyclic groups may be an unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

"Lower alkylene groups" are straight-chained —$CH_2$— tethering groups, forming bonds to connect molecular fragments via their terminal carbon atoms. Lower alkylene groups contain from 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "aralkyl" and "aryl(alkyl)" refer to an aryl group, as defined above, connected, as a substituent, via a lower alkylene group, as described above. The lower alkylene and aryl group of an aralkyl may be substituted or an unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via a lower alkylene group, as defined above. The lower alkylene and heteroaryl group of heteroaralkyl may be substituted or an unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclylic group, as defined above, connected, as a substituent, via a lower alkylene group, as defined above. The lower alkylene and heterocyclic or a heterocyclyl of a (heteroalicyclyl)alkyl may be substituted or an unsubstituted. Examples include but are not limited to tetrahydro-2H-pyran-4-yl)methyl, (piperidin-4-yl)ethyl, (piperidin-4-yl) propyl, (tetrahydro-2H-thiopyran-4-yl)methyl, and (1,3-thiazinan-4-yl)methyl.

As used herein, "alkoxy" refers to the formula —OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or an unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or an unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or an unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or an unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or an unsubstituted.

As used herein, "aryloxy" and "arylthio" refers to RO— and RS—, in which R is an aryl, as defined above, such as but not limited to phenyl. Both an aryloxy and arylthio may be substituted or an unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A sulfenyl may be substituted or an unsubstituted.

A "sulfinyl" group refers to an "—S(=O)—R" group in which R can be the same as defined with respect to sulfenyl. A sulfinyl may be substituted or an unsubstituted.

A "sulfonyl" group refers to an "$SO_2R$" group in which R can be the same as defined with respect to sulfenyl. A sulfonyl may be substituted or an unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or an unsubstituted.

The terms "ester" and "C-carboxy" refer to a "—C(=O)OR" group in which R can be the same as defined with respect to O-carboxy. An ester and C-carboxy may be substituted or an unsubstituted.

A "thiocarbonyl" group refers to a "—C(=S)R" group in which R can be the same as defined with respect to O-carboxy. A thiocarbonyl may be substituted or an unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An S-sulfonamido may be substituted or an unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-sulfonamido may be substituted or an unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-carbamyl may be substituted or an unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-carbamyl may be substituted or an unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An O-thiocarbamyl may be substituted or an unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-thiocarbamyl may be substituted or an unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A C-amido may be substituted or an unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. An N-amido may be substituted or an unsubstituted.

A "urea" group refers to a "—N($R_AR_B$)—C(=O)—N($R_AR_B$)—" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A urea group may be substituted or an unsubstituted.

A "thiourea" group refers to a "—N($R_AR_B$)—C(=S)—N($R_AR_B$)—" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined above. A thiourea group may be substituted or an unsubstituted.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4''-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. In some embodiments, the compounds described herein (for example, compounds of Formula (I) or Formula (II), and pharmaceutically acceptable salts of any of the foregoing) are present in a racemic mixture. In some embodiments, the compounds described herein (for example, compounds of Formula (I) or Formula (II), and pharmaceutically acceptable salts of any of the foregoing) are in the S-configuration.

In some embodiments, the compounds described herein (for example, compounds of Formula (I) or Formula (II), and pharmaceutically acceptable salts of any of the foregoing) are in the R-configuration.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

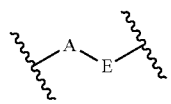

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Some embodiments provide a compound of Formula (I), Formula (II), or a pharmaceutically acceptable salt of any of the foregoing,

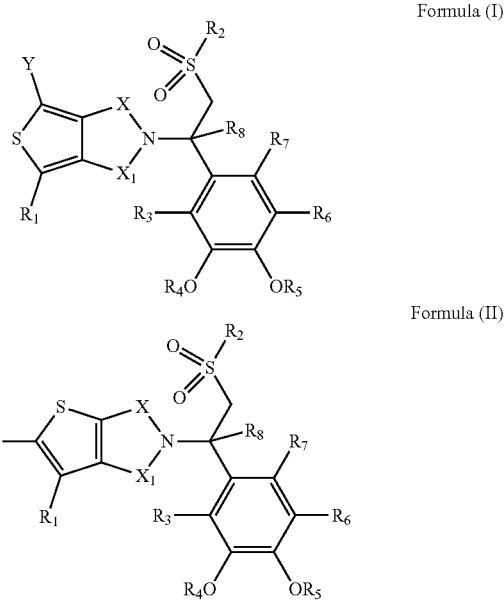

In some embodiments, X and $X_1$ are each independently $CH_2$, C=O, SO, $SO_2$, or $CH_2CO$. In some embodiments, X and $X_1$ are each independently $CH_2$ or C=O. In some embodiments, X and $X_1$ are each $CH_2$. In other embodiments, X and $X_1$ are each C=O. In still other embodiments, one of X and $X_1$ is C=O, and the other of X and $X_1$ is $CH_2$.

In some embodiments, Y is H. In some embodiments, Y is deuterium. In some embodiments, Y is halogen, for example, fluoro, chloro, or bromo. In some embodiments, Y is an optionally substituted $C_1$-$C_6$ alkyl, for example, methyl, ethyl, n-propyl, isopropyl, n-butyl, isobutyl, sec-butyl, or t-butyl.

In some embodiments, $R_1$ is —$NH_2$, —$NHR_{1A}$, —$NR_{1A}R_{1B}$, —NHC(O)$R_{1C}$, —$NR_{1A}$C(O)$R_{1C}$, —$NHSO_2R_{1C}$, or —$NHR_{1A}SO_2R_{1C}$. In some embodiments, $R_1$ is —N[C(O)$R_{1A}$][C(O)$R_{1C}$].

In some embodiments, $R_{1A}$, $R_{1B}$, and $R_{1C}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl.

In some embodiments, X and $X_1$ are each C=O, $R_1$ is —$NHR_{1A}$, and $R_{1A}$ is an optionally substituted $C_1$-$C_6$ alkyl or an optionally substituted $C_3$-$C_6$ cycloalkyl.

In some embodiments, X and $X_1$ are each C=O, $R_1$ is —$NR_{1A}R_{1B}$, and $R_{1A}$ and $R_{1B}$ are independently an optionally substituted $C_1$-$C_6$ alkyl or an optionally substituted $C_3$-$C_6$ cycloalkyl, for example, methyl, ethyl, n-propyl, isopropyl, n-butyl, isobutyl, sec-butyl, t-butyl, cyclopropyl, cyclobutyl, cyclopentyl, or cyclohexyl.

In some embodiments, X and $X_1$ are each C=O, $R_1$ is —NHC(O)$R_{1C}$, and $R_{1C}$ is an optionally substituted $C_6$-$C_{10}$ aryl or an optionally substituted 5 to 10 membered heteroaryl.

In some embodiments, X and $X_1$ are each C=O, $R_1$ is —$NR_{1A}$C(O)$R_{1C}$, and $R_{1A}$ and $R_{1C}$ are independently an optionally substituted $C_1$-$C_6$ alkyl, an optionally substituted $C_6$-$C_{10}$ aryl, or an optionally substituted 5 to 10 membered heteroaryl, for example, methyl, ethyl, n-propyl, isopropyl, n-butyl, isobutyl, sec-butyl, t-butyl, phenyl, naphthyl, furan, pyrrole, imidazole, thiophene, pyridine, or pyrimidine.

In some embodiments, X and $X_1$ are each C=O, $R_1$ is —N[C(O)$R_{1A}$][C(O)$R_{1C}$], and $R_{1A}$ and $R_{1C}$ are independently an optionally substituted $C_1$-$C_6$ alkyl, an optionally substituted $C_6$-$C_{10}$ aryl, or an optionally substituted 5 to 10 membered heteroaryl, for example, methyl, ethyl, n-propyl, isopropyl, n-butyl, isobutyl, sec-butyl, t-butyl, phenyl, naphthyl, furan, pyrrole, imidazole, thiophene, pyridine, or pyrimidine.

In some embodiments, $R_1$ is hydroxy. In some embodiments, $R_1$ is halogen, for example, fluoro, chloro, or bromo. In some embodiments, $R_1$ is nitro. In some embodiments, $R_1$ is cyano. In some embodiments, $R_1$ is optionally substituted $C_1$-$C_6$ alkoxy. In some embodiments, $R_1$ is —$NH_2$. In some embodiments, $R_1$ is —$NHR_{1A}$, —$NR_{1A}R_{1B}$, —NHC(O)$R_{1C}$, —$NR_{1A}$C(O)$R_{1C}$, —$NHSO_2R_{1C}$, or —$NR_{1A}SO_2R_{1C}$. In some embodiments, $R_1$ is —N[C(O)$R_{1A}$][C(O)$R_{1C}$]. In some embodiments, $R_1$ is an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments, $R_1$ is an optionally substituted $C_1$-$C_6$ alkyl. In some embodiments, $R_1$ is an optionally substituted $C_3$-$C_6$ cycloalkyl. In some embodiments, $R_1$ is an optionally substituted 3 to 10 membered heterocyclyl. In some embodiments, $R_1$ is an optionally substituted $C_6$-$C_{10}$ aryl. In some embodiments, $R_1$ is an optionally substituted 5 to 10 membered heteroaryl.

In some embodiments, $R_2$ is an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl.

In some embodiments, $R_2$ is an unsubstituted $C_1$-$C_6$ alkyl, an unsubstituted $C_3$-$C_6$ cycloalkyl, an unsubstituted 3 to 10 membered heterocyclyl, an unsubstituted $C_6$-$C_{10}$ aryl, or an unsubstituted 5 to 10 membered heteroaryl.

In some embodiments, $R_2$ is an optionally substituted $C_1$-$C_6$ alkyl, for example, methyl, ethyl, n-propyl, isopropyl, n-butyl, isobutyl, sec-butyl, or t-butyl. In some embodiments, $R_2$ is an optionally substituted $C_3$-$C_6$ cycloalkyl, for example, cyclopropyl, cyclobutyl, cyclopentyl, or cyclohexyl.

In some embodiments, $R_3$, $R_6$, and $R_7$ are independently selected from a hydrogen, a deuterium, a halogen, an optionally substituted $C_1$-$C_6$ alkyl, an optionally substituted $C_1$-$C_6$ alkoxy, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl.

In some embodiments, $R_3$, $R_6$, and $R_7$ are each hydrogen. In some embodiments, one of $R_3$, $R_6$, and $R_7$ is halogen, and the other two are hydrogen. In some embodiments, one of $R_3$, $R_6$, and $R_7$ is an optionally substituted $C_1$-$C_6$ alkyl, and the other two are hydrogen. In some embodiments, two of $R_3$, $R_6$, and $R_7$ are halogen, and the other one is hydrogen. In some embodiments, two of $R_3$, $R_6$, and $R_7$ are an optionally substituted $C_1$-$C_6$ alkyl, and the other one is hydrogen.

In some embodiments, $R_4$ and $R_5$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl. In some embodiments, $R_4$ and $R_5$ are independently selected from an optionally substituted $C_1$-$C_6$ alkyl, for example, methyl, ethyl, n-propyl, isopropyl, n-butyl, isobutyl, sec-butyl, or t-butyl. In some embodiments, $R_4$ and $R_5$ are independently an optionally substituted $C_3$-$C_6$ cycloalkyl, for example, cyclopropyl, cyclobutyl, cyclopentyl, or cyclohexyl. In some embodiments, one of $R_4$ and $R_5$ is an optionally substituted $C_1$-$C_6$ alkyl and the other is an optionally substituted $C_3$-$C_6$ cycloalkyl.

In some embodiments, $R_4$ and $R_5$, together with the atoms to which they are attached, form an optionally substituted 5 or 6 membered heterocyclyl, for example, an optionally substituted dioxolane or an optionally substituted 1,4-dioxane. In some embodiments, $R_4$ and $R_5$, together with the atoms to which they are attached, form an unsubstituted dioxolane or an unsubstituted 1,4-dioxane.

In some embodiments, when $R_2$ is an optionally substituted $C_1$-$C_6$ alkyl, at least one of $R_4$ and $R_5$ is an optionally substituted $C_3$-$C_6$ cycloalkyl, an optionally substituted 3 to 10 membered heterocyclyl, an optionally substituted $C_6$-$C_{10}$ aryl, an optionally substituted 5 to 10 membered heteroaryl, or $R_4$ and $R_5$, together with the atoms to which they are attached, form an optionally substituted 5 or 6 membered heterocyclyl. In some embodiments, when $R_2$ is an optionally substituted $C_1$-$C_4$ alkyl or NH($C_1$-$C_6$ alkyl), at least one of $R_4$ and $R_5$ is an optionally substituted cyclopropyl. In some embodiments, when $R_2$ is an optionally substituted $C_1$-$C_6$ alkyl, $R_4$ and $R_5$ are independently selected from an optionally substituted $C_3$-$C_6$ cycloalkyl. In some embodiments, when $R_2$ is an optionally substituted $C_1$-$C_6$ alkyl, $R_4$ is an optionally substituted $C_3$-$C_6$ cycloalkyl and $R_5$ is an optionally substituted $C_1$-$C_6$ alkyl. In some embodiments, when $R_2$ is an optionally substituted $C_1$-$C_6$ alkyl, $R_5$ is an optionally substituted $C_3$-$C_6$ cycloalkyl and $R_4$ is an optionally substituted $C_1$-$C_6$ alkyl. In some embodiments, when $R_2$ is an optionally substituted $C_1$-$C_6$ alkyl, $R_4$ and $R_5$, together with the atoms to which they are attached, form an optionally substituted 5 or 6 membered heterocyclyl, for example, an optionally substituted dioxolane or an optionally substituted 1,4-dioxane.

In some embodiments, when a $C_1$-$C_6$ alkyl, a $C_1$-$C_6$ alkoxy, a $C_3$-$C_6$ cycloalkyl, a $C_6$-$C_{10}$ aryl, a 3 to 10 membered heterocyclyl, or a 5 to 10 membered heteroaryl is substituted, the substituted substituents are independently selected from a deuterium, an oxo, a halogen, cyano, a nitro, an optionally substituted $C_1$-$C_6$ alkyl, an optionally substituted $C_1$-$C_6$ haloalkyl, an optionally substituted $C_1$-$C_6$ alkoxy, an optionally substituted $C_3$-$C_6$ cycloalkyl, an optionally substituted $C_6$-$C_{10}$ aryl, an optionally substituted 3 to 10 membered heterocyclyl, an optionally substituted 5 to 10 membered heteroaryl, —C(O)$R_A$, —C(O)O$R_A$, —C(O)$NR_BR_C$, —O$R_A$, —OC(O)$R_A$, —OC(O)$NR_BR_C$, —OS(O)$R_A$, —OS(O)$_2R_A$, —OS(O)$NR_BR_C$, —OS(O)$_2NR_BR_C$, —$NR_BR_C$, —$NR_A$C(O)$R_A$, —$NR_A$C(O)O$R_A$, —$NR_A$C(O)$NR_BR_C$, —$NR_A$S(O)$R_A$, —$NR_A$S(O)$_2R_A$, —NR$_A$S(O)NR$_B$R$_C$, —NR$_A$S(O)$_2$NR$_B$R$_C$, —SR$_A$, —S(O)R$_A$, —S(O)$_2$R$_A$, —S(O)NR$_B$R$_C$, and —S(O)$_2$NR$_B$R$_C$.

In some embodiments, each R$_A$, R$_B$, and R$_C$ are independently selected from a hydrogen, an unsubstituted C$_1$-C$_6$ alkyl, an unsubstituted C$_2$-C$_6$ alkenyl, an unsubstituted C$_3$-C$_6$ cycloalkyl, an unsubstituted 3 to 10 membered heterocyclyl, an unsubstituted C$_6$-C$_{10}$ aryl, and an unsubstituted 5 to 10 membered heteroaryl.

In some embodiments, R$_B$ and R$_C$, together with the nitrogen atom to which they are attached, form an optionally substituted 3 to 10 membered heterocyclyl.

In some embodiments, one of X and X$_1$ is CH$_2$ and the other is C=O. In some embodiments, X and X$_1$ are each CH$_2$. In some embodiments, X and X$_1$ are each C=O. In some embodiments, one of X and X$_1$ is CH$_2$ and the other is SO. In some embodiments, one of X and X$_1$ is CH$_2$ and the other is SO$_2$. In some embodiments, one of X and X$_1$ is CH$_2$ and the other is CH$_2$CO. In some embodiments, one of X and X$_1$ is C=O and the other one of X and X$_1$ is SO. In some embodiments, one of X and X$_1$ is C=O and the other one of X and X$_1$ is SO$_2$. In some embodiments, one of X and X$_1$ is C=O and the other is CH$_2$CO.

In some embodiments, R$_1$ is —NHR$_{1A}$, —NHC(O)R$_{1C}$ or —NR$_{1A}$C(O)R$_{1C}$. In some embodiments, R$_1$ is —NHC(O)R$_{1C}$. In some embodiments, R$_1$ is —N[C(O)R$_{1A}$][C(O)R$_{1C}$]. In some embodiments, R$_{1A}$, R$_{1B}$, and R$_{1C}$ are independently an optionally substituted C$_1$-C$_6$ alkyl or an optionally substituted C$_3$-C$_6$ cycloalkyl. In some embodiments, R$_{1C}$ is an optionally substituted C$_1$-C$_6$ alkyl. In some embodiments, R$_{1C}$ is an unsubstituted C$_1$-C$_6$ alkyl.

In some embodiments, R$_3$, R$_6$, and R$_7$ are independently selected from a hydrogen, a halogen, and an optionally substituted C$_1$-C$_6$ alkyl. In some embodiments, R$_3$, R$_6$, and R$_7$ are each hydrogen.

In some embodiments, R$_8$ is hydrogen or deuterium. In some embodiments, R$_8$ is hydrogen. In other embodiments, R$_8$ is deuterium.

In some embodiments, R$_2$ is an optionally substituted C$_1$-C$_6$ alkyl and one of R$_4$ and R$_5$ is an optionally substituted C$_1$-C$_6$ alkyl and the other is an optionally substituted C$_3$-C$_6$ cycloalkyl or an optionally substituted 3 to 10 membered heterocyclyl.

In some embodiments, R$_2$ is an unsubstituted C$_1$-C$_6$ alkyl and one of R$_4$ and R$_5$ is an unsubstituted C$_1$-C$_6$ alkyl and the other is an optionally substituted C$_3$-C$_6$ cycloalkyl or an optionally substituted 3 to 10 membered heterocyclyl.

In some embodiments, R$_2$ is an optionally substituted C$_3$-C$_6$ cycloalkyl, an optionally substituted 3 to 10 membered heterocyclyl, an optionally substituted C$_6$-C$_{10}$ aryl, or an optionally substituted 5 to 10 membered heteroaryl, and R$_4$ and R$_5$ are independently an optionally substituted C$_1$-C$_6$ alkyl.

In some embodiments, R$_2$ is an optionally substituted C$_3$-C$_6$ cycloalkyl, an optionally substituted 3 to 10 membered heterocyclyl, an optionally substituted C$_6$-C$_{10}$ aryl, or an optionally substituted 5 to 10 membered heteroaryl, and R$_4$ and R$_5$ are independently unsubstituted C$_1$-C$_6$ alkyl.

In some embodiments, R$_4$ and R$_5$, together with the atoms to which they are attached, form an optionally substituted 5 or 6 membered heterocyclyl.

In some embodiments, R$_4$ and R$_5$, together with the atoms to which they are attached, form an unsubstituted 5 or 6 membered heterocyclyl.

In some embodiments, R$_4$ and R$_5$, together with the atoms to which they are attached, form an unsubstituted 5 membered heterocyclyl.

In some embodiments, R$_4$ and R$_5$, together with the atoms to which they are attached, form an unsubstituted 6 membered heterocyclyl.

In some embodiments, the compound of Formula (I) is selected from:

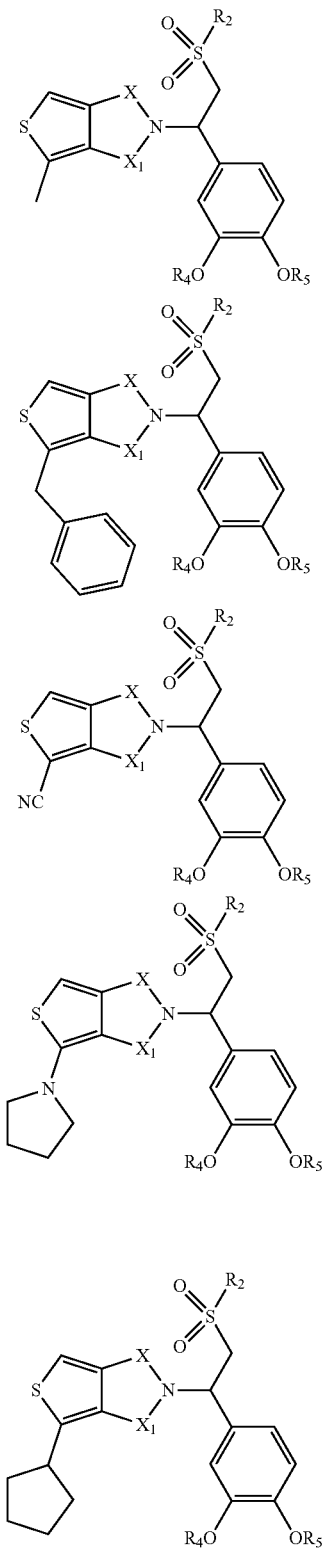

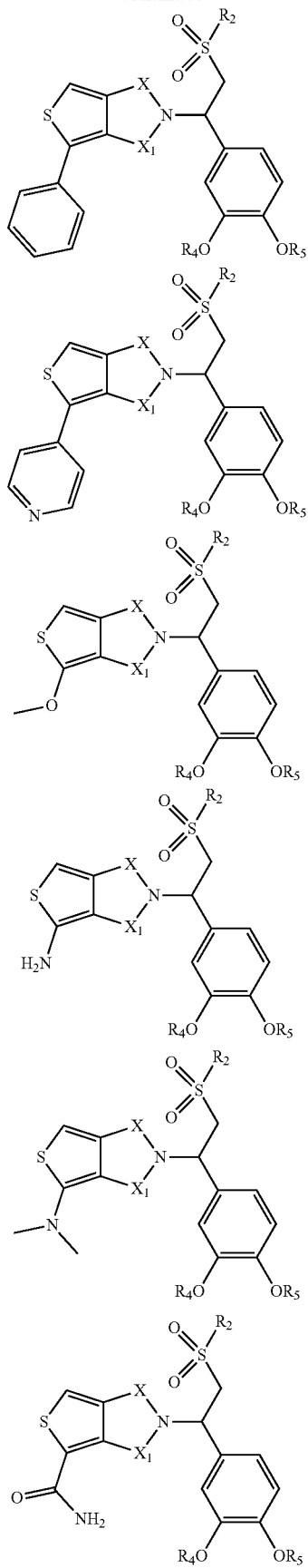
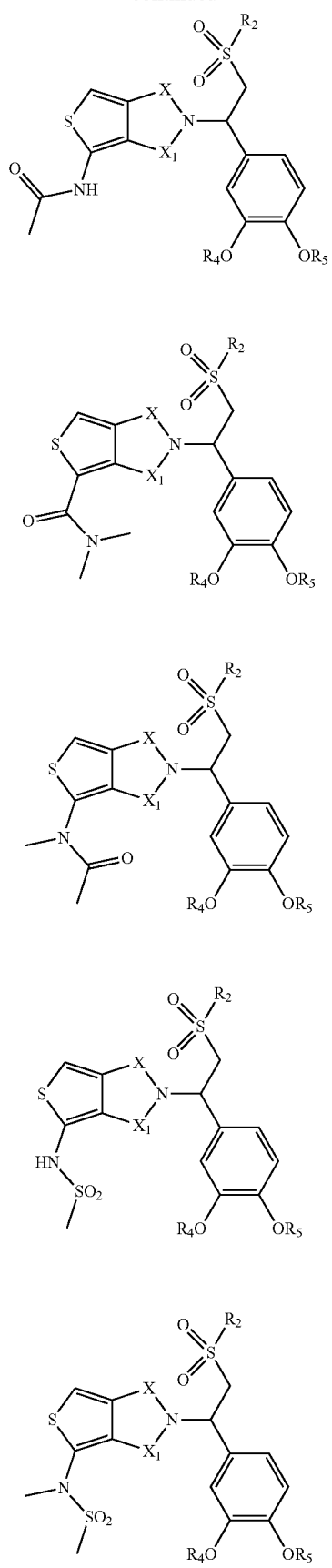

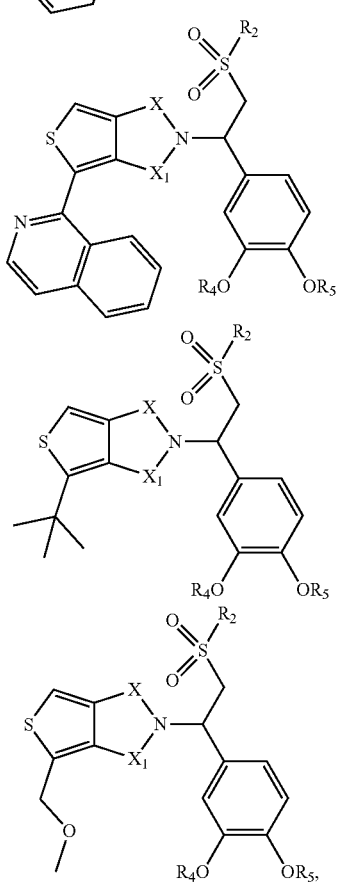

or a pharmaceutically acceptable salt of any of the foregoing. In some embodiments of this paragraph, X and $X_1$ are each independently $CH_2$, C=O, SO, $SO_2$, or $CH_2CO$. In some embodiments of this paragraph, X and $X_1$ are each $CH_2$. In some embodiments of this paragraph, X and $X_1$ are each C=O. In some embodiments of this paragraph, X and $X_1$ are each SO. In some embodiments of this paragraph, X and $X_1$ are each $SO_2$. In some embodiments of this paragraph, X and $X_1$ are each $CH_2CO$. In some embodiments of this paragraph, one of X and $X_1$ is $CH_2$ and the other of X and $X_1$ is C=O. In some embodiments of this paragraph, one of X and $X_1$ is $CH_2$ and the other of X and $X_1$ is SO. In some embodiments of this paragraph, one of X and $X_1$ is $CH_2$ and the other of X and $X_1$ is $SO_2$. In some embodiments of this paragraph, one of X and $X_1$ is $CH_2$ and the other of X and $X_1$ is $CH_2CO$. In some embodiments of this paragraph, one of X and $X_1$ is C=O and the other of X and $X_1$ is SO. In some embodiments of this paragraph, one of X and $X_1$ is C=O and the other of X and $X_1$ is $SO_2$. In some embodiments of this paragraph, one of X and $X_1$ is C=O and the other of X and $X_1$ is $CH_2CO$. In some embodiments of this paragraph, $R_2$ is hydroxy, $-NH_2$, $-NHR_{1A}$, $-NR_{1A}R_{1B}$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_2$ is hydroxy. In some embodiments of this paragraph, $R_2$—$NH_2$. In some embodiments of this paragraph, $R_2$ is an optionally substituted $C_1$-$C_6$ alkyl, for example, methyl, ethyl, propyl, isopropyl, butyl, sec-buty, t-butyl, $-CF_3$, $-CH_2F$, $-CF_2H$, $-CD_3$, $-C(CH_3)_2CF_3$, benzyl, or substituted benzyl In some embodiments of this paragraph, $R_2$ is an optionally substituted $C_3$-$C_6$ cycloalkyl, for example, cyclopropyl, cyclobutyl, cyclopentyl, cyclohexyl, 2,2-difluorocyclopropyl, or 2,2-difluorocyclobutyl. In some embodiments of this paragraph, $R_2$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is an optionally substituted $C_6$-$C_{10}$ aryl, for example, substituted phenyl, unsubstituted phenyl, naphthyl, or unsubstituted naphthyl. In some embodiments of this paragraph, $R_2$ is optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_{1A}$ and $R_{1B}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_2$ is —$NHR_{1A}$, and $R_{1A}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_2$ is —$NHR_{1A}$, and $R_{1A}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_2$ is —$NHR_{1A}$, and $R_{1A}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is —$NHR_{1A}$, and $R_{1A}$ is an optionally substituted $C_6$-$C_{10}$ aryl, for example, substituted phenyl, unsubstituted phenyl, naphthyl, or unsubstituted naphthyl. In some embodiments of this paragraph, $R_2$ is —$NHR_{1A}$, and $R_{1A}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_2$ is —$NR_{1A}R_{1B}$, and $R_{1A}$ and $R_{1B}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_2$ is —$NR_{1A}R_{1B}$, and $R_{1A}$ and $R_{1B}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_2$ is —$NR_{1A}R_{1B}$, and $R_{1A}$ and $R_{1B}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is —$NR_{1A}R_{1B}$, and $R_{1A}$ and $R_{1B}$ are independently an optionally substituted $C_6$-$C_{10}$ aryl, for example, substituted phenyl, unsubstituted phenyl, naphthyl, or unsubstituted naphthyl. In some embodiments of this paragraph, $R_2$ is —$NR_{1A}R_{1B}$, and $R_{1A}$ and $R_{1B}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_2$ is —$NR_{1A}R_{1B}$, one of $R_{1A}$ and $R_{1B}$ is an optionally substituted $C_1$-$C_6$ alkyl and the other of $R_{1A}$ and $R_{1B}$ is an optionally substituted $C_6$-$C_{10}$ aryl or an optionally substituted 3 to 10 membered heterocyclyl. In some embodiments of this paragraph, $R_4$ and $R_5$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl. In some embodiments of this paragraph, $R_4$ and $R_5$, together with the atoms to which they are attached, form an optionally substituted 5 or 6 membered heterocyclyl. In some embodiments of this paragraph, $R_4$ and $R_5$ are independently selected from an optionally substituted $C_1$-$C_6$ alkyl. In some embodiments of this paragraph, $R_4$ and $R_5$ are independently selected from an optionally substituted $C_3$-$C_6$ cycloalkyl. In some embodiments of this paragraph, $R_4$ and $R_5$ are independently selected from, an optionally substituted 3 to 10 membered heterocyclyl. In some embodiments of this paragraph, $R_4$ and $R_5$ are independently selected from an optionally substituted $C_6$-$C_{10}$ aryl. In some embodiments of this paragraph, $R_4$ and $R_5$ are independently selected from and an optionally substituted 5 to 10 membered heteroaryl. In some embodiments of this paragraph, one of $R_4$ and $R_5$ is an optionally substituted $C_1$-$C_6$ alkyl and the other of $R_4$ and $R_5$ is an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, one of $R_4$ and $R_5$ is an optionally substituted $C_1$-$C_6$ alkyl and the other of $R_4$ and $R_5$ is an unsubstituted $C_3$-$C_6$ cycloalkyl, an unsubstituted 3 to 10 membered heterocyclyl, an unsubstituted $C_6$-$C_{10}$ aryl, or an unsubstituted 5 to 10 membered heteroaryl. In some embodiments of this paragraph, one of $R_4$ and $R_5$ is an unsubstituted $C_1$-$C_6$ alkyl and the other of $R_4$ and $R_5$ is an unsubstituted $C_3$-$C_6$ cycloalkyl, an unsubstituted 3 to 10 membered heterocyclyl, an unsubstituted $C_6$-$C_{10}$ aryl, or an unsubstituted 5 to 10 membered heteroaryl. In some embodiments of this paragraph, when $R_2$ is an optionally substituted $C_1$-$C_4$ alkyl or $NH(C_1$-$C_6$ alkyl), at least one of $R_4$ and $R_5$ is an optionally substituted cyclopropyl, an optionally substituted 3 to 10 membered heterocyclyl, an optionally substituted $C_6$-$C_{10}$ aryl, an optionally-substituted 5 to 10 membered heteroaryl, or $R_4$ and $R_5$, together with the atoms to which they are attached, form an optionally substituted 5 or 6 membered heterocyclyl.

In some embodiments, the compound of Formula (II) is selected from:

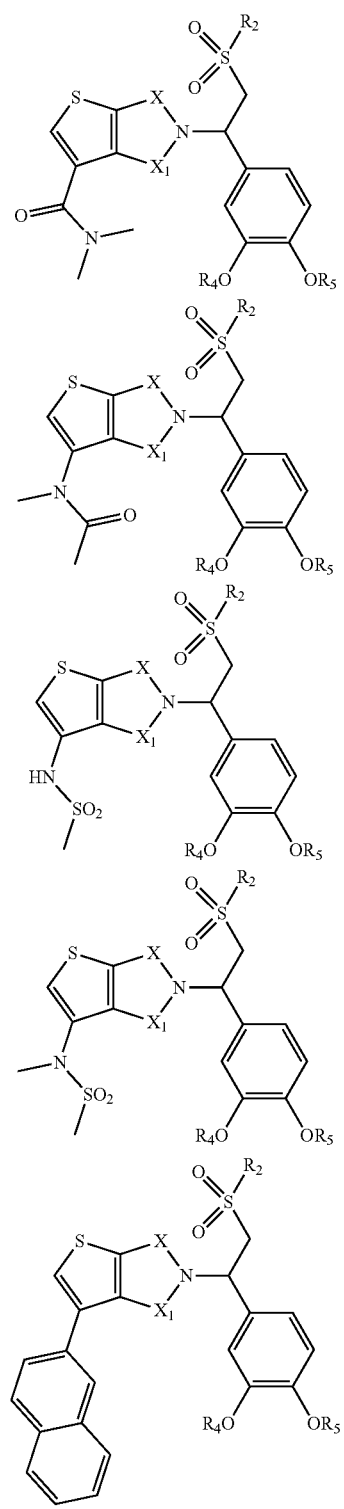

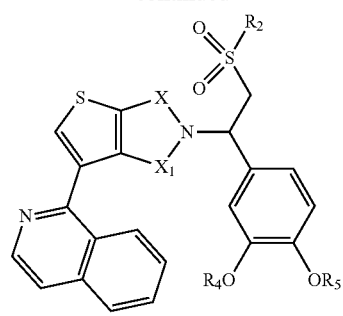
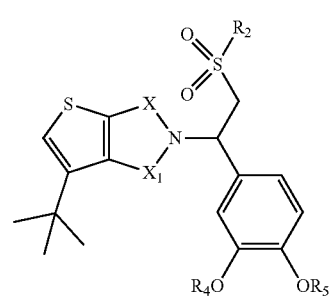
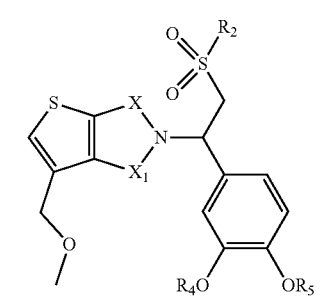
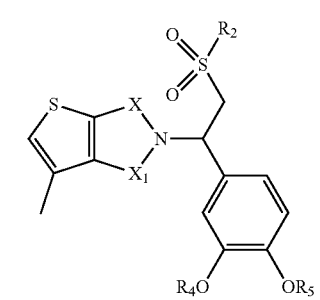
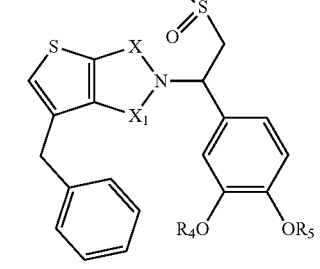
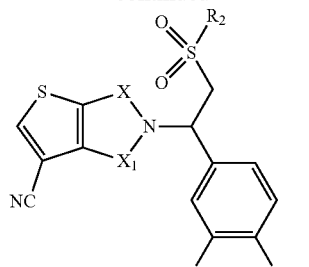
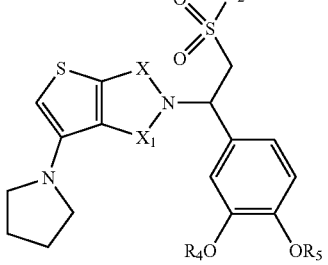
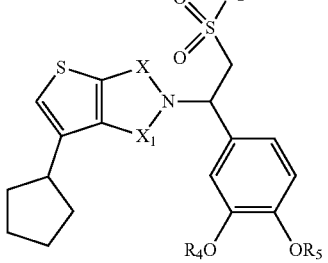
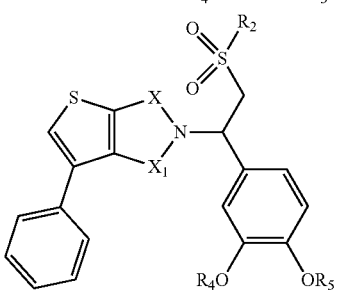
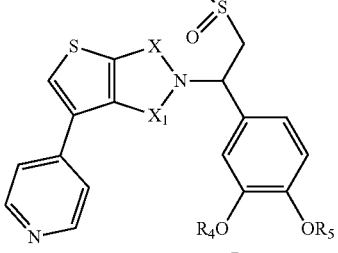
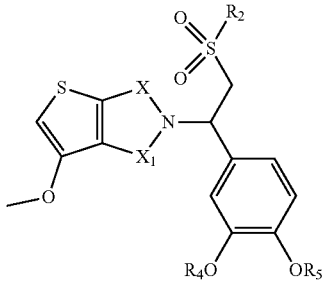

-continued

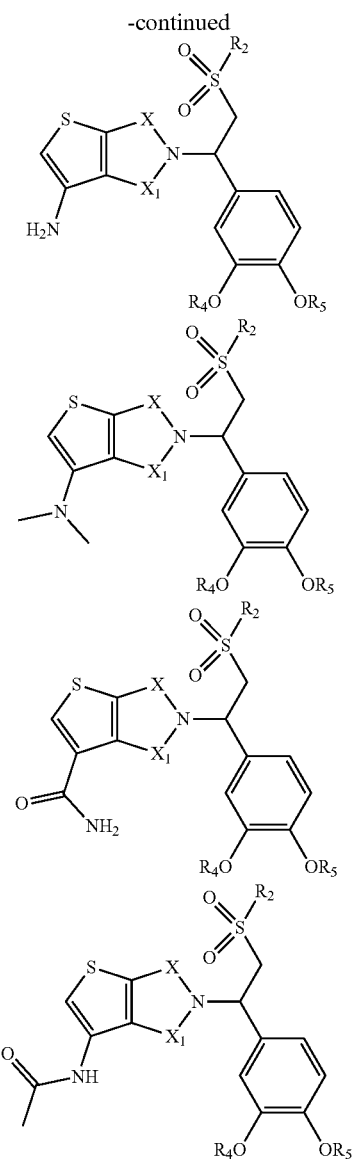

or a pharmaceutically acceptable salt of any of the foregoing. In some embodiments of this paragraph, X and $X_1$ are each independently $CH_2$, C=O, SO, $SO_2$, or $CH_2CO$. In some embodiments of this paragraph, X and $X_1$ are each $CH_2$. In some embodiments of this paragraph, X and $X_1$ are each C=O. In some embodiments of this paragraph, X and $X_1$ are each SO. In some embodiments of this paragraph, X and $X_1$ are each $SO_2$. In some embodiments of this paragraph, X and $X_1$ are each $CH_2CO$. In some embodiments of this paragraph, one of X and $X_1$ is $CH_2$ and the other of X and $X_1$ is C=O. In some embodiments of this paragraph, one of X and $X_1$ is $CH_2$ and the other of X and $X_1$ is SO. In some embodiments of this paragraph, one of X and $X_1$ is $CH_2$ and the other of X and $X_1$ is $SO_2$. In some embodiments of this paragraph, one of X and $X_1$ is $CH_2$ and the other of X and $X_1$ is $CH_2CO$. In some embodiments of this paragraph, one of X and $X_1$ is C=O and the other of X and $X_1$ is SO. In some embodiments of this paragraph, one of X and $X_1$ is C=O and the other of X and $X_1$ is $SO_2$. In some embodiments of this paragraph, one of X and $X_1$ is C=O and the other of X and $X_1$ is $CH_2CO$. In some embodiments of this paragraph, $R_2$ is hydroxy, $-NH_2$, $-NHR_{1A}$, $-NR_{1A}R_{1B}$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_2$ is hydroxy. In some embodiments of this paragraph, $R_2$—$NH_2$. In some embodiments of this paragraph, $R_2$ is an optionally substituted $C_1$-$C_6$ alkyl, for example, methyl, ethyl, propyl, isopropyl, butyl, sec-buty, t-butyl, $-CF_3$, $-CH_2F$, $-CF_2H$, $-CD_3$, $-C(CH_3)_2CF_3$, benzyl, or substituted benzyl In some embodiments of this paragraph, $R_2$ is an optionally substituted $C_3$-$C_6$ cycloalkyl, for example, cyclopropyl, cyclobutyl, cyclopentyl, cyclohexyl, 2,2-difluorocyclopropyl, or 2,2-difluorocyclobutyl. In some embodiments of this paragraph, $R_2$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is an optionally substituted $C_6$-$C_{10}$ aryl, for example, substituted phenyl, unsubstituted phenyl, naphthyl, or unsubstituted naphthyl. In some embodiments of this paragraph, $R_2$ is optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_{1A}$ and $R_{1B}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_2$ is $-NHR_{1A}$, and $R_{1A}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_2$ is $-NHR_{1A}$, and $R_{1A}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_2$ is $-NHR_{1A}$, and $R_{1A}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is $-NHR_{1A}$, and $R_{1A}$ is an optionally substituted $C_6$-$C_{10}$ aryl, for example, substituted phenyl, unsubstituted phenyl, naphthyl, or unsubstituted naphthyl. In some embodiments of this paragraph, $R_2$ is $-NHR_{1A}$, and $R_{1A}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_2$ is $-NR_{1A}R_{1B}$, and $R_{1A}$ and $R_{1B}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_2$ is $-NR_{1A}R_{1B}$, and $R_{1A}$ and $R_{1B}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_2$ is —$NR_{1A}R_{1B}$, and $R_{1A}$ and $R_{1B}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_2$ is —$NR_{1A}R_{1B}$, and $R_{1A}$ and $R_{1B}$ are independently an optionally substituted $C_6$-$C_{10}$ aryl, for example, substituted phenyl, unsubstituted phenyl, naphthyl, or unsubstituted naphthyl. In some embodiments of this paragraph, $R_2$ is —$NR_{1A}R_{1B}$, and $R_{1A}$ and $R_{1B}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_2$ is —$NR_{1A}R_{1B}$, one of $R_{1A}$ and $R_{1B}$ is an optionally substituted $C_1$-$C_6$ alkyl and the other of $R_{1A}$ and $R_{1B}$ is an optionally substituted $C_6$-$C_{10}$ aryl or an optionally substituted 3 to 10 membered heterocyclyl. In some embodiments of this paragraph, $R_4$ and $R_5$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl. In some embodiments of this paragraph, $R_4$ and $R_5$, together with the atoms to which they are attached, form an optionally substituted 5 or 6 membered heterocyclyl. In some embodiments of this paragraph, $R_4$ and $R_5$ are independently selected from an optionally substituted $C_1$-$C_6$ alkyl. In some embodiments of this paragraph, $R_4$ and $R_5$ are independently selected from an optionally substituted $C_3$-$C_6$ cycloalkyl. In some embodiments of this paragraph, $R_4$ and $R_5$ are independently selected from, an optionally substituted 3 to 10 membered heterocyclyl. In some embodiments of this paragraph, $R_4$ and $R_5$ are independently selected from an optionally substituted $C_6$-$C_{10}$ aryl. In some embodiments of this paragraph, $R_4$ and $R_5$ are independently selected from and an optionally substituted 5 to 10 membered heteroaryl. In some embodiments of this paragraph, one of $R_4$ and $R_5$ is an optionally substituted $C_1$-$C_6$ alkyl and the other of $R_4$ and $R_5$ is an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, one of $R_4$ and $R_5$ is an optionally substituted $C_1$-$C_6$ alkyl and the other of $R_4$ and $R_5$ is an unsubstituted $C_3$-$C_6$ cycloalkyl, an unsubstituted 3 to 10 membered heterocyclyl, an unsubstituted $C_6$-$C_{10}$ aryl, or an unsubstituted 5 to 10 membered heteroaryl. In some embodiments of this paragraph, one of $R_4$ and $R_5$ is an unsubstituted $C_1$-$C_6$ alkyl and the other of $R_4$ and $R_5$ is an unsubstituted $C_3$-$C_6$ cycloalkyl, an unsubstituted 3 to 10 membered heterocyclyl, an unsubstituted $C_6$-$C_{10}$ aryl, or an unsubstituted 5 to 10 membered heteroaryl. In some embodiments of this paragraph, when $R_2$ is an optionally substituted $C_1$-$C_4$ alkyl or $NH(C_1$-$C_6$ alkyl), at least one of $R_4$ and $R_5$ is an optionally substituted cyclopropyl, an optionally substituted 3 to 10 membered heterocyclyl, an optionally substituted $C_6$-$C_{10}$ aryl, an optionally-substituted 5 to 10 membered heteroaryl, or $R_4$ and $R_5$, together with the atoms to which they are attached, form an optionally substituted 5 or 6 membered heterocyclyl.

In some embodiments, the compound of Formula (I) is selected from:

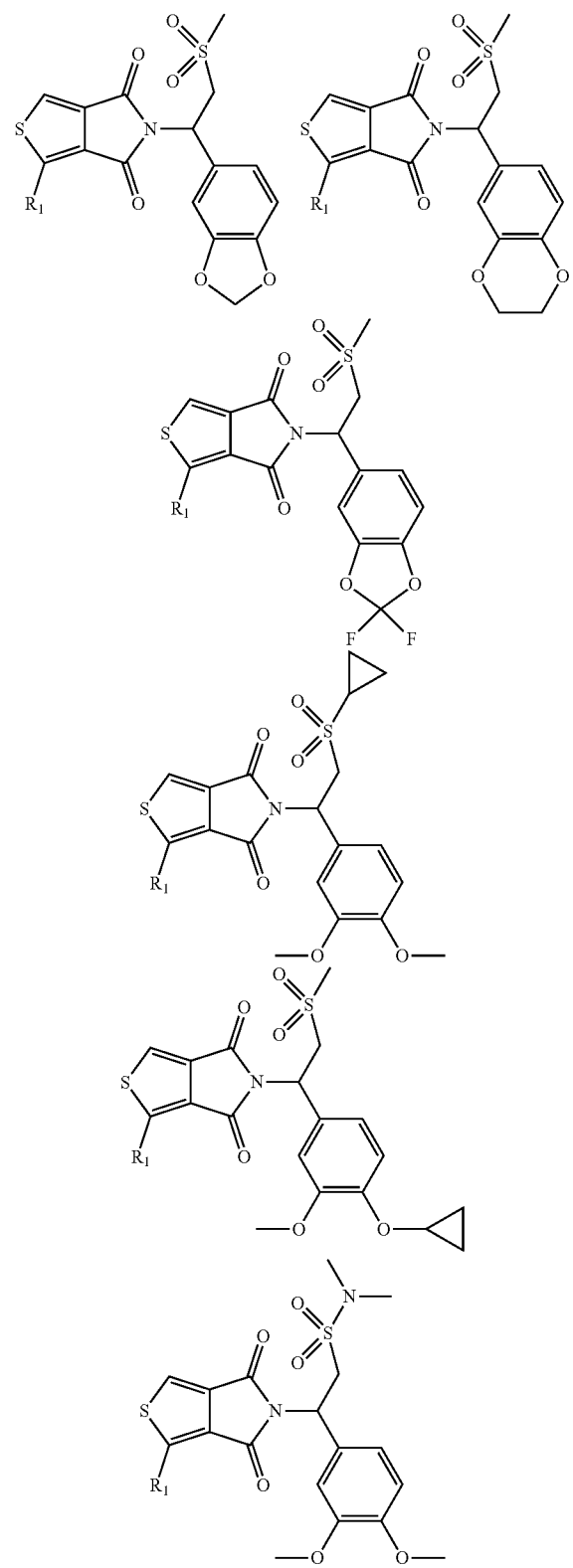

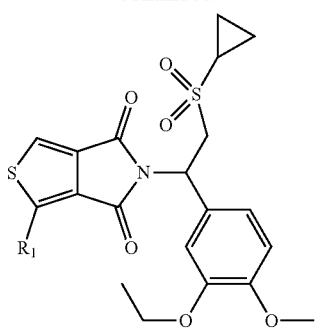

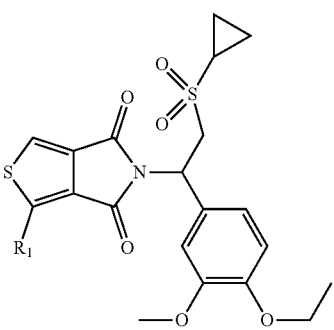

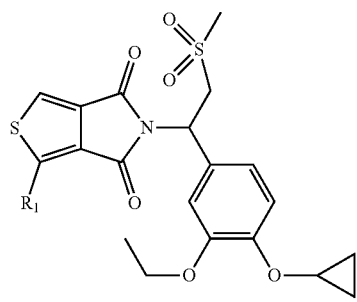

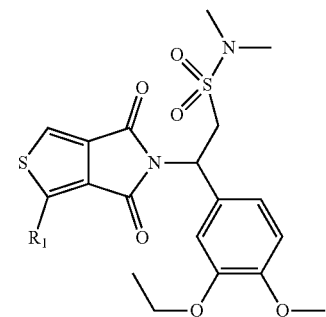

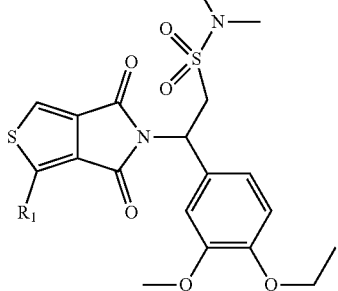

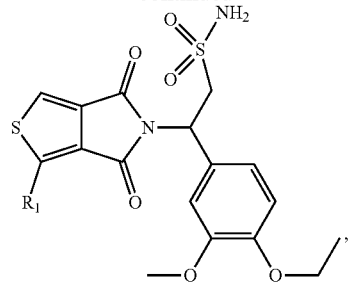

or a pharmaceutically acceptable salt of any of the foregoing. In some embodiments of this paragraph, $R_1$ is H, deuterium, hydroxy, halogen, nitro, cyano, optionally substituted $C_1$-$C_6$ alkoxy, —$NH_2$, —$NHR_{1A}$, —$NR_{1A}R_{1B}$, —$NHC(O)R_{1C}$, —$NR_{1A}C(O)R_{1C}$, —$NHSO_2R_{1C}$, —$NR_{1A}SO_2R_{1C}$, —$N[C(O)R_{1A}][C(O)R_{1C}]$. an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_{1A}$, $R_{1B}$, and $R_{1C}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_1$ is H. In some embodiments of this paragraph, $R_1$ is hydroxy. In some embodiments of this paragraph, $R_1$ is nitro. In some embodiments of this paragraph, $R_1$ is cyano. In some embodiments of this paragraph, $R_1$ is halogen, for example, fluoro, chloro, or bromo. In some embodiments of this paragraph, $R_1$ is optionally substituted $C_1$-$C_6$ alkoxy, for example, methoxy, ethoxy, propoxy, isopropoxy, butoxy, sec-butoxy, t-butoxy, —$OCF_3$, or —$OCD_3$. In some embodiments of this paragraph, $R_1$ is an optionally substituted $C_1$-$C_6$ alkyl, for example, methyl, ethyl, propyl, isopropyl, butyl, sec-buty, t-butyl, —$CF_3$, —$CH_2F$, —$CF_2H$, —$CD_3$, —$C(CH_3)_2CF_3$, benzyl, or substituted benzyl In some embodiments of this paragraph, $R_1$ is —$NH_2$. In some embodiments of this paragraph, $R_1$ is an optionally substituted $C_3$-$C_6$ cycloalkyl, for example, cyclopropyl, cyclobutyl, cyclopentyl, cyclohexyl, 2,2-difluorocyclopropyl, or 2,2-difluorocyclobutyl. In some embodiments of this paragraph, $R_1$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is an optionally substituted $C_6$-$C_{10}$ aryl, for example, substituted phenyl, unsubstituted phenyl, naphthyl, or unsubstituted naphthyl. In some embodiments of this paragraph, $R_1$ is optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NHR_{1A}$, and $R_{1A}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHR_{1A}$, and $R_{1A}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NHR_{1A}$, and $R_{1A}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHR_{1A}$, and $R_{1A}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHR_{1A}$, and $R_{1A}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}R_{1B}$, and $R_{1A}$ and $R_{1B}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NR_{1A}R_{1B}$, and $R_{1A}$ and $R_{1B}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NR_{1A}R_{1B}$, and $R_{1A}$ and $R_{1B}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NR_{1A}R_{1B}$, and $R_{1A}$ and $R_{1B}$ are independently an optionally substituted $C_6$-$C_{10}$ aryl, for example, substituted phenyl, unsubstituted phenyl, naphthyl, or unsubstituted naphthyl. In some embodiments of this paragraph, $R_1$ is —$NR_{1A}R_{1B}$, and $R_{1A}$ and $R_{1B}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}R_{1B}$, one of $R_{1A}$ and $R_{1B}$ is an optionally substituted $C_1$-$C_6$ alkyl and the other of $R_{1A}$ and $R_{1B}$ is an optionally substituted $C_6$-$C_{10}$ aryl or an optionally substituted 3 to 10 membered heterocyclyl. In some embodiments of this paragraph, $R_1$ is —$NHC(O)R_{1C}$, and $R_{1C}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHC(O)R_{1C}$, and $R_{1C}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NHC(O)R_{1C}$, and $R_{1C}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHC(O)R_{1C}$, and $R_{1C}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHC(O)R_{1C}$, and $R_{1C}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NHSO_2R_{1C}$, and $R_{1C}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHSO_2R_{1C}$, and $R_{1C}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$N[C(O)R_{1A}][C(O)R_{1C}]$, and $R_{1A}$ and $R_{1C}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHSO_2R_{1C}$, and $R_{1C}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHSO_2R_{1C}$, and $R_{1C}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHSO_2R_{1C}$, and $R_{1C}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}C(O)R_{1C}$, and $R_{1A}$ and $R_{1C}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NR_{1A}C(O)R_{1C}$, and $R_{1A}$ and $R_{1C}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NR_{1A}C(O)R_{1C}$, and $R_{1A}$ and $R_{1C}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NR_{1A}C(O)R_{1C}$, and $R_{1A}$ and $R_{1C}$ are independently an optionally substituted $C_6$-$C_{10}$ aryl, for example, substituted phenyl, unsubstituted phenyl, naphthyl, or unsubstituted naphthyl. In some embodiments of this paragraph, $R_1$ is —$NR_{1A}C(O)R_{1C}$, and $R_{1A}$ and $R_{1C}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, R$_1$ is —NR$_{1A}$C(O)R$_{1C}$, one of R$_{1A}$ and R$_{1C}$ is an optionally substituted C$_1$-C$_6$ alkyl and the other of R$_{1A}$ and R$_{1C}$ is an optionally substituted C$_6$-C$_{10}$ aryl or an optionally substituted 3 to 10 membered heterocyclyl. In some embodiments of this paragraph, R$_1$ is —NR$_{1A}$SO$_2$R$_{1C}$, and R$_{1A}$ and R$_{1C}$ are independently an optionally substituted C$_1$-C$_6$ alkyl, for example, methyl, ethyl, propyl, isopropyl, butyl, sec-buty, t-butyl, benzyl, or substituted benzyl. In some embodiments of this paragraph, R$_1$ is —NR$_{1A}$SO$_2$R$_{1C}$, and R$_{1A}$ and R$_{1C}$ are independently an optionally substituted C$_3$-C$_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, R$_1$ is —NR$_{1A}$SO$_2$R$_{1C}$, and R$_{1A}$ and R$_{1C}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, R$_1$ is —NR$_{1A}$SO$_2$R$_{1C}$, and R$_{1A}$ and R$_{1C}$ are independently an optionally substituted C$_6$-C$_{10}$ aryl, for example, substituted phenyl, unsubstituted phenyl, naphthyl, or unsubstituted naphthyl. In some embodiments of this paragraph, R$_1$ is —NR$_{1A}$SO$_2$R$_{1C}$, and R$_{1A}$ and R$_{1C}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, R$_1$ is —NR$_{1A}$SO$_2$R$_{1C}$, one of R$_{1A}$ and R$_{1C}$ is an optionally substituted C$_1$-C$_6$ alkyl and the other of R$_{1A}$ and R$_{1C}$ is an optionally substituted C$_6$-C$_{10}$ aryl or an optionally substituted 3 to 10 membered heterocyclyl.

In some embodiments, the compound of Formula (II) is selected from:

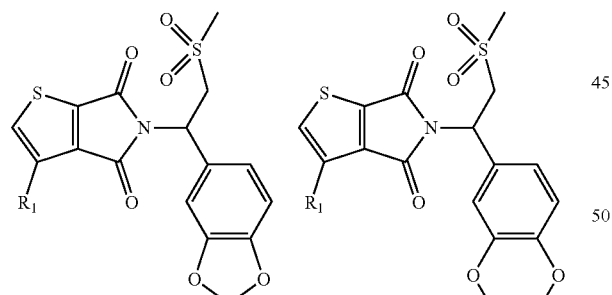

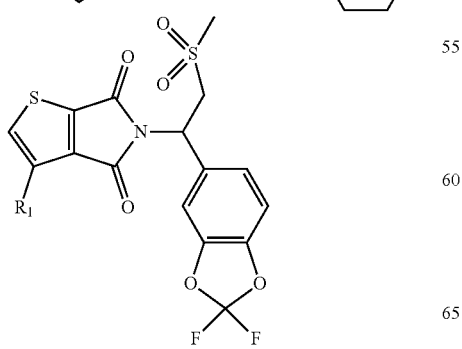

-continued

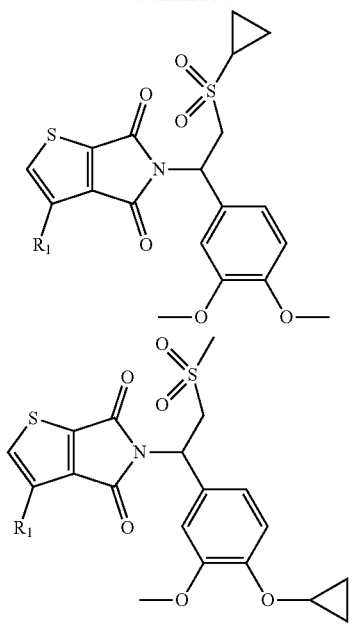

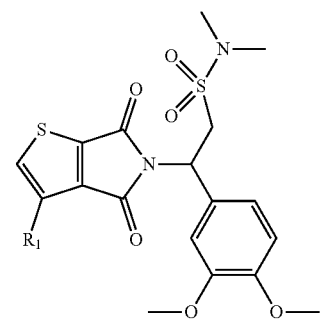

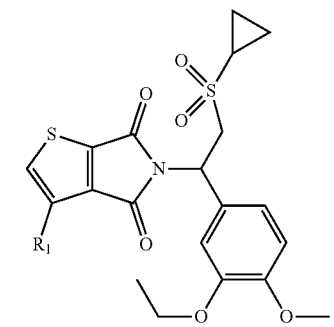

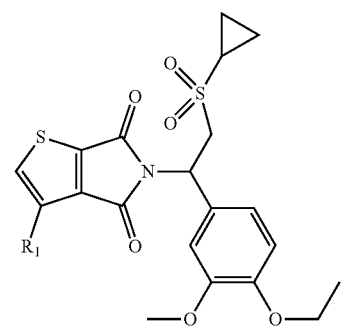

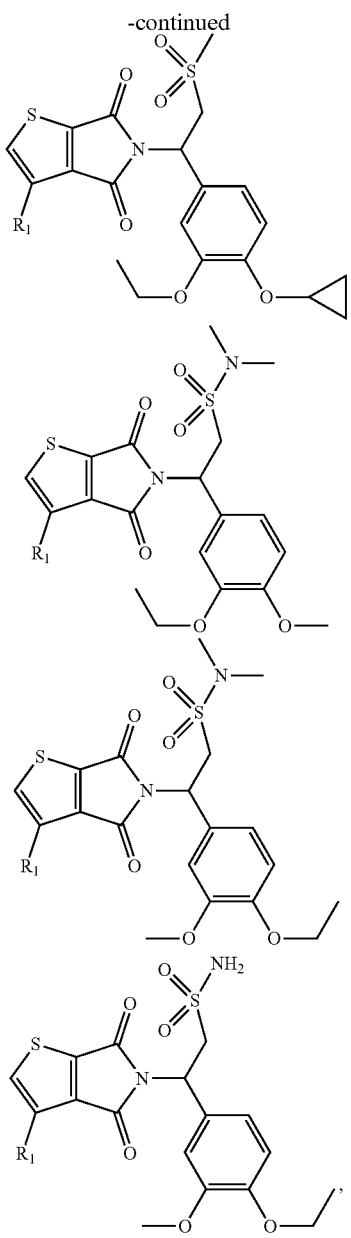

or a pharmaceutically acceptable salt of any of the foregoing. In some embodiments of this paragraph, $R_1$ is H, deuterium, hydroxy, halogen, nitro, cyano, optionally substituted $C_1$-$C_6$ alkoxy, —$NH_2$, —$NHR_{1A}$, —$NR_{1A}R_{1B}$, —$NHC(O)R_{1C}$, —$NR_{1A}C(O)R_{1C}$, —$NHSO_2R_{1C}$, —$NR_{1A}SO_2R_{1C}$, —$N[C(O)R_{1A}][C(O)R_{1C}]$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_{1A}$, $R_{1B}$, and $R_{1C}$ are independently selected from an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl. In some embodiments of this paragraph, $R_1$ is H. In some embodiments of this paragraph, $R_1$ is hydroxy. In some embodiments of this paragraph, $R_1$ is nitro. In some embodiments of this paragraph, $R_1$ is cyano. In some embodiments of this paragraph, $R_1$ is halogen, for example, fluoro, chloro, or bromo. In some embodiments of this paragraph, $R_1$ is optionally substituted $C_1$-$C_6$ alkoxy, for example, methoxy, ethoxy, propoxy, isopropoxy, butoxy, sec-butoxy, t-butoxy, —$OCF_3$, or —$OCD_3$. In some embodiments of this paragraph, $R_1$ is an optionally substituted $C_1$-$C_6$ alkyl, for example, methyl, ethyl, propyl, isopropyl, butyl, sec-buty, t-butyl, —$CF_3$, —$CH_2F$, —$CF_2H$, —$CD_3$, —$C(CH_3)_2CF_3$, benzyl, or substituted benzyl In some embodiments of this paragraph, $R_1$ is —$NH_2$. In some embodiments of this paragraph, $R_1$ is an optionally substituted $C_3$-$C_6$ cycloalkyl, for example, cyclopropyl, cyclobutyl, cyclopentyl, cyclohexyl, 2,2-difluorocyclopropyl, or 2,2-difluorocyclobutyl. In some embodiments of this paragraph, $R_1$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is an optionally substituted $C_6$-$C_{10}$ aryl, for example, substituted phenyl, unsubstituted phenyl, naphthyl, or unsubstituted naphthyl. In some embodiments of this paragraph, $R_1$ is optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NHR_{1A}$, and $R_{1A}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHR_{1A}$, and $R_{1A}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NHR_{1A}$, and $R_{1A}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHR_{1A}$, and $R_{1A}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHR_{1A}$, and $R_{1A}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}R_{1B}$, and $R_{1A}$ and $R_{1B}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NR_{1A}R_{1B}$, and $R_{1A}$ and $R_{1B}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NR_{1A}R_{1B}$, and $R_{1A}$ and $R_{1B}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NR_{1A}R_{1B}$, and $R_{1A}$ and $R_{1B}$ are independently an optionally substituted $C_6$-$C_{10}$ aryl, for example, substituted phenyl, unsubstituted phenyl, naphthyl, or unsubstituted naphthyl. In some embodiments of this paragraph, $R_1$ is —$NR_{1A}R_{1B}$, and $R_{1A}$ and $R_{1B}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}R_{1B}$, one of $R_{1A}$ and $R_{1B}$ is an optionally substituted $C_1$-$C_6$ alkyl and the other of $R_{1A}$ and $R_{1B}$ is an optionally substituted $C_6$-$C_{10}$ aryl or an optionally substituted 3 to 10 membered heterocyclyl. In some embodiments of this paragraph, $R_1$ is —$NHC(O)R_{1C}$, and $R_{1C}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHC(O)R_{1C}$, and $R_{1C}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NHC(O)R_{1C}$, and $R_{1C}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHC(O)R_{1C}$, and $R_{1C}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHC(O)R_{1C}$, and $R_{1C}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$N[C(O)R_{1A}][C(O)R_{1C}]$, and $R_{1A}$ and $R_{1C}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHSO_2R_{1C}$, and $R_{1C}$ is an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NHSO_2R_{1C}$, and $R_{1C}$ is an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NHSO_2R_{1C}$, and $R_{1C}$ is an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NHSO_2R_{1C}$, and $R_{1C}$ is an optionally substituted $C_6$-$C_{10}$ aryl, for example, substituted phenyl, unsubstituted phenyl, naphthyl, or unsubstituted naphthyl. In some embodiments of this paragraph, $R_1$ is —$NHSO_2R_{1C}$, and $R_{1C}$ is an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}C(O)R_{1C}$, and $R_{1A}$ and $R_{1C}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NR_{1A}C(O)R_{1C}$, and $R_{1A}$ and $R_{1C}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NR_{1A}C(O)R_{1C}$, and $R_{1A}$ and $R_{1C}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NR_{1A}C(O)R_{1C}$, and $R_{1A}$ and $R_{1C}$ are independently an optionally substituted $C_6$-$C_{10}$ aryl, for example, substituted phenyl, unsubstituted phenyl, naphthyl, or unsubstituted naphthyl. In some embodiments of this paragraph, $R_1$ is —$NR_{1A}C(O)R_{1C}$, and $R_{1A}$ and $R_{1C}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}C(O)R_{1C}$, one of $R_{1A}$ and $R_{1C}$ is an optionally substituted $C_1$-$C_6$ alkyl and the other of $R_{1A}$ and $R_{1C}$ is an optionally substituted $C_6$-$C_{10}$ aryl or an optionally substituted 3 to 10 membered heterocyclyl. In some embodiments of this paragraph, $R_1$ is —$NR_{1A}SO_2R_{1C}$, and $R_{1A}$ and $R_{1C}$ are independently an optionally substituted $C_1$-$C_6$ alkyl, for example, methyl, ethyl, propyl, isopropyl, butyl, sec-buty, t-butyl, benzyl, or substituted benzyl. In some embodiments of this paragraph, $R_1$ is —$NR_{1A}SO_2R_{1C}$, and $R_{1A}$ and $R_{1C}$ are independently an optionally substituted $C_3$-$C_6$ cycloalkyl, cyclopropyl, cyclobutyl, cyclopentyl, cyclohexyl, 2,2-difluorocyclopropyl, or 2,2-difluorocyclobutyl. In some embodiments of this paragraph, $R_1$ is —$NR_{1A}SO_2R_{1C}$, and $R_{1A}$ and $R_{1C}$ are independently an optionally substituted 3 to 10 membered heterocyclyl, for example, oxetane, azetidine, pyrrolidine, tetrahydrofuran, imidazoline, pyrazolidine, oxazolidine, isoxazolidine, thiazolidine, isothiazolidine, dioxolane, piperidine, tetrahydropyran, piperazine, morpholine, dioxane. In some embodiments of this paragraph, $R_1$ is —$NR_{1A}SO_2R_{1C}$, and $R_{1A}$ and $R_{1C}$ are independently an optionally substituted $C_6$-$C_{10}$ aryl, for example, substituted phenyl, unsubstituted phenyl, naphthyl, or unsubstituted naphthyl. In some embodiments of this paragraph, $R_1$ is —$NR_{1A}SO_2R_{1C}$, and $R_{1A}$ and $R_{1C}$ are independently an optionally substituted 5 to 10 membered heteroaryl, for example, substituted or unsubstituted furan, furazan, pyrrole, oxazole, benzoxazole, imidazole, benzimidazole, indole, indazole, pyrazole, benzopyrazole, isoxazole, benzoisoxazole, triazole, benzotriazole, thiadiazole, tetrazole, pyridine, pyridazine, pyrimidine, pyrazine, quinoline, isoquinoline, quinazoline, quinoxaline, cinnoline, or triazine. In some embodiments of this paragraph, $R_1$ is —$NR_{1A}SO_2R_{1C}$, one of $R_{1A}$ and $R_{1C}$ is an optionally substituted $C_1$-$C_6$ alkyl and the other of $R_{1A}$ and $R_{1C}$ is an optionally substituted $C_6$-$C_{10}$ aryl or an optionally substituted 3 to 10 membered heterocyclyl.

In some embodiments, the compound is a pharmaceutically acceptable salt.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or optic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

In some embodiments, the pharmaceutical composition is formulated as a gel, salve, ointment, cream, emulsion, or paste for topical application to the skin.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Some embodiments provide a method of treating, ameliorating, or preventing a disease, disorder, or condition associated with PDE4, comprising administering a therapeutically effective amount of a compound of any one of Formula (I), Formula (II), or a pharmaceutically acceptable salt of any of the foregoing, or a composition comprising any one of Formula (I) or Formula (II) to a subject in need thereof.

In some embodiments, the disease, disorder, or condition is selected from the group consisting of arthritis, ankylosing spondylitis, osteoarthritis, rheumatoid arthritis, Behcet's disease, inflammatory bowel diseases (e.g., Crohn's disease and ulcerative colitis), psoriasis, psoriatic arthritis, atopic dermatitis, contact dermatitis, and combinations thereof. In some embodiments, the disease, disorder, or condition is arthritis. In some embodiments, the disease, disorder, or condition is ankylosing spondylitis. In some embodiments, the disease, disorder, or condition is osteoarthritis. In some embodiments, the disease, disorder, or condition is rheumatoid arthritis. In some embodiments, the disease, disorder, or condition is Behcet's disease. In some embodiments, the disease, disorder, or condition is Crohn's disease. In some embodiments, the disease, disorder, or condition is ulcerative colitis. In some embodiments, the disease, disorder, or condition is psoriasis. In some embodiments, the disease, disorder, or condition is psoriatic arthritis. In some embodiments, the disease, disorder, or condition is atopic dermatitis. In some embodiments, the disease, disorder, or condition is contact dermatitis. In some embodiments, the disease, disorder, or condition is selected from two of arthritis, ankylosing spondylitis, osteoarthritis, rheumatoid arthritis, Behcet's disease, inflammatory bowel diseases (e.g., Crohn's disease and ulcerative colitis), psoriasis, psoriatic arthritis, atopic dermatitis, and contact dermatitis.

In some embodiments, the compound or composition is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-inflammatory agent or an immunosuppressive agent.

Some embodiments provide a method of decreasing expression of a protein selected from TNF-α, INF-γ, IL-2, IL-17, IL-23, or a combination thereof, comprising contacting a cell with a compound of any one of Formula (I) or Formula (II), or a pharmaceutically acceptable salt of any of the foregoing. In some embodiments, the protein is TNF-α. Some embodiments provide a method of decreasing expression of TNF-α. Some embodiments provide a method of decreasing expression of INF-γ. Some embodiments provide a method of decreasing expression of IL-2. Some embodiments provide a method of decreasing expression of IL-17. Some embodiments provide a method of decreasing expression of IL-23. Some embodiments provide a method of decreasing expression of two proteins selected from TNF-α, INF-γ, IL-2, IL-17, and IL-23. Some embodiments provide a method of decreasing expression of three proteins selected from TNF-α, INF-γ, IL-2, IL-17, and IL-23. Some embodiments provide a method of decreasing expression of four proteins selected from TNF-α, INF-γ, IL-2, IL-17, and IL-23. Some embodiments provide a method of decreasing expression of TNF-α, INF-γ, IL-2, IL-17, and IL-23.

In some embodiments, protein expression is decreased by about 10% to about 90%, about 5% to about 25%, about 20% to about 40%, about 35% to about 55%, about 50% to about 75%, about 70% to about 90%, or any value in between. In some embodiments, protein expression is decreased by about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or any value in between.

Some embodiments provide a method of inhibiting PDE4 activity, comprising contacting a cell with a compound of any one of Formula (I) or Formula (II), or a pharmaceutically acceptable salt of any of the foregoing. In some embodiments, PDE4 activity is decreased by about 10% to about 90%, about 5% to about 25%, about 20% to about 40%, about 35% to about 55%, about 50% to about 75%, about 70% to about 90%, or any value in between. In some embodiments, protein expression is decreased by about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 74%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or any value in between.

Some embodiments provide a method of treating psoriasis, comprising topically administering a therapeutically effective amount of a composition comprising any one of Formula (I) or Formula (II), or a pharmaceutically acceptable salt of any of the foregoing, to a subject in need thereof.

In some embodiments, the subject is known to possess wild-type PDE4. In some embodiments, the subject is known to possess wild-type TNF-α. In some embodiments, the subject is known to possess wild-type INF-γ, IL-2, IL-17, or IL-23. In some embodiments, the subject is known to possess aberrant PDE4. In some embodiments, the subject is known to possess aberrant TNF-α. In some embodiments, the subject is known to possess aberrant INF-γ, IL-2, IL-17, or IL-23.

In some embodiments, the cell is known to possess wild-type PDE4. In some embodiments, the cell is known to possess wild-type TNF-α. In some embodiments, the cell is known to possess wild-type INF-γ, IL-2, IL-17, or IL-23. In some embodiments, the cell is known to possess aberrant PDE4. In some embodiments, the cell is known to possess aberrant TNF-α. In some embodiments, the cell is known to possess aberrant INF-γ, IL-2, IL-17, or IL-23.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Additional Therapeutic Agents

Some embodiments provide pharmaceutical compositions comprising a compound of Formula (I) or Formula (II), and a pharmaceutically acceptable carrier. Some embodiments provide pharmaceutical compositions comprising of Formula (I) or Formula (II) a pharmaceutically acceptable carrier, and a second therapeutic agent.

In some embodiments, the second therapeutic agent is anti-inflammatory agent. In some embodiments, the second therapeutic agent is a non-steroidal anti-inflammatory agent. In some embodiments, the second therapeutic agent is anti-cancer agent. In some embodiments, the second therapeutic agent is an immunostimulatory agent. In some embodiments, the second therapeutic agent is an immunosuppressive agent. In some embodiments, the second therapeutic agent is antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

Dosing Regimes

In some embodiments, about 1 mg to about 5 grams; 2 mg to 2 gram; 5 mg to about 1 gram; 10 mg to about 800 mg; 20 mg to 600 mg; 30 mg to 400 mg; 40 mg to 200 mg; 50 mg to 100 mg of a compound of Formula (I), Formula (II), or any amount in between, is administered each day. In some embodiments, about 1 mg to about 5 grams; 2 mg to 2 gram;

5 mg to about 1 gram; 10 mg to about 800 mg; 20 mg to 600 mg; 30 mg to 400 mg; 40 mg to 200 mg; 50 mg to 100 mg of a compound of Formula (I), Formula (II), or any amount in between, is administered each week. In some embodiments, about 1 mg to about 5 grams; 2 mg to 2 gram; 5 mg to about 1 gram; 10 mg to about 800 mg; 20 mg to 600 mg; 30 mg to 400 mg; 40 mg to 200 mg; 50 mg to 100 mg of a compound of Formula (I), Formula (II), or any amount in between, is administered each cycle of treatment.

In some embodiments, a compound of Formula (I) or Formula (II) is administered at least once per day, at least twice per day, at least three times per day, or at least four times per day. In some embodiments, a compound of Formula (I) or Formula (II) is administered at least once per day, at least twice per day, at least three times per day, or at least four times per week. In some embodiments, each cycle of treatment lasts 1, 2, 3, 4, 5, 6, 7, 8, 9, 10, 11, 12, 13, or 14 days, or any value in between. In some embodiments, each cycle of treatment has at least 1, 2, 3, 4, 5, 6, or 7 days between administrations of a compound of Formula (I), Formula (II), or any value in between.

In some embodiments, a compound of Formula (I) or Formula (II) is provided intravenously over about 10, 20, 30, 40, 50, 60, 90, 120, 150, 180, 210, or 240 minutes, or any value in between.

EXAMPLES

Additional embodiments are disclosed in further detail in the following examples, which are not in any way intended to limit the scope of the claims.

Characterization of the compounds disclosed herein was performed with Bruker AV-500 and Bruker DRX-500 NMR spectrometers and a Perkin Elmer PE-SCIEX API-150 mass spectrometer.

Synthesis

Scheme 1

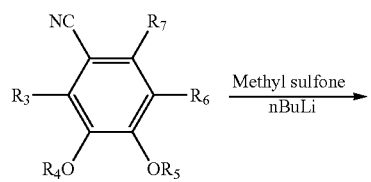

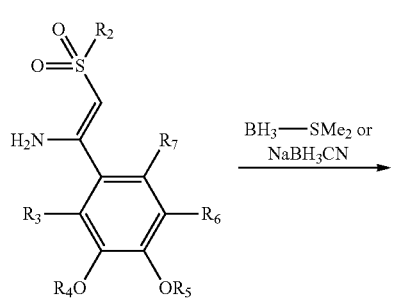

Scheme 2: Compounds of Formula I

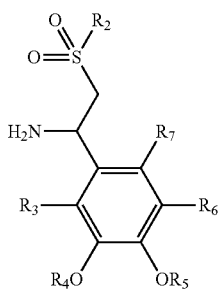

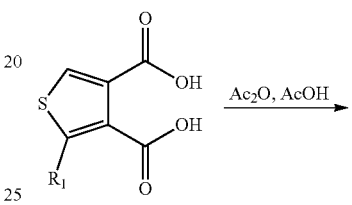

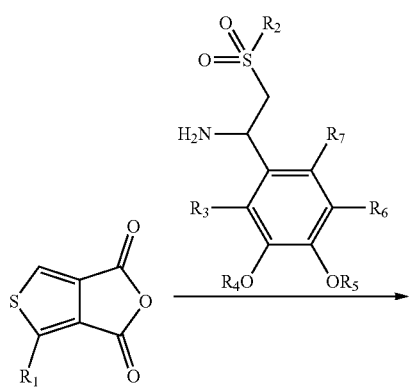

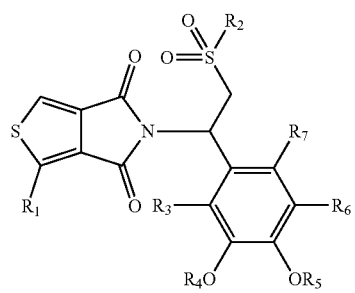

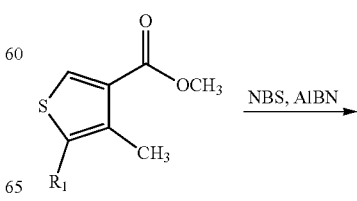

57
-continued
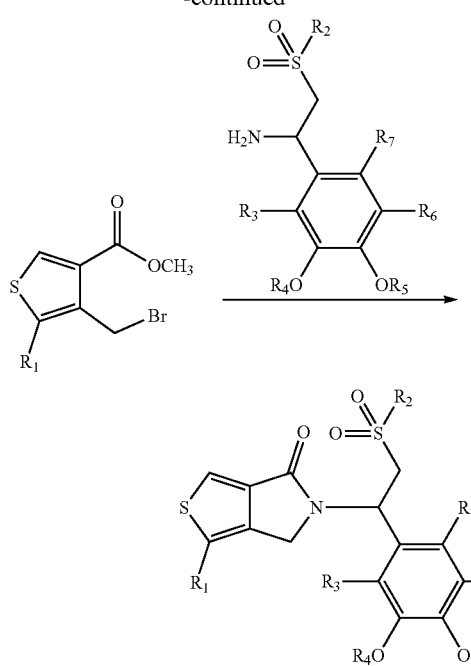
Scheme 3: Compounds of Formula II
58
-continued
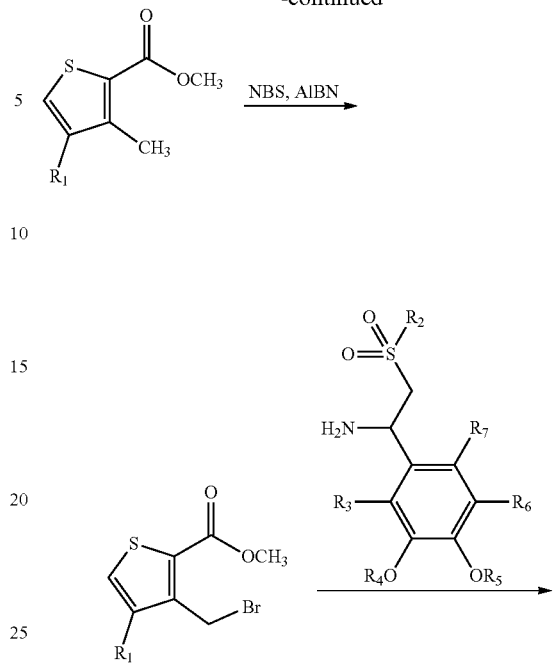
Example 1: Compound 1: (S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)acetamide
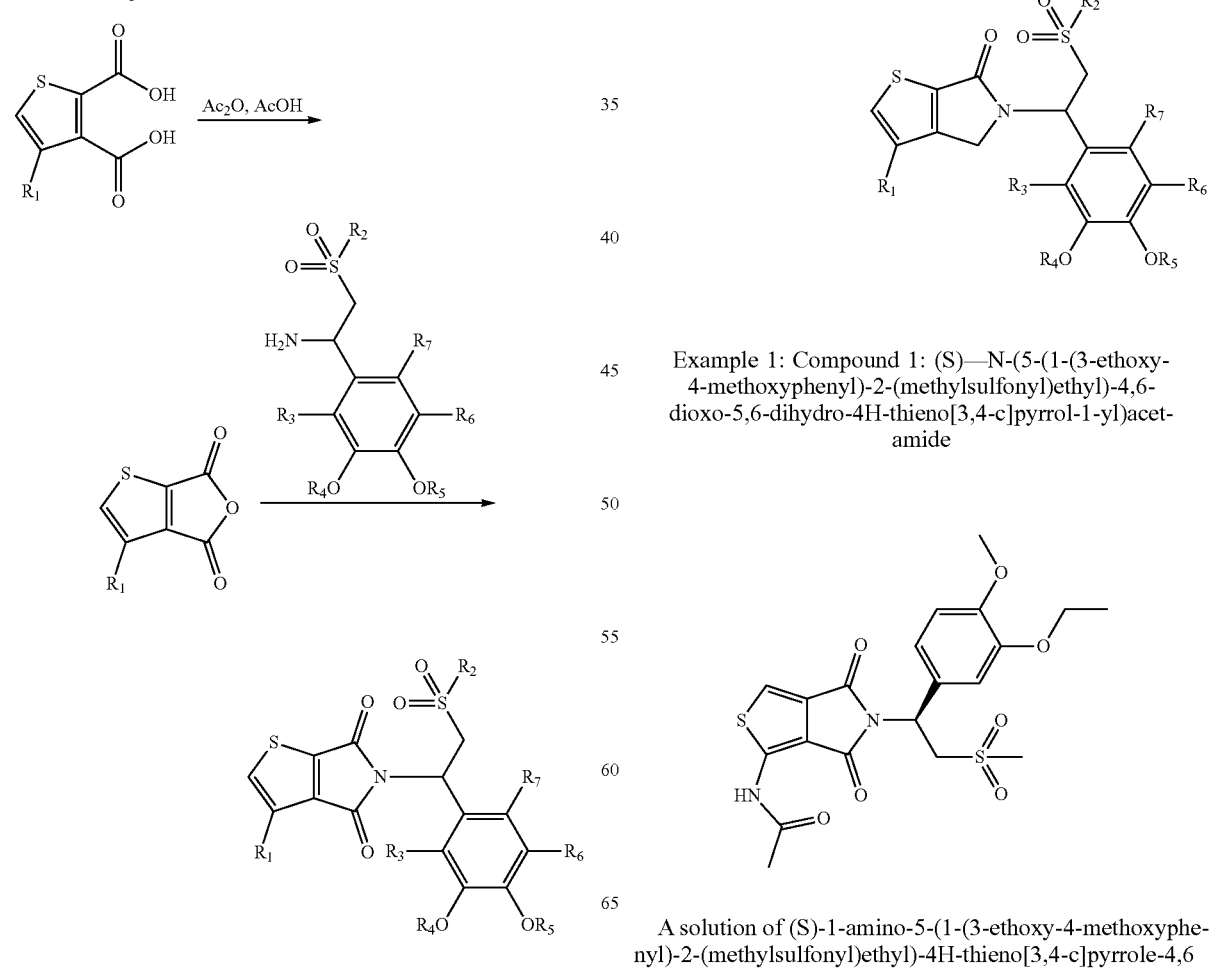
A solution of (S)-1-amino-5-(1-(3-ethoxy-4-methoxyphenyl)-2-(methylsulfonyl)ethyl)-4H-thieno[3,4-c]pyrrole-4,6

(5H)-dione (40 mg, 0.094 mmol) in pyridine (4 mL) was cooled to 0° C. then acetyl chloride (0.15 mL in 1 mL DCM) was added. The mixture was stirred at 0° C. for 0.5 h. HCl (2 M, 3 mL) was added and the organic layer was separated, washed with brine, dried over Na$_2$SO$_4$, concentrated, and purified on silica gel (ethyl acetate (EA)/petroleum ether (PE) 40%-70%) to give the title compound (25.0 mg, 57%) as a white solid. MS (ESI) m/z 467.0 [M+H]$^+$. $^1$H NMR (400 MHz, CDCl$_3$) δ 9.42 (s, 1H), 7.23 (s, 1H), 7.00-6.98 (m, 2H), 6.74 (d, J=8.0 Hz, 1H), 5.76-5.73 (m, 1H), 4.52-4.45 (m, 1H), 4.04-3.99 (m, 2H), 3.77 (s, 3H), 3.70-3.66 (m, 1H), 2.80 (s, 3H), 2.21 (s, 3H), 1.40-1.36 (m, 3H).

Example 2: Compound 2: (S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)pivalamide

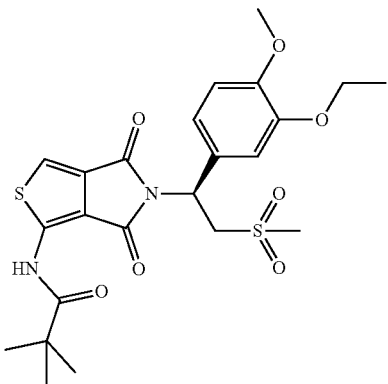 [SMILES: CCOc1cc([C@@H](CS(C)(=O)=O)N2C(=O)c3csc(NC(=O)C(C)(C)C)c3C2=O)ccc1OC]

To a solution of (S)-5-(1-(3-ethoxy-4-methoxyphenyl)-2-(methylsulfonyl) ethyl)-1-nitro-4H-thieno[3,4-c]pyrrole-4,6(5H)-dione (400 mg, 0.88 mmol) in THF (10 mL) was added Pd/C (200 mg). The mixture stirred at RT under hydrogen overnight, then filtered, concentrated, and purified on silica gel to give (S)-1-amino-5-(1-(3-ethoxy-4-methoxyphenyl)-2-(methylsulfonyl)ethyl)-4H-thieno[3,4-c] pyrrole-4,6(5H)-dione (281 mg, 75%) as a yellow solid.

To a solution of (S)-1-amino-5-(1-(3-ethoxy-4-methoxyphenyl)-2-(methylsulfonyl)ethyl)-4H-thieno[3,4-c]pyrrole-4,6(5H)-dione (100 mg, 0.236 mmol) in pyridine (5 mL) was added pivaloyl chloride (56 mg, 0.47 mmol) at 0° C. The mixture was stirred at RT for 4 h, diluted with water then extracted with EA. The combined organic layers were washed with HCl (1N), dried over Na$_2$SO$_4$, filtered, concentrated, and purified on silica gel eluting with EA/PE from 40% to 70% to give the title compound (21.0 mg, 17.5%) as a white solid. MS (ESI) m/z=509.1 [M+H]$^+$. $^1$H NMR (DMSO-d6, 400 MHz) δ 11.52 (s, 1H), 7.81 (s, 1H), 7.04 (s, 1H), 6.93 (s, 2H), 5.74 (d, J=8.8 Hz, 1H), 4.40-4.33 (m, 1H), 4.09 (d, J=12.0 Hz, 1H), 4.01 (d, J=6.8 Hz, 2H), 3.73 (s, 3H), 3.02 (s, 3H), 1.36-1.21 (m, 12H).

Example 3: Compound 3: (S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)-2-methoxyacetamide

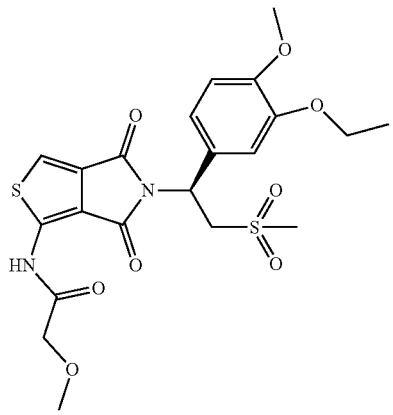 [SMILES: CCOc1cc([C@@H](CS(C)(=O)=O)N2C(=O)c3csc(NC(=O)COC)c3C2=O)ccc1OC]

To a cooled (0° C.) solution of (S)-1-amino-5-(1-(3-ethoxy-4-methoxyphenyl)-2-(methylsulfonyl)ethyl)-4H-thieno[3,4-c]pyrrole-4,6(5H)-dione (40 mg, 0.094 mmol) in pyridine (3 mL) was added 2-methoxyacetyl chloride (0.1 mL in 1 mL DCM). The mixture was stirred at 0° C. for 0.5 h. HCl (2M, 3 mL) was added and the organic layer was washed with brine, dried over Na$_2$SO$_4$, concentrated and purified on silica gel eluting with EA/PE from 40% to 70% to give the title compound (15 mg, 32%) as a white solid. MS (ESI) m/z 497.1 [M+H]$^+$. $^1$H NMR (400 MHz, CDCl$_3$) δ 9.77 (s, 1H), 7.36 (s, 1H), 7.10-7.08 (m, 2H), 6.83 (d, J=8.8 Hz, 1H), 5.81 (dd, J=4.8 Hz, 10.4 Hz, 1H), 4.56-4.50 (m, 1H), 4.14-4.08 (m, 4H), 3.85 (s, 3H), 3.73 (dd, J=3.6 Hz, 14.4 Hz, 1H), 3.55 (s, 3H), 2.85 (s, 3H), 1.47 (t, J=6.8 Hz, 3H).

Example 4: Compound 4: (S)—N-(cyclopropanecarbonyl)-N-(5-(1-(3-ethoxy-4-hydroxy phenyl)-2-(methylsulfonyl)ethyl)-4,6-dioxo-5,6-dihydro-4H-thieno[3,4-c]pyrrol-1-yl)cyclopropanecarboxamide

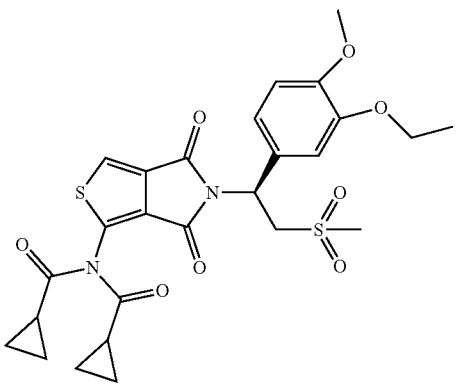 [SMILES: CCOc1cc([C@@H](CS(C)(=O)=O)N2C(=O)c3csc(N(C(=O)C4CC4)C(=O)C4CC4)c3C2=O)ccc1OC]

To a solution of (S)-1-amino-5-(1-(3-ethoxy-4-methoxyphenyl)-2-(methylsulfonyl)ethyl)-4H-thieno[3,4-c]pyrrole-4,6(5H)-dione (200 mg, 0.472 mmol) in pyridine (5 mL) was added cyclopropanecarbonyl chloride (171 mg, 1.416 mmol) at 0° C., and the mixture was stirred at RT overnight. The mixture was concentrated, diluted with water and extracted with EA. The combined organic layers were washed with HCl (1N) and dried over Na$_2$SO$_4$, filtered, concentrated, and purified by prep-TLC (PE/EA, 1:1) to give the title compound (60.7 mg, 61.4%) as a yellow solid. MS (ESI) m/z=578.2 [M+H$_2$O]$^+$. $^1$H NMR (400 MHz, DMSO-d6) δ 7.94 (s, 1H), 7.05 (s, 1H), 6.96-6.90 (m, 2H), 5.70 (dd, J=9.6, 4.4 Hz, 1H), 4.33-4.26 (m, 1H), 4.14-4.08 (m, 1H), 4.04-3.98 (m, 2H), 3.74 (s, 3H), 2.99 (s, 3H), 2.20-2.17 (m, 1H), 2.06-2.03 (m, 1H), 1.32 (t, J=7.2 Hz, 3H), 1.23-1.20 (m, 2H), 1.09-1.04 (m, 4H), 0.98 (s, 2H).

Example 5: Compound 5: N-(5-((S)-1-(3-ethoxy-4-methoxyphenyl)-2-(methylsulfonyl)ethyl)-4,6-dioxo-5,6-dihydro-4H-thieno[3,4-c]pyrrol-1-yl)-3,3,3-trifluoro-2-methylpropanamide

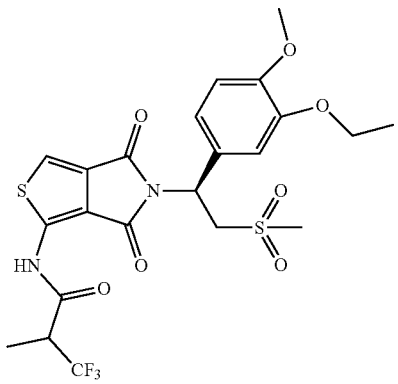 [SMILES: CCOc1cc([C@@H](CS(C)(=O)=O)N2C(=O)c3csc(NC(=O)C(C)C(F)(F)F)c3C2=O)ccc1OC]

To a solution of 3,3,3-trifluoro-2-methylpropanoic acid (34 mg, 0.24 mmol) in DMF (3 mL) was added 1-hydroxybenzotriazole (HOBt) (48 mg, 0.354 mmol) and 3-(ethyliminomethylideneamino)-N,N-dimethylpropan-1-amine hydrochloride (EDCI) (68 mg, 0.35 mmol), followed by DIEA (91 mg, 0.71 mmol). (S)-1-amino-5-(1-(3-ethoxy-4-methoxyphenyl)-2-(methylsulfonyl)ethyl)-4H-thieno[3,4-c]pyrrole-4,6(5H)-dione (100 mg, 0.236 mmol) was added and the solution was stirred at RT for 16 h, concentrated and purified on silica gel eluting with EA/PE from 40% to 70% to give the title compound (14.5 mg, 11%) as a white solid. MS (ESI) m/z 547.1 [M–H]$^+$. $^1$H NMR (400 MHz, DMSO-d6) δ 12.22 (s, 1H), 7.86 (s, 1H), 7.04 (s, 1H), 6.93 (s, 2H), 5.71 ((dd, J=4.0 Hz, 10.0 Hz, 1H), 4.35-4.28 (m, 1H), 4.13-4.09 (m, 2H), 4.02-3.97 (m, 2H), 3.73 (s, 3H), 3.01 (s, 3H), 1.37-1.30 (m, 6H).

Example 6: Compound 6: S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)-2-ethylbutanamide

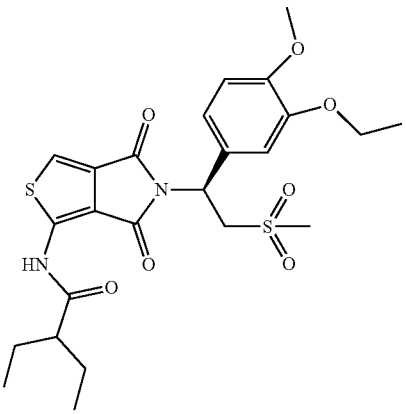 [SMILES: CCOc1cc([C@@H](CS(C)(=O)=O)N2C(=O)c3csc(NC(=O)C(CC)CC)c3C2=O)ccc1OC]

To a cooled (0 C) solution of (S)-1-amino-5-(1-(3-ethoxy-4-methoxyphenyl)-2-(methylsulfonyl)ethyl)-4H-thieno[3,4-c]pyrrole-4,6(5H)-dione (100 mg, 0.236 mmol) in pyridine (3 mL) was added 2-ethylbutanoyl chloride (0.15 mL in 1 mL DCM). After the mixture was stirred at 0 C for 0.5 h, HCl (2M, 3 mL) was added. The organic layer was washed with brine, dried over Na$_2$SO$_4$, concentrated, and purified on silica gel eluting with EA/PE from 40% to 70% to give the title compound (25.3 mg, 20%) as a white solid. MS (ESI) m/z 523.2 [M+H]$^+$. $^1$H NMR (400 MHz, DMSO-d6) δ 11.75 (s, 1H), 7.78 (s, 1H), 7.04 (s, 1H), 6.93 (s, 2H), 5.71 ((dd, J=4.4 Hz, 10.4 Hz, 1H), 4.36-4.29 (m, 1H), 4.11 ((dd, J=4.4 Hz, 14.8 Hz, 1H), 4.02-3.97 (m, 2H), 3.73 (s, 3H), 3.01 (s, 3H), 2.78-2.74 (m, 1H), 1.59-1.43 (m, 4H), 1.34-1.30 (m, 3H), 0.83-0.80 (m, 6H).

Example 7: Compound 7: (S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)-2,2,2-trifluoroacetamide

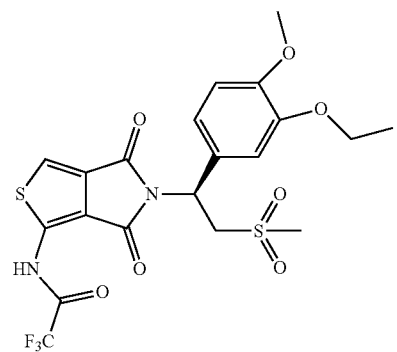 [SMILES: CCOc1cc([C@@H](CS(C)(=O)=O)N2C(=O)c3csc(NC(=O)C(F)(F)F)c3C2=O)ccc1OC]

A solution of thiophene-3,4-dicarboxylic acid (25.0 g, 145 mmol) in acetic anhydride (250 mL) was heated to 110° C. for 16 h. The mixture was then concentrated to give thieno[3,4-c]furan-1,3-dione (22.0 g crude) as a yellow solid and used for the next step without further purification.

Thieno[3,4-c]furan-1,3-dione (22.0 g, 143 mmol) was added to nitric acid (95%, 90 mL) at 0-5° C. over 1 h. The mixture was warmed to RT for 1 h then poured into ice water and extracted with EA. The combined organic layers were dried over Na₂SO₄, filtered and concentrated to give 2-nitrothiophene-3,4-dicarboxylic acid (20.8 g, 66%) as a yellow solid and used for the next step without further purification.

A solution of 2-nitrothiophene-3,4-dicarboxylic acid (6.0 g, 27.6 mmol) in Ac₂O (60 mL) was heated to 140° C. for 3 h. The mixture was concentrated to give 4-nitrothieno[3,4-c]furan-1,3-dione (5.5 g) as a yellow solid and used for the next step without further purification.

A mixture of 4-nitrothieno[3,4-c]furan-1,3-dione (5.5 g, 27.64 mmol), and (S)-1-(3-ethoxy-4-methoxyphenyl)-2-(methylsulfonyl)ethanamine (7.54 g, 27.64 mmol) in THF (250 mL) was stirred at RT for 16 h. Then 1,1'-carbonyldiimidazol (CDI) (5.37 g, 33.1 mmol) was added and the reaction was heated to reflux for 3 h. The mixture was concentrated and purified on silica gel eluting with EA/PE from 30% to 50% to give (S)-5-(1-(3-ethoxy-4-methoxyphenyl)-2-(methylsulfonyl)ethyl)-1-nitro-4H-thieno[3,4-c]pyrrole-4,6(5H)-dione (10.0 g, 79%) as a yellow solid.

A mixture of (S)-5-(1-(3-ethoxy-4-methoxyphenyl)-2-(methylsulfonyl) ethyl)-1-nitro-4H-thieno[3,4-c]pyrrole-4,6(5H)-dione (1.0 g, 2.2 mmol), NH₄Cl (706 mg, 13.2 mmol) and iron powder (740 mg, 13.2 mmol) in THF/water (50 mL/10 mL) was heated to reflux for 1 h. The reaction was filtered, concentrated, and to purified on silica gel eluting with EA/PE from 40% to 70% to give (S)-1-amino-5-(1-(3-ethoxy-4-methoxyphenyl)-2-(methylsulfonyl)ethyl)-4H-thieno[3,4-c] pyrrole-4,6(5H)-dione (300 mg, 32%) as a yellow solid. MS (ESI) m/z 424.9 [M+H]⁺.

To a solution of (S)-1-amino-5-(1-(3-ethoxy-4-methoxyphenyl)-2-(methylsulfonyl)ethyl)-4H-thieno[3,4-c]pyrrole-4,6(5H)-dione (150 mg, 0.354 mmol) in ACN (3 mL) was added pyridine (1 mL). The mixture was cooled to 0° C., then trifluoroacetic anhydride (0.2 mL in 1 mL ACN) was added at 0° C. for 0.5 h. HCl (2M, 3 mL) was added. The organic layer was washed with brine, dried over Na₂SO₄, concentrated and purified on silica gel eluting with EA/PE from 40% to 70% to give the title compound (30 mg, 16%) as a white solid. MS (ESI) m/z 538.1 [M+H₂O]⁺. ¹H NMR (400 MHz, DMSO-d6) δ 7.81 (s, 1H), 7.09 (s, 1H), 6.98 (s, 2H), 5.76-5.73 (m, 1H), 4.43-4.36 (m, 1H), 4.15-4.10 (m, 1H), 4.07-4.03 (m, 2H), 3.78 (s, 3H), 3.06 (s, 3H), 1.39-1.36 (m, 3H).

Example 8: Compound 8: (S)—N-(5-(1-(3-ethoxy-4-methoxyphenyl)-2-(methylsulfonyl)ethyl)-4,6-dioxo-5,6-dihydro-4H-thieno[3,4-c]pyrrol-1-yl)cyclopropanecarboxamide

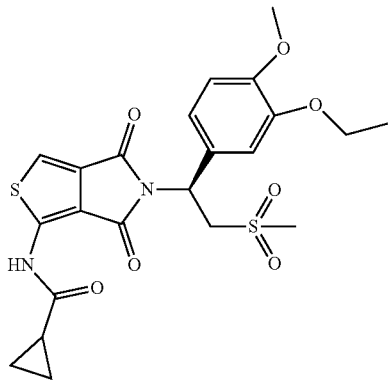 [SMILES: CCOc1cc([C@@H](CS(C)(=O)=O)N2C(=O)c3csc(NC(=O)C4CC4)c3C2=O)ccc1OC]

To a solution of cyclopropanecarboxylic acid (41 mg, 0.472 mmol) in DMF (5 mL) was added HOBt (95 mg, 0.71 mmol) and EDCI (136 mg, 0.71 mmol) followed by DIEA (183 mg, 1.5 mmol). (S)-1-amino-5-(1-(3-ethoxy-4-methoxyphenyl)-2-(methylsulfonyl)ethyl)-4H-thieno[3,4-c]pyrrole-4,6(5H)-dione (200 mg, 0.472 mmol) was added and the solution was stirred at RT for 16 h. The mixture was concentrated and purified on silica gel eluting with EA/PE from 40% to 70% to give the title compound (14 mg, 6%) as a yellow solid. MS (ESI) m/z 493.1 [M+H]⁺. ¹H NMR (400 MHz, DMSO-d6) δ 12.01 (s, 1H), 7.76 (s, 1H), 7.06 (s, 1H), 6.95 (s, 2H), 5.74-5.71 (m, 1H), 4.35-4.31 (m, 1H), 4.14-4.09 (m, 1H), 4.04-3.99 (m, 2H), 3.74 (s, 3H), 3.02 (s, 3H), 2.52-2.51 (m, 1H), 1.35-1.31 (m, 3H), 0.96-0.90 (m, 4H).

Example 9: Compound 9: (S)—N-(5-(1-(3-ethoxy-4-methoxyphenyl)-2-(methylsulfonyl)ethyl)-4,6-dioxo-5,6-dihydro-4H-thieno[2,3-c]pyrrol-3-yl)-2,2,2-trifluoroacetamide

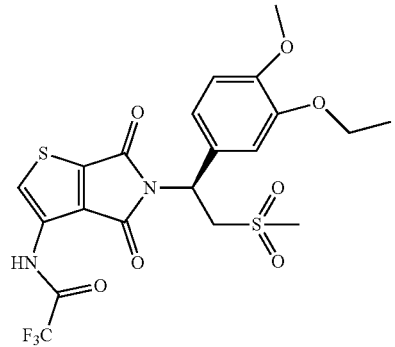 [SMILES: CCOc1cc([C@@H](CS(C)(=O)=O)N2C(=O)c3scc(NC(=O)C(F)(F)F)c3C2=O)ccc1OC]

To a solution of 4-bromothiophene-3-carboxylic acid (10.0 g, 48.35 mmol) in THF (100 mL) at RT was added hexamethylphosphoramide (1.75 g, 9.67 mmol). The mixture was cooled to −70° C. and lithium diisopropylamide (53 mL, 106.5 mmol, 2M in THF) was added under N₂. The reaction was stirred at this temperature for 1 h then CO₂ was bubbled for 30 min at −40° C. The reaction was warmed to RT and stirred for 15 min. The reaction was quenched with water (100 mL) and adjusted to pH=10 with 10% NaOH (aq.). The mixture was extracted with EA and the aqueous layer was adjusted to pH=3 with 1 N HCl, extracted with EA, dried over Na₂SO₄, filtered, concentrated, and washed with EA to give 4-bromothiophene-2,3-dicarboxylic acid (5.6 g, 46.2%) as a red solid.

4-Bromothiophene-2,3-dicarboxylic acid (1.0 g, 4 mmol) was dissolved in acetic anhydride (10 mL), and the suspension was stirred at 135° C. for 16 h. The solvent was removed and the residue was dried to give 3-bromothieno[2,3-c]furan-4,6-dione (1.0 g, crude) as a brown solid which was used directly for the next step.

To a solution of 3-bromothieno[2,3-c]furan-4,6-dione (900 mg, 3.88 mmol) in THF (15 mL) at RT was added (S)-1-(3-ethoxy-4-methoxyphenyl)-2-(methylsulfonyl)ethanamine (1.06 g, 3.88 mmol), and the mixture was stirred for 1 h. Then 1,1'-carbonyldiimidazole (754.9 mg, 4.66 mol) was added and the mixture was heated at 70° C. for 3 h. The reaction was concentrated and the residue was purified on silica gel eluting with EA/PE from 10% to 50% to give (S)-3-bromo-5-(1-(3-ethoxy-4-methoxyphenyl)-2-(methylsulfonyl)ethyl)-4H-thieno[2,3-c]pyrrole-4,6(5H)-dione (5) (1.52 g, 80%) as a yellow solid. MS (ESI) m/z 504.9, 506.9 [M+H$_2$O]$^+$.

To a suspension of (S)-3-bromo-5-(1-(3-ethoxy-4-methoxyphenyl)-2-(methylsulfonyl)ethyl)-4H-thieno[2,3-c]pyrrole-4,6(5H)-dione (500 mg, 1.03 mmol) in 1,4-dioxane/toluene (13 mL/13 mL) at RT was added diphenylmethanimine (223.4 mg, 1.23 mmol) and cesium carbonate (669.5 mg, 2.06 mmol). The suspension was degassed and purged with nitrogen twice. Then tris(dibenzylideneacetone)dipalladium (Pd$_2$(dba)$_3$) (188.6 mg, 0.206 mmol) and Xantphos (178.8 mg, 0.309 mmol) was added. The suspension was heated at 100° C. for 16 h. The mixture was cooled to RT and concentrated. The residue was purified on silica gel eluting with EA/PE from 10% to 50% to give (S)-3-((diphenyl methylene)amino)-5-(1-(3-ethoxy-4-methoxyphenyl)-2-(methylsulfonyl)ethyl)-4H-thieno[2,3-c]pyrrole-4,6(5H)-dione (241 mg, 39.8%) as a yellow solid. MS (ESI) m/z 589.1 [M+H]$^+$.

To a solution of (S)-3-((diphenylmethylene)amino)-5-(1-(3-ethoxy-4-methoxyphenyl)-2-(methylsulfonyl)ethyl)-4H-thieno[2,3-c]pyrrole-4,6(5H)-dione (240 mg, 0.408 mmol) in MeOH (10 mL) at RT was added NH$_2$OH.HCl (113.4 mg, 1.632 mmol) and NaOAc (167 mg, 2.04 mmol). The suspension was stirred at RT for 5 h then concentrated. The residue was purified on silica gel eluting with EA/PE from 10% to 50% to give (S)-3-amino-5-(1-(3-ethoxy-4-methoxyphenyl)-2-(methylsulfonyl)ethyl)-4H-thieno[2,3-c]pyrrole-4,6(5H)-dione (83 mg, 48%) as a yellow gum. MS (ESI) m/z 424.9 [M+H]$^+$.

To a solution of (S)-3-amino-5-(1-(3-ethoxy-4-methoxyphenyl)-2-(methylsulfonyl)ethyl)-4H-thieno[2,3-c]pyrrole-4,6(5H)-dione (83 mg, 0.196 mmol) in DCM/pyridine (2 mL/2 mL) at 0° C. was added the solution of trifluoroacetic anhydride (123 mg, 0.587 mmol) in DCM (0.5 mL). The reaction was stirred at 0° C. for 10 min, quenched with water (1 mL) and extracted with DCM. The combined organic layers were washed with 1N HCl, dried over Na$_2$SO$_4$, filtered, concentrated, and purified by prep-TLC (PE/EA, 1:1) to give the title compound (54.5 mg, 53.5%) as a yellow solid. MS (ESI) m/z 521.1 [M+H]$^+$. $^1$H NMR (400 MHz, DMSO-d6) δ 11.71 (s, 1H), 8.18 (s, 1H), 7.05 (s, 1H), 6.95 (s, 2H), 5.67 (dd, J=4.0, 10.4 Hz, 1H), 4.29 (dd, J=10.0, 14.0 Hz, 1H), 4.10 (dd, J=4.4, 14.0 Hz, 1H), 4.01 (q, J=7.2 Hz, 2H), 3.74 (s, 3H), 3.00 (s, 3H), 1.32 (t, J=6.8 Hz, 3H).

Example 10: Compound 10: (S)—N-(5-(1-(3-ethoxy-4-methoxyphenyl)-2-(methylsulfonyl) ethyl)-4,6-dioxo-5,6-dihydro-4H-thieno[2,3-c]pyrrol-3-yl)-2-methoxyacetamide

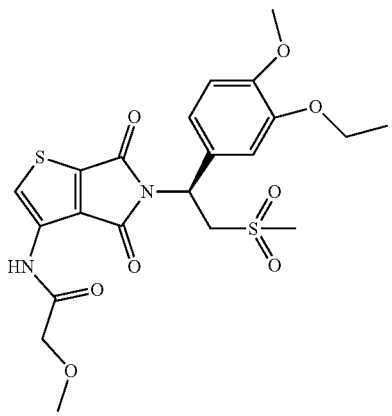 [SMILES: CCOc1cc([C@@H](CS(C)(=O)=O)N2C(=O)c3scc(NC(=O)COC)c3C2=O)ccc1OC]

To a solution of (S)-3-amino-5-(1-(3-ethoxy-4-methoxyphenyl)-2-(methylsulfonyl)ethyl)-4H-thieno[2,3-c]pyrrole-4,6(5H)-dione (73 mg, 0.172 mmol) in DCM/pyridine (2 mL/2 mL) at 0° C. was added the solution of 2-methoxyacetyl chloride (37 mg, 0.344 mmol) in DCM (0.5 mL). The reaction was stirred at 0° C. for 10 min and quenched with water (1 mL) then extracted with DCM. The combined organic layers were washed with 1 N HCl, dried over Na$_2$SO$_4$, filtered, concentrated, and purified by prep-TLC (PE/EA, 1:1) to give the title compound (30.3 mg, 35.6%) as a light yellow solid. MS (ESI) m/z 497.1 [M+H]$^+$. $^1$H NMR (400 MHz, DMSO-d6) δ 9.55 (s, 1H), 8.31 (s, 1H), 7.04 (d, J=1.6 Hz, 1H), 6.98-6.92 (m, 2H), 5.67 (dd, J=4.0, 10.4 Hz, 1H), 4.28 (dd, J=11.2, 14.4 Hz, 1H), 4.10 (dd, J=4.4, 14.0 Hz, 1H), 4.09 (s, 2H), 4.01 (q, J=6.8 Hz, 2H), 3.74 (s, 3H), 3.41 (s, 3H), 3.01 (s, 3H), 1.32 (t, J=6.8 Hz, 3H).

Example 11: Compound 11: (S)—N-(5-(1-(3-ethoxy-4-methoxyphenyl)-2-(methylsulfonyl) ethyl)-4,6-dioxo-5,6-dihydro-4H-thieno[2,3-c]pyrrol-3-yl) cyclopropanecarboxamide

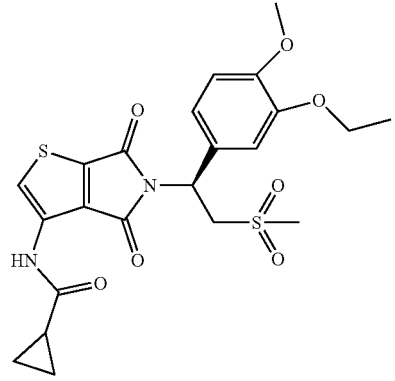 [SMILES: CCOc1cc([C@@H](CS(C)(=O)=O)N2C(=O)c3scc(NC(=O)C4CC4)c3C2=O)ccc1OC]

To a solution of cyclopropanecarboxylic acid (533 mg, 6.19 mmol) in DCM (5 mL) at 0° C. was added a solution of oxalyl chloride (1.17 g, 9.28 mmol) in DCM (1 mL). The reaction was stirred at 20° C. for 3 h then concentrated to give cyclopropanecarbonyl chloride (500 mg, crude) as a yellow oil. To a solution of (S)-3-amino-5-(1-(3-ethoxy-4-methoxyphenyl)-2-(methylsulfonyl)ethyl)-4H-thieno[2,3-c]pyrrole-4,6(5H)-dione (37 mg, 0.087 mmol) in DCM/pyridine (2 mL/2 mL) at 0° C. was added a solution of cyclopropanecarbonyl chloride (10.5 mg, 0.131 mmol) in DCM (0.5 mL). The reaction was stirred at 0° C. for 10 minutes, quenched with water (1 mL) and extracted with DCM. The combined organic layers were washed with 1 N HCl, dried over Na$_2$SO$_4$, filtered, concentrated, and purified by prep-TLC (PE/EA, 1:1.5) to give the title compound (46.9 mg, 64%) as a light yellow solid. MS (ESI) m/z 493.1, 510.1 [M+H, M+H$_2$O]$^+$. $^1$H NMR (400 MHz, DMSO-d6) δ 10.36 (s, 1H), 8.26 (s, 1H), 7.06 (s, 1H), 6.99-6.924 (m, 2H), 5.71 (dd, J=4.0, 10.4 Hz, 1H), 4.30 (dd, J=11.2, 14.4 Hz, 1H), 4.11 (dd, J=4.4, 14.4 Hz, 1H), 4.02 (q, J=6.8 Hz, 2H), 3.75 (s, 3H), 3.03 (s, 3H), 2.09 (t, J=6.0 Hz, 1H), 1.33 (t, J=6.8 Hz, 3H), 0.83 (d, J=6.4 Hz, 2H).

Example 12: Compound 12 (S) and Compound 18 (R): N-(5-(1-(benzo[d][1,3]dioxol-5-yl)-2-(methylsulfonyl)ethyl)-4,6-dioxo-5,6-dihydro-4H-thieno[3,4-c]pyrrol-1-yl)acetamide Example 13: Compound 13 (S) and Compound 19 (R): N-(5-(1-(benzo[d][1,3]dioxol-5-yl)-2-(methylsulfonyl)ethyl)-4,6-dioxo-5,6-dihydro-4H-thieno[3,4-c]pyrrol-1-yl)cyclopropane carboxamide

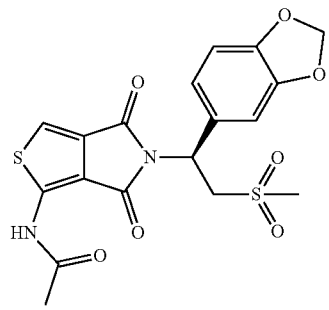

(12)

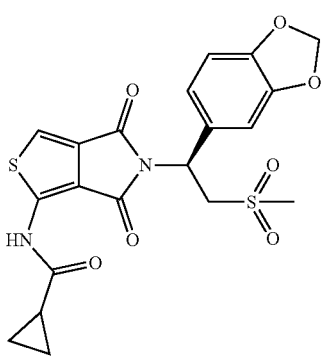

(13)

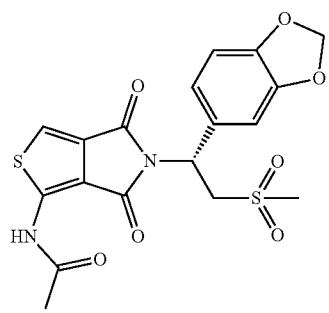

(18)

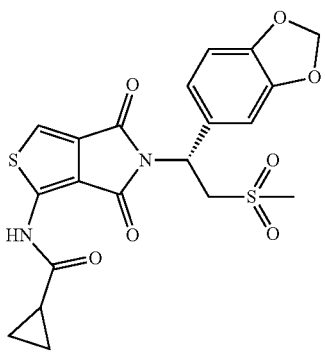

(19)

To a solution of (S)-1-amino-5-(1-(benzo[d][1,3]dioxol-5-yl)-2-(methylsulfonyl)ethyl)-4H-thieno[3,4-c]pyrrole-4,6(5H)-dione (130 mg, 0.33 mmol) in ACN (3 mL) was added pyridine (0.1 mL). The mixture was cooled to 0° C. then acetyl chloride (0.1 mL in 1 mL ACN) was added dropwise, and the mixture was stirred at 0° C. for 0.5 h. HCl (2M, 3 mL) was added, and the organic layer was washed with brine, dried over $Na_2SO_4$, concentrated, and purified by prep-HPLC (ACN/$H_2O$, 5%-95%) to give Compound 12 (49 mg, 34%) as a white solid. MS (ESI) m/z 437.1 [M+H]$^+$. $^1$H NMR (400 MHz, DMSO-d6) δ 11.73 (s, 1H), 7.75 (s, 1H), 7.06 (s, 1H), 6.89 (s, 2H), 6.02 (d, J=4.0, 2H), 5.69 (q, 1H), 4.31 (q, 1H), 4.08 (q, 1H), 3.01 (s, 3H), 2.23 (s, 1H). Compound 18 was prepared analogously to Compound 12. MS (ESI) m/z 454.0 [M+$H_2O$]$^+$.

To a solution of (S)-1-amino-5-(1-(benzo[d][1,3]dioxol-5-yl)-2-(methylsulfonyl)ethyl)-4H-thieno[3,4-c]pyrrole-4,6(5H)-dione (180 mg, 0.46 mmol) in ACN (3 mL) was added pyridine (0.1 mL). The mixture was cooled to 0° C., then cyclopropanecarbonyl chloride (0.3 mL in 1 mL ACN, which was prepared from cyclopropanecarboxylic acid with $SOCl_2$ reflux for 2H) was added drop wised, the mixture was stirred at 0° C. for 0.5 h. HCl (2M, 3 mL) was added, the organic layer was washed with brine, dried over $Na_2SO_4$, concentrated and purified by prep-HPLC (ACN/$H_2O$=5%-95%) to give the title compound (48 mg, 23%) as a white solid. MS (ESI) m/z 463.8 [M+H]$^+$. $^1$H NMR (400 MHz, DMSO-d6) δ 11.98 (s, 1H), 7.75 (s, 1H), 7.07 (s, 1H), 6.90 (s, 2H), 6.02 (d, J=4.0, 2H), 5.70 (q, 1H), 4.31 (q, 1H), 4.08 (q, 1H), 3.01 (s, 3H), 2.31 (m, 1H), 0.92 (m, 4H). Compound 19 was prepared analogously to Compound 13. MS (ESI) m/z 463.8 [M+H]$^+$.

Example 14: Compound 14 (S) and Compound 20 (R): N-(5-(1-(2,3-dihydrobenzo[b][1,4] dioxin-6-yl)-2-(methylsulfonyl)ethyl)-4,6-dioxo-5,6-dihydro-4H-thieno[3,4-c]pyrrol-1-yl) acetamide

(14)
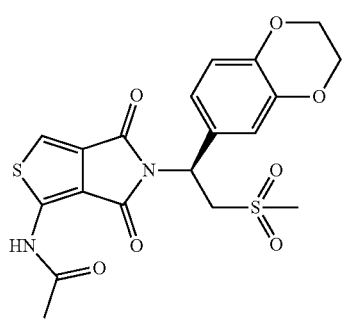

(20)
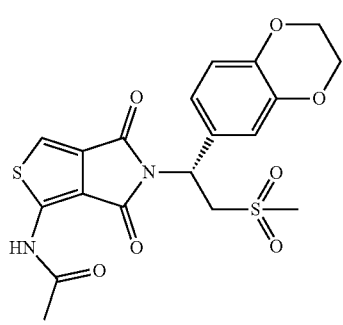

A solution of 2,3-dihydrobenzo[b][1,4]dioxine-6-carbaldehyde (10.0 g, 60.97 mmol) in DMF (100 mL) was added dimethyl sulfone (11.0 g, 121.95 mmol) and NaOH (3.7 g, 91.46 mmol). The mixture was heated to 50° C. for 2 h, then concentrated and purified on silica gel eluting with EA/PE from 50% to 80% to give (E)-6-(2-(methylsulfonyl)vinyl)-2,3-dihydrobenzo[b][1,4]dioxine (5.3 g, 36%) as a yellow solid. MS (ESI) m/z 241.2 [M+1]$^+$.

A mixture of (E)-6-(2-(methylsulfonyl)vinyl)-2,3-dihydrobenzo[b][1,4]dioxine (5.3 g, 22.08 mmol) and hydroxylamine (7.3 g, 221.2 mmol) in THF (50 mL) was heated to reflux overnight. The mixture was concentrated and purified on silica gel eluting with EA/PE from 80% to 100% to give N-(1-(2,3-dihydrobenzo[b][1,4]dioxin-6-yl)-2-(methylsulfonyl)ethyl)hydroxylamine (3.8 g, 62%) as a colorless oil. MS (ESI) m/z 275.1 [M+1]$^+$.

A mixture of N-(1-(2,3-dihydrobenzo[b][1,4]dioxin-6-yl)-2-(methylsulfonyl)ethyl)hydroxylamine (3.8 g, 13.90 mmol) and Pd/C (380 mg) in MeOH (30 mL) was stirred at RT under hydrogen overnight. The mixture was filtered and the filtrate was concentrated to give crude 1-(2,3-dihydrobenzo[b][1,4]dioxin-6-yl)-2-(methylsulfonyl)ethanamine. Chiral prep-HPLC afforded the two enantiomers: S isomer (peak 1, 320 mg) as a white solid and R isomer (peak 2, 350 mg) as a white solid. S isomer MS (ESI) m/z 258.3 [M+1]$^+$.

A mixture of 4-nitrothieno[3,4-c]furan-1,3-dione (199 mg, 1.0 mmol) and (S)-1-(2,3-dihydrobenzo[b][1,4]dioxin-6-yl)-2-(methylsulfonyl)ethanamine (257 mg, 1.0 mmol) in THF (15 mL) was stirred at RT for 1 h. 1,1'-Carbonyldiimidazol (195 mg, 1.2 mmol) was added and the mixture was stirred at 80 C for 1 h. The mixture was diluted with EA (100 mL), washed with water (100 mL) and brine (50 mL), dried over Na$_2$SO$_4$, concentrated, and purified on silica gel eluting with EA/PE (1:1) to give (S)-5-(1-(2,3-dihydrobenzo[b][1,4]dioxin-6-yl)-2-(methylsulfonyl)ethyl)-1-nitro-4H-thieno[3,4-c]pyrrole-4,6(5H)-dione(7) (300 mg, 68%) as a yellow solid. MS (ESI) m/z 439.1 [M+1]$^+$.

A mixture of (S)-5-(1-(2,3-dihydrobenzo[b][1,4]dioxin-6-yl)-2-(methylsulfonyl)ethyl)-1-nitro-4H-thieno[3,4-c]pyrrole-4,6(5H)-dione (150 mg, 0.34 mmol), ammonium chloride (91 mg, 1.7 mmol) and iron powder (96 mg, 1.7 mmol) in THF/water (10 mL/3 mL) was stirred at 80° C. for 1 h. The reaction was diluted with EA (100 mL), washed with water (100 mL) and brine (50 mL), dried over Na$_2$SO$_4$, concentrated, and purified on silica gel eluting with EA/PE (2:1) to give (S)-1-amino-5-(1-(2,3-dihydrobenzo[b][1,4]dioxin-6-yl)-2-(methylsulfonyl)ethyl)-4H-thieno[3,4-c]pyrrole-4,6(5H)-dione (21 mg, 15%) as a yellow solid. MS (ESI) m/z 409.1 [M+H]$^+$.

To a solution of (S)-1-amino-5-(1-(2,3-dihydrobenzo[b][1,4]dioxin-6-yl)-2-(methylsulfonyl)ethyl)-4H-thieno[3,4-c]pyrrole-4,6(5H)-dione (21 mg, 0.05 mmol) in pyridine (4 mL) was added acetyl chloride (0.1 mL) at 0° C. The mixture was stirred at 0° C. for 2 h. The reaction was quenched with water (50 mL) and extracted with EA (50 mL). The organic phase was washed with 0.5 N HCl (20 mL) and brine (50 mL). The organic phase was dried over Na$_2$SO$_4$, concentrated, and purified by prep-HPLC (ACN/H$_2$O, 5%-95%) to give the title compound (10.5 mg, 47%) as a white solid. MS (ESI) m/z 451.0 [M+H]$^+$. $^1$H NMR (400 MHz, CDCl$_3$) δ 9.27 (s, 1H), 7.32 (s, 1H), 7.05 (d, J=2.0 Hz, 1H), 6.97 (dd, J=2.0, 8.4 Hz, 1H), 6.84 (d, J=8.4 Hz, 1H), 5.80 (dd, J=4.0, 10.4 Hz, 1H), 4.55 (dd, J=10.4, 14.4 Hz, 1H), 4.23 (s, 4H), 3.70 (dd, J=4.0, 14.4 Hz, 1H), 2.90 (s, 3H), 2.28 (s, 3H). Compound 20 was prepared analogously to Compound 14. MS (ESI) m/z 468.0 [M+H$_2$O]$^+$.

Example 15: Compound 15: (S)—N-(5-(2-(N,N-dimethylsulfamoyl)-1-(3-ethoxy-4-methoxyphenyl)ethyl)-4,6-dioxo-5,6-dihydro-4H-thieno[3,4-c]pyrrol-1-yl)acetamide

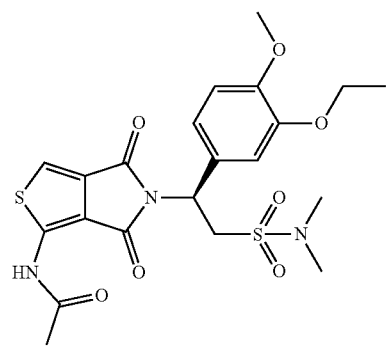 [SMILES: CCOc1cc([C@@H](CS(=O)(=O)N(C)C)N2C(=O)c3csc(NC(C)=O)c3C2=O)ccc1OC]

To a solution of N,N-dimethylmethanesulfonamide (23.9 g, 194.23 mmol) in N,N-dimethylacetamide (150 mL) was added KOH (6.54 g, 116.55 mmol) at RT. The mixture was stirred for 15 min at RT. Then 3-ethoxy-4-methoxybenzaldehyde (14 g, 77.7 mmol) was added and the mixture was stirred for 2 h at 60° C. The mixture was poured onto ice water (300 mL) and filtered, and purified on silica gel to afford (E)-2-(3-ethoxy-4-methoxyphenyl)-N,N-dimethylethenesulfonamide (9.5 g, 43%) a white solid. MS (ESI) m/z=286.1 [M+H]$^+$.

To a solution of (E)-2-(3-ethoxy-4-methoxyphenyl)-N,N-dimethylethenesulfonamide (7.3 g, 25.56 mmol) in THF (70 mL) was added hydroxylamine (60 mL, 2.2 mol) at RT. The mixture was warmed to 60° C. and stirred for 16 h. The mixture was poured onto ice water (50 mL) and stirred for 10 minutes then extracted with EA. The combined organic layers were washed with brine, dried over $Na_2SO_4$, filtered, and evaporated. The mixture was concentrated and purified on silica gel to afford 2-(3-ethoxy-4-methoxyphenyl)-2-(hydroxyamino)-N,N-dimethylethanesulfonamide (4.5 g, 55%) a white solid. MS (ESI) m/z=319.0 [M+H]$^+$.

To a solution of 2-(3-ethoxy-4-methoxyphenyl)-2-(hydroxyamino)-N,N-dimethylethanesulfonamide (4.5 g, 14.13 mmol) in MeOH (50 mL) at RT was added Pd/C (1 g). The mixture was stirred at RT overnight under hydrogen. The suspension was filtered through a pad of celite and the filtrate was concentrated. The residue was purified on silica gel to afford 2-amino-2-(3-ethoxy-4-methoxyphenyl)-N,N-dimethylethanesulfonamide (3.8 g, 89%) a white solid. Chiral Prep-HPLC gave two enantiomers: S isomer (peak 1, 1.5 g) as a white solid and R isomer (peak 2, 1.4 g) as a white solid. S isomer MS (ESI) m/z=303.1 [M+H]$^+$. $^1$H NMR (400 MHz, DMSO-d6) δ 7.02 (s, 1H), 6.91-6.85 (m, 1H), 4.28-4.24 (m, 1H), 4.04-3.97 (m, 2H), 3.72 (m, 3H), 3.29-3.21 (m, 1H), 3.15-3.09 (m, 1H), 2.74-2.69 (m, 6H), 2.08 (m, 2H), 1.34-1.30 (m, 3H).

A mixture of 4-nitrothieno[3,4-c]furan-1,3-dione (199 mg, 1.0 mmol) and (S)-2-amino-2-(3-ethoxy-4-methoxyphenyl)-N,N-dimethylethanesulfonamide (302 mg, 1.0 mmol) in THF (10 mL) was stirred at RT for 1 h. 1,1'-Carbonyldiimidazol (211 mg, 1.3 mmol) was added and the mixture was stirred at 80° C. for 1 h. The reaction was diluted with EA (100 mL), washed with water (100 mL) and brine (50 mL), dried, concentrated, and purified on silica gel (PE/EA, 2:3) to give (S)-2-(3-ethoxy-4-methoxyphenyl)-N,N-dimethyl-2-(1-nitro-4,6-dioxo-4H-thieno[3,4-c]pyrrol-5(6H)-yl)ethanesulfonamide (415 mg, 86%) as a yellow solid. MS (ESI) m/z 484.1 [M+1]$^+$.

A mixture of (S)-2-(3-ethoxy-4-methoxyphenyl)-N,N-dimethyl-2-(1-nitro-4,6-dioxo-4H-thieno[3,4-c]pyrrol-5(6H)-yl)ethanesulfonamide (410 mg, 0.85 mmol), ammonium chloride (228 mg, 4.25 mmol) and iron powder (238 mg, 4.25 mmol) in THF/water (10 mL/3 mL) was heated to reflux for 1 h. The reaction was diluted with EA (100 mL), washed with water (100 mL) and brine (50 mL), dried, concentrated, and purified on silica gel (PE/EA, 2:3) to give (S)-2-(1-amino-4,6-dioxo-4H-thieno[3,4-c]pyrrol-5(6H)-yl)-2-(3-ethoxy-4-methoxyphenyl)-N,N-dimethylethanesulfonamide (110 mg, 29%) as a yellow semi-solid. MS (ESI) m/z 439.1[M+H]$^+$.

To a solution of (S)-2-(1-amino-4,6-dioxo-4H-thieno[3,4-c]pyrrol-5(6H)-yl)-2-(3-ethoxy-4-methoxyphenyl)-N,N-dimethylethanesulfonamide (110 mg, 0.25 mmol) in pyridine (6 mL) was added acetyl chloride (198 mg, 2.5 mmol) at 0° C. The mixture was stirred at 0° C. for 2 h. The reaction was quenched with water (50 mL), extracted with EA (50 mL), the organic phase was washed with 0.5 N HCl (20 mL) and brine (50 mL). The organic phase was dried over $Na_2SO_4$, concentrated, and purified with prep-TLC (PE/EA, 1:1) to give the title compound (67 mg, 54%) as a white solid. MS (ESI) m/z 496.1 [M+H]$^+$. $^1$H NMR (400 MHz, CDCl$_3$) δ 9.10 (s, 1H), 7.32 (s, 1H), 7.08-7.05 (m, 2H), 6.83 (d, J=8.4 Hz, 1H), 5.74 (dd, J=3.2, 11.2 Hz, 1H), 4.56 (dd, J=11.2, 14.4 Hz, 1H), 4.10 (q, J=6.8 Hz, 2H), 3.85 (s, 3H), 3.42 (dd, J=3.2, 14.4 Hz, 1H), 2.84 (s, 6H), 2.29 (s, 3H), 1.47 (t, J=6.8 Hz, 3H).

Example 16: Compound 16 (S) and Compound 17 (R): N-(5-(1-(benzo[d][1,3]dioxol-5-yl)-2-(methylsulfonyl)ethyl)-4,6-dioxo-5,6-dihydro-4H-thieno[3,4-c]pyrrol-1-yl)-2,2,2-trifluoro acetamide

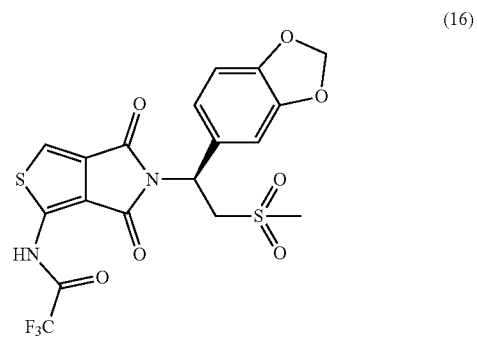

(16)

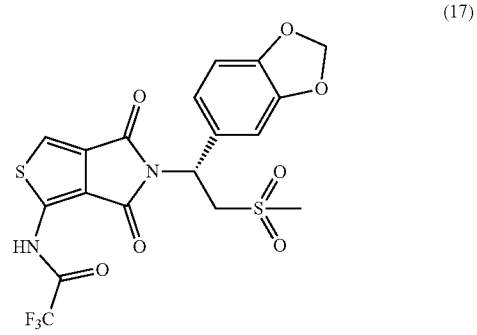

(17)

To a solution of 3,4-dihydroxybenzaldehyde (50.0 g, 37.5 mmol) in DMF (500 mL) was added DCM (50.0 g, 588.9 mmol) and $K_2CO_3$ (7.76 g, 52.25 mmol). The mixture was heated to 120° C. for 2 h then concentrated and purified on silica gel eluting with EA/PE from 50% to 70% to give benzo[d][1,3]dioxole-5-carbaldehyde (49 g, 90%) as a black solid. MS (ESI) m/z 151.1 [M+1]$^+$.

A solution of benzo[d][1,3]dioxole-5-carbaldehyde (38.0 g, 253.33 mmol) in DMF (400 mL) was added dimethyl sulfone (59.7 g, 633.33 mmol) and NaOH (15.2 g, 380 mmol). The mixture was heated to 50° C. for 2 h then concentrated and purified on silica gel eluting with EA/PE from 50% to 80% to give (E)-5-(2-(methylsulfonyl)vinyl)benzo[d][1,3]dioxole (24.0 g, 44.1%) as a yellow solid. MS (ESI) m/z 227.3 [M+1]$^+$.

A mixture of (E)-5-(2-(methylsulfonyl)vinyl)benzo[d][1,3]dioxole (24.0 g, 106.05 mmol) and hydroxylamine (29.1 g, 221.2 mmol) in THF (200 mL) was heated to reflux for overnight. The mixture was concentrated and purified on silica gel (PE/EA=80%-100%) to give N-(1-(benzo[d][1,3]dioxol-5-yl)-2-(methylsulfonyl)ethyl)hydroxylamine (12.0 g, 43.7%) as a colorless oil. MS (ESI) m/z 260.3 [M+1]$^+$.

A mixture of N-(1-(benzo[d][1,3]dioxol-5-yl)-2-(methylsulfonyl)ethyl) hydroxylamine (12.0 g, 13.78 mmol) and Pd/C (1.2 g) in MeOH (30 mL) was stirred at RT under H$_2$ overnight. The mixture was filtered and the filtrate was concentrated and purified on silica gel eluting with EA/PE from 80% to 100% to give 1-(benzo[d][1,3]dioxol-5-yl)-2-(methylsulfonyl)ethanamine (5.4 g, 48%) as a white solid. Chiral prep-HPLC afforded the two enantiomers as white solids: S isomer (peak 1, 2.53 g, 93.7%); R isomer (peak 2, 2.5 g, 92.6%). S isomer MS (ESI) m/z 243.3 [M+1]$^+$.

A mixture of 4-nitrothieno[3,4-c]furan-1,3-dione (357 mg, 1.79 mmol), and (S)-1-(benzo[d][1,3]dioxol-5-yl)-2-(methylsulfonyl)ethanamine (420 mg, 1.79 mmol) in THF (15 mL) was stirred at RT for 1 h then 1,1'-carbonyldiimidazole (348 mg, 2.15 mmol) was added and the reaction was heated to reflux for another 1 h. The mixture was concentrated and the residue was purified on silica gel eluting with EA/PE from 30% to 50% to give (S)-5-(1-(benzo[d][1,3]dioxol-5-yl)-2-(methylsulfonyl)ethyl)-1-nitro-4H-thieno-[3,4-c]pyrrole-4,6(5H)-dione (630 mg, 83%) as a yellow solid. MS (ESI) m/z 426.1 [M+1]⁺.

A mixture of (S)-5-(1-(benzo[d][1,3]dioxol-5-yl)-2-(methylsulfonyl) ethyl)-1-nitro-4H-thieno[3,4-c]pyrrole-4,6(5H)-dione (500 mg, 1.18 mmol), ammonium chloride (375 mg, 7.08 mmol) and iron powder (528 mg, 5.34 mmol) in THF/water (5 mL/2 mL) was heated to reflux for 1 h. The reaction was filtered, concentrated, and purified on silica gel eluting with EA/PE from 40% to 70% to give (S)-1-amino-5-(1-(benzo[d][1,3]dioxol-5-yl)-2-(methylsulfonyl)ethyl)-4H-thieno[3,4-c]pyrrole-4,6(5H)-dione (160 mg, 35%) as a yellow solid. MS (ESI) m/z 394.1 [M+H]⁺.

To a solution of (S)-1-amino-5-(1-(benzo[d][1,3]dioxol-5-yl)-2-(methylsulfonyl)ethyl)-4H-thieno[3,4-c]pyrrole-4,6(5H)-dione (160 mg, 0.41 mmol) in ACN (3 mL) was added pyridine (0.1 mL). The mixture was cooled to 0° C., then trifluoroacetic anhydride (0.1 mL in 1 mL ACN) was added dropwise. The mixture was stirred at 0° C. for 0.5 h then HCl (2M, 3 mL) was added. The organic layer was washed with brine, dried over Na₂SO₄, concentrated, and purified by prep-HPLC (ACN/H₂O=5%-95%) to give Compound 16 (49 mg, 24%) as a white solid. MS (ESI) m/z 508.1 [M+H₂O]⁺. ¹H NMR (400 MHz, DMSO-d6) δ 7.96 (s, 1H), 7.06 (s, 1H), 6.89 (s, 2H), 6.01 (d, J=4.0, 2H), 5.70 (q, 1H), 4.31 (q, 1H), 4.08 (q, 1H), 3.01 (s, 3H). Compound 17 was prepared analogously to Compound 16. MS (ESI) m/z 508.0 [M+H₂O]⁺.

Example 17: Compound 21 (S) and Compound 22 (R): N-(5-(1-(benzo[d][1,3]dioxol-5-yl)-2-(methylsulfonyl)ethyl)-4,6-dioxo-5,6-dihydro-4H-thieno[2,3-c]pyrrol-3-yl)-2,2,2-trifluoroacetamide (21)

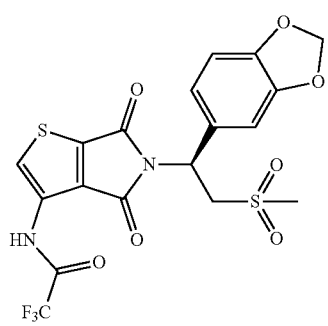

(22)

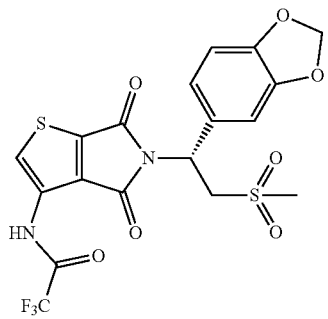

To a solution of 3-bromothieno[2,3-c]furan-4,6-dione (317.6 mg, 1.37 mmol) in THF (10 mL) at RT was added 1-(benzo[d][1,3]dioxol-5-yl)-2-(methylsulfonyl)ethanamine (333 mg, 1.37 mmol). The mixture was stirred for 1 h then 1,1'-carbonyldiimidazol (332.9 mg, 2.06 mol) was added and the mixture was heated at 70° C. for 1 h. The reaction was cooled and concentrated. The residue was purified on silica gel eluting with EA/PE from 10% to 50% to give 5-(1-(benzo[d][1,3]dioxol-5-yl)-2-(methylsulfonyl)ethyl)-3-bromo-4H-thieno[2,3-c]pyrrole-4,6(5H)-dione (502 mg, 77.1%) as a light yellow solid. MS (ESI) m/z 474.8, 476.8. [M+H₂O]⁺.

To a suspension of 5-(1-(benzo[d][1,3]dioxol-5-yl)-2-(methylsulfonyl)ethyl)-3-bromo-4H-thieno[2,3-c]pyrrole-4,6(5H)-dione (316 mg, 0.693 mmol) in 1,4-dioxane/toluene (15 mL/15 mL) at RT was added diphenylmethanimine (188 mg, 1.04 mmol) and CsCO₃ (450 mg, 1.38 mmol). The suspension was degassed and purged with nitrogen twice. Tris(dibenzylideneacetone)dipalladium Pd₂(dba)₃ (253 mg, 0.277 mmol) and Xantphos (240 mg, 0.416 mmol) was added. The suspension was heated at 100° C. for 16 h. The reaction was cooled and concentrated. The residue was purified on silica gel eluting with EA/PE from 10% to 50% to give 5-(1-(benzo[d][1,3]dioxol-5-yl)-2-(methylsulfonyl)ethyl-3-((diphenylmethylene)amino)-4H-thieno[2,3-c]pyrrole-4,6(5H)-dione (241 mg, 39.8%) as a yellow gum. MS (ESI) m/z 559.0 [M+H]⁺.

To a solution of 5-(1-(benzo[d][1,3]dioxol-5-yl)-2-(methylsulfonyl)ethyl)-3-((diphenylmethylene) amino)-4H-thieno[2,3-c]pyrrole-4,6(5H)-dione (163 mg, 0.293 mmol) in MeOH/DCM (8 mL/2 mL) at RT was added hydroxylamine hydrochloride (81 mg, 1.632 mmol) and NaOAc (120 mg, 1.465 mmol). The suspension was stirred at RT for 3 h, concentrated, and purified on silica gel eluting with EA/PE from 10% to 50% to give 3-amino-5-(1-(benzo[d][1,3]dioxol-5-yl)-2-(methylsulfonyl)ethyl)-4H-thieno[2,3-c]pyrrole-4,6(5H)-dione (83 mg, 48%) as a yellow solid. MS (ESI) m/z 394.9 [M+H]⁺.

To a solution of 3-amino-5-(1-(benzo[d][1,3]dioxol-5-yl)-2-(methylsulfonyl) ethyl)-4H-thieno[2,3-c]pyrrole-4,6(5H)-dione (32 mg, 0.081 mmol) in DCM/pyridine (2 mL/2 mL) at 0° C. was added a solution of trifluoroacetic anhydride (86 mg, 0.405 mmol) in DCM (0.5 mL). The reaction was stirred at 0° C. for 10 min, quenched with water (1 mL), and extracted with DCM. The combined organic layers were washed with 1N HCl, dried over Na₂SO₄, filtered, concentrated, and purified by prep-TLC (PE/EA, 1:1) to give the title compound (26.1 mg, 65.7%) as a light yellow solid. Chiral prep-HPLC afforded the two enantiomers. (S) enantiomer (21): MS (ESI) m/z 508.0 [M+H₂O]⁺; ¹H NMR (400 MHz, DMSO-d6) δ 11.71 (s, 1H), 8.18 (s, 1H), 7.08 (s, 1H), 6.91 (s, 2H), 6.02 (dd, J=1.2, 3.6 Hz, 2H), 5.67 (dd, J=4.4, 10.0 Hz, 1H), 4.27 (dd, J=10.8, 14.4 Hz, 1H), 4.09 (dd, J=4.8, 14.4 Hz, 1H), 3.01 (s, 3H). (R) enantiomer (22): MS (ESI) m/z 508.0 [M+H₂O]⁺.

Example 18: Compound 23 (S) and Compound 24 (R): N-(5-(1-(benzo[d][1,3]dioxol-5-yl)-2-(methylsulfonyl)ethyl)-4,6-dioxo-5,6-dihydro-4H-thieno[2,3-c]pyrrol-3-yl)acetamide

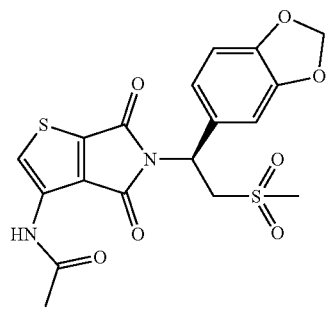
(23)

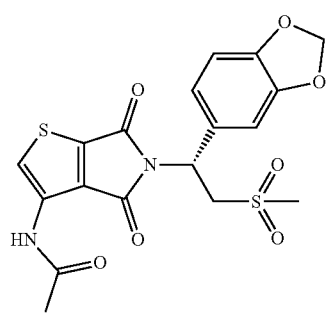
(24)

To a solution of 3-amino-5-(1-(benzo[d][1,3]dioxol-5-yl)-2-(methylsulfonyl)ethyl)-4H-thieno[2,3-c]pyrrole-4,6(5H)-dione (49 mg, 0.125 mmol) in DCM/pyridine (2 mL/2 mL) at 0° C. was added a solution of acetyl chloride (49 mg, 0.623 mmol) in DCM (0.5 mL). The reaction was stirred at 0° C. for 10 min then quenched with water (1 mL) and extracted with DCM. The combined organic layers were washed with 1 N HCl, dried over Na₂SO₄, filtered, concentrated, and purified by prep-TLC (PE/EA=1/1) to give the title compound (21.4 mg, 39.5%) as a light yellow solid. Chiral prep-HPLC afforded the two enantiomers. (S) enantiomer (23): MS (ESI) m/z 437.0 [M+H]⁺. ¹H NMR (400 MHz, DMSO-d6) δ 10.07 (s, 1H), 8.28 (s, 1H), 7.08 (s, 1H), 6.91 (s, 2H), 6.02 (d, J=2.4 Hz, 2H), 5.68 (dd, J=4.4, 10.4 Hz, 1H), 4.27 (dd, J=10.8, 14.4 Hz, 1H), 4.08 (dd, J=4.4, 14.4 Hz, 1H), 3.02 (s, 3H), 2.11 (s, 3H). (R) enantiomer (24): MS (ESI) m/z 454.0 [M+H₂O]⁺.

Example 19: Compound 25 (S) and Compound 26 (R): N-(5-(1-(benzo[d][1,3]dioxol-5-yl)-2-(methylsulfonyl)ethyl)-4,6-dioxo-5,6-dihydro-4H-thieno[2,3-c]pyrrol-3-yl)-2-methoxy acetamide

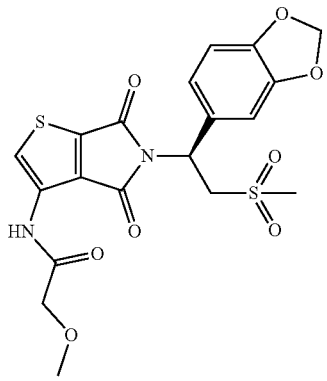
(25)

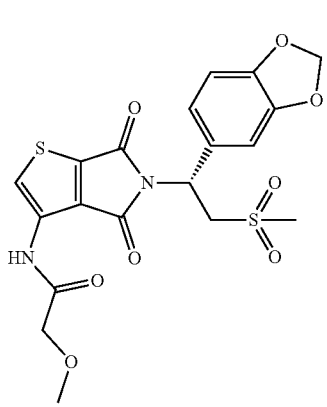
(26)

To a solution of 3-amino-5-(1-(benzo[d][1,3]dioxol-5-yl)-2-(methylsulfonyl)ethyl)-4H-thieno[2,3-c]pyrrole-4,6(5H)-dione (32 mg, 0.081 mmol) in DCM/pyridine (2 mL/2 mL) at 0° C. was added a solution of 2-methoxyacetyl chloride (44 mg, 0.407 mmol) in DCM (0.5 mL). The reaction was stirred at 0° C. for 10 min then quenched with H₂O (1 mL) and extracted with DCM. The combined organic layers were washed with 1 N HCl, dried over Na₂SO₄, filtered, concentrated, and purified by prep-TLC (PE/EA, 1:1) to give the title compound (31.4 mg, 82.8%) as a yellow solid. Chiral prep-HPLC afforded the two enantiomers. (S) enantiomer (25): MS (ESI) m/z 467.0 [M+H]⁺. ¹H NMR (400 MHz, DMSO-d6) δ 9.54 (s, 1H), 8.31 (s, 1H), 7.08 (s, 1H), 6.91 (s, 2H), 6.02 (d, J=2.0 Hz, 2H), 5.67 (dd, J=4.0, 10.0 Hz, 1H), 4.09 (dd, J=4.8, 9.6 Hz, 1H), 4.08 (s, 2H), 3.42 (s, 3H), 3.02 (s, 3H). (R) enantiomer (26): MS (ESI) m/z 484.1 [M+H₂O]⁺.

Example 20: Compound 27 (S) and Compound 28 (R): N-(5-(1-(benzo[d][1,3]dioxol-5-yl)-2-(N,N-dimethylsulfamoyl)ethyl)-4,6-dioxo-5,6-dihydro-4H-thieno[3,4-c]pyrrol-1-yl)acetamide (27)

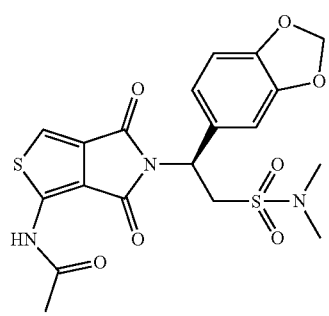

(28)

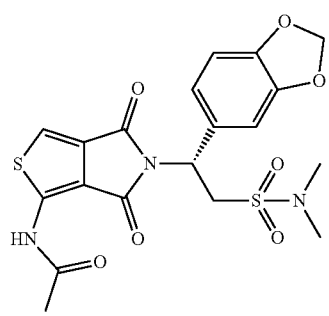

A solution of benzo[d][1,3]dioxole-5-carbaldehyde (8.0 g, 53.33 mmol) in DMF (100 mL) was added N,N-dimethylmethanesulfonamide (16.5 g, 133.33 mmol) and NaOH (3.2 g, 80 mmol). The mixture was heated at 50° C. for 2 h, concentrated, and purified on silica gel (PE/EA, 50%-80%) to give (E)-2-(benzo[d][1,3] dioxol-5-yl)-N,N-dimethylethenesulfonamide (6.2 g, 45.5%) as a yellow solid. MS (ESI) m/z 256.3 [M+1]$^+$.

A mixture of (E)-2-(benzo[d][1,3]dioxol-5-yl)-N,N-dimethylethene sulfonamide (6.2 g, 24.29 mmol) and NH$_2$OH (7.3 g, 221.2 mmol) in THF (50 mL) was heated to reflux overnight. The mixture was concentrated and purified on silica gel (PE/EA, 80%-100%) to give 2-(benzo[d][1,3] dioxol-5-yl)-2-(hydroxyamino)-N,N-dimethylethane sulfonamide (3.6 g, 51.4%) as a colorless oil. MS (ESI) m/z 289.3 [M+1]$^+$.

A mixture of 2-(benzo[d][1,3]dioxol-5-yl)-2-(hydroxyamino)-N,N-dimethylethanesulfonamide (3.6 g, 13.78 mmol) and Pd/C (360 mg) in MeOH (30 mL) was stirred at RT under H$_2$ overnight. The mixture was filtered, concentrated, and purified on silica gel (PE/EA, 80%-100%) to give 2-amino-2-(benzo[d][1,3]dioxol-5-yl)-N,N-dimethylethanesulfonamide (3 g, 89%) as a white solid. MS (ESI) m/z 273.3 [M+1]$^+$.

A mixture of 2-amino-2-(benzo[d][1,3]dioxol-5-yl)-N,N-dimethylethane sulfonamide (3 g, 11.02 mmol) and di-tert-butyl dicarbonate (3.6 g, 16.51 mmol) in MeOH (30 mL) was stirred at RT overnight. The mixture was concentrated and purified on silica gel (PE/EA, 80%-100%) to give tert-butyl(1-(benzo[d][1,3]dioxol-5-yl)-2-(N,N-dimethyl sulfamoyl)ethyl)carbamate (2.8 g, 68.3%) as a colorless oil. Chiral prep-HPLC afforded the two enantiomers as white solids: S isomer (peak 1, 1.33 g, 95%); R isomer (peak 2, 1.3 g, 92.9%). S isomer MS (ESI) m/z 373.4 [M+1]$^+$.

A mixture of 4-nitrothieno[3,4-c]furan-1,3-dione (630 mg, 2.32 mmol) and (S)-2-amino-2-(benzo[d][1,3]dioxol-5-yl)-N,N-dimethylethanesulfonamide (390 mg, 1.96 mmol) in THF (10 mL) was stirred at RT for 1 h then 1,1'-carbonyldiimidazol (381 mg, 2.35 mmol) was added. The reaction was heated to reflux for another 1 h then concentrated and purified on silica gel (PE/EA, 30%-50%) to give (S)-2-(benzo[d][1,3]dioxol-5-yl)-N,N-dimethyl-2-(1-nitro-4,6-dioxo-4H-thieno[3,4-c]pyrrol-5(6H)-yl)ethanesulfonamide (420 mg, 47%) as a yellow solid. MS (ESI) m/z 453.9 [M+1]$^+$.

A mixture of (S)-2-(benzo[d][1,3]dioxol-5-yl)-N,N-dimethyl-2-(1-nitro-4,6-dioxo-4H-thieno[3,4-c]pyrrol-5(6H)-yl)ethanesulfonamide (440 mg, 0.97 mmol), ammonium chloride (309 mg, 5.83 mmol) and iron powder (326 mg, 5.83 mmol) in THF/water (5 mL/2 mL) was heated to reflux for 1 h. The mixture was filtered, concentrated, purified on silica gel (PE/EA, 40%-70%) to give (S)-2-(1-amino-4,6-dioxo-4H-thieno[3,4-c]pyrrol-5(6H)-yl)-2-(benzo[d][1,3] dioxol-5-yl)-N,N-dimethylethanesulfonamide (148 mg, 34%) as a yellow solid. MS (ESI) m/z 453.1[M+H]$^+$.

To a solution of (S)-2-(1-amino-4,6-dioxo-4H-thieno[3,4-c]pyrrol-5(6H)-yl)-2-(benzo[d][1,3]dioxol-5-yl)-N,N-dimethylethanesulfonamide (148 mg, 0.33 mmol) in DCM (3 mL) was added pyridine (0.1 mL). The mixture was cooled to 0° C. then acetyl chloride (0.1 mL in 1 mL ACN) was added dropwise. The mixture was stirred at 0° C. for 0.5 h. HCl (2M, 3 mL) was added then the organic layer was washed with brine, dried over Na$_2$SO$_4$, concentrated and purified by prep-HPLC (ACN/H$_2$O, 5%-95%) to give Compound 27 (65 mg, 43%) as a white solid. MS (ESI) m/z 466.0 [M+H]$^+$. $^1$H NMR (400 MHz, DMSO-d6) δ 11.73 (s, 1H), 7.76 (s, 1H), 7.09 (s, 1H), 6.90 (s, 2H), 6.02 (d, J=4.0, 2H), 5.62 (q, 1H), 4.30-4.31 (m, 1H), 3.45-3.48 (m, 1H), 2.77 (s, 6H), 2.24 (s, 1H). Compound 28 was prepared analogously to Compound 27. MS (ESI) m/z 483.1 [M+H$_2$O]$^+$.

Example 21: Compound 29: (R)—N-(5-(2-(N,N-dimethylsulfamoyl)-1-(3-ethoxy-4-methoxyphenyl)ethyl)-4,6-dioxo-5,6-dihydro-4H-thieno[3,4-c]pyrrol-yl)acetamide

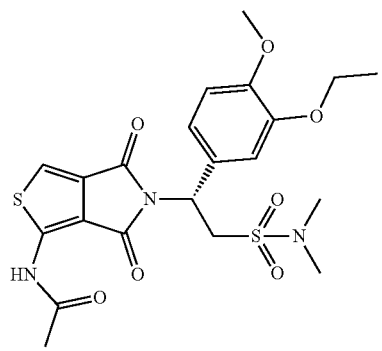 [SMILES: CCOc1cc([C@H](CS(=O)(=O)N(C)C)N2C(=O)c3csc(NC(C)=O)c3C2=O)ccc1OC]

A mixture of (R)-2-(3-ethoxy-4-methoxyphenyl)-N,N-dimethyl-2-(1-nitro-4,6-dioxo-4H-thieno[3,4-c]pyrrol-5(6H)-yl)ethanesulfonamide (410 mg, 0.85 mmol), ammonium chloride (228 mg, 4.25 mmol) and iron powder (238 mg, 4.25 mmol) in THF/water (10 mL/3 mL) was heated to reflux for 1 h. The reaction was diluted with EA (100 mL), washed with water (100 mL) and brine (50 mL), dried over Na$_2$SO$_4$, concentrated, and purified on silica gel (PE/EA, 2:3) to give (R)-2-(1-amino-4,6-dioxo-4H-thieno-[3,4-c]pyrrol-5(6H)-yl)-2-(3-ethoxy-4-methoxyphenyl)-N,N-dimethylethanesulfonamide (110 mg, 29%) as a yellow semi-solid. MS (ESI) m/z 439.1 [M+H]⁺.

To a solution of (R)-2-(1-amino-4,6-dioxo-4H-thieno[3,4-c]pyrrol-5(6H)-yl)-2-(3-ethoxy-4-methoxyphenyl)-N,N-dimethylethanesulfonamide (110 mg, 0.25 mmol) in pyridine (6 mL) was added acetyl chloride (198 mg, 2.5 mmol) at 0° C., and stirred at 0° C. for 2 h. The reaction was quenched with water (50 mL), extracted with EA (50 mL), and the organic phase was washed with 0.5N HCl (20 mL) and brine (50 mL). The organic phase was dried over Na₂SO₄, concentrated, and purified with prep-TLC (PE/EA, 1:1) to give the title compound (67 mg, 54%) as a white solid. MS (ESI) m/z 496.1 [M+H]⁺. ¹H NMR (400 MHz, CDCl₃) δ 9.10 (s, 1H), 7.32 (s, 1H), 7.08-7.05 (m, 2H), 6.83 (d, J=8.4 Hz, 1H), 5.74 (dd, J=3.2, 11.2 Hz, 1H), 4.56 (dd, J=11.2, 14.4 Hz, 1H), 4.10 (q, J=6.8 Hz, 2H), 3.85 (s, 3H), 3.42 (dd, J=3.2, 14.4 Hz, 1H), 2.84 (s, 6H), 2.29 (s, 3H), 1.47 (t, J=6.8 Hz, 3H).

Example 22: Compound 30: (S)—N-(5-(1-(3-ethoxy-4-methoxyphenyl)-2-(methylsulfonyl) ethyl)-6-oxo-5,6-dihydro-4H-thieno[2,3-c]pyrrol-3-yl)-2,2,2-trifluoroacetamide

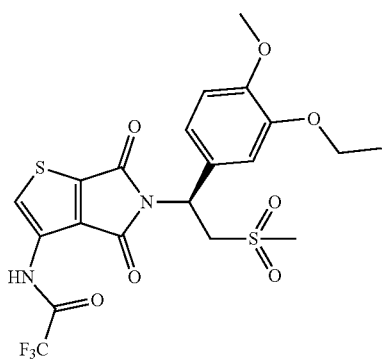 [SMILES: CCOc1cc([C@@H](CS(C)(=O)=O)N2C(=O)c3scc(NC(=O)C(F)(F)F)c3C2=O)ccc1OC]

To a stirred solution of methyl 4-bromo-3-(bromomethyl)thiophene-2-carboxylate (628 mg, 2 mmol) and (S)-1-(3-ethoxy-4-methoxyphenyl)-2-(methylsulfonyl)ethanamine (819 mg, 3.0 mmol) in ACN (20 mL) was added CsCO₃ (358 mg, 1.1 mmol). The mixture was stirred at RT overnight then concentrated and purified on silica gel (PE/EA, 1:1) to give (S)-methyl-4-bromo-3-(((1-(3-ethoxy-4-methoxyphenyl)-2-(methylsulfonyl)ethyl)amino)methyl)thiophene-2-carboxylate (905 mg, 90%) as yellow solid. MS (ESI) m/z 505.9 [M+H]⁺.

To a stirred solution of (S)-methyl4-bromo-3-(((1-(3-ethoxy-4-methoxyphenyl)-2-(methylsulfonyl)ethyl)amino)methyl)thiophene-2-carboxylate (740 mg, 1.46 mmol) in THF (8 mL) and MeOH (8 mL) was added a solution of lithium hydroxide (614 mg, 14.6 mmol) in water (8 mL). The mixture was stirred at RT for 8 h then concentrated. The pH was adjusted to 4 with 2 N HCl and the mixture extracted with DCM. The organic layer was washed with brine, dried over Na₂SO₄, and evaporated to give (S)-4-bromo-3-(((1-(3-ethoxy-4-methoxyphenyl)-2-(methylsulfonyl)ethyl)amino)methyl)thiophene-2-carboxylic acid (638 mg, 89%) as a yellow solid. MS (ESI) m/z 491.9 [M+H]⁺.

To a stirred solution of (S)-4-bromo-3-(((1-(3-ethoxy-4-methoxyphenyl)-2-(methylsulfonyl)ethyl)amino)methyl)thiophene-2-carboxylic acid (628 mg, 1.27 mmol) in DCM (20 mL) was added oxalyl chloride (486 mg, 3.8 mmol) dropwise then 2 drops of DMF was added. The mixture was stirred at RT overnight then concentrated and purified on silica gel (DCM/MeOH, 10:1) to give (S)-3-bromo-5-(1-(3-ethoxy-4-methoxyphenyl)-2-(methylsulfonyl)ethyl)-4H-thieno[2,3-c]pyrrol-6(5H)-one (398 mg, 66%) as a white solid. MS (ESI) m/z 473.9 [M+H]⁺.

To a stirred solution of (S)-3-bromo-5-(1-(3-ethoxy-4-methoxyphenyl)-2-(methylsulfonyl)ethyl)-4H-thieno[2,3-c]pyrrol-6(5H)-one (364 mg, 0.77 mmol) and diphenylmethanimine (183 mg, 1.01 mmol) in 1,4-dioxane (3.5 mL) and toluene (3.5 mL) was added CsCO₃ (511 mg, 1.56 mmol) and tris(dibenzylideneacetone)dipalladium Pd₂(dba)₃ (73 mg, 0.08 mmol) and Xantphos (110 mg, 0.21 mmol). The mixture was stirred at 108° C. (microwave) for 16 h. The mixture was diluted with water and EA. The organic layer was separated and washed with brine, dried by Na₂SO₄, filtered, evaporated, and purified by prep-TLC (Petroleum/EA, 1:1) to give (S)-3-((diphenylmethylene)amino)-5-(1-(3-ethoxy-4-methoxyphenyl)-2-(methylsulfonyl)ethyl)-4H-thieno[2,3-c]pyrrol-6(5H)-one (140 mg, 32%) as a yellow solid. MS (ESI) m/z 575.0 [M+H]⁺.

To a stirred solution of (S)-3-((diphenylmethylene)amino)-5-(1-(3-ethoxy-4-methoxyphenyl)-2-(methylsulfonyl)ethyl)-4H-thieno[2,3-c]pyrrol-6(5H)-one (140 mg, 0.24 mmol) in EA (5 mL) was added a solution of HCl in EA (2.5 mL). The mixture was stirred at RT for 20 min then concentrated and washed with petroleum to give (S)-3-amino-5-(1-(3-ethoxy-4-methoxyphenyl)-2-(methylsulfonyl)ethyl)-4H-thieno[2,3-c]pyrrol-6(5H)-one (130 mg crude) as a yellow solid. MS (ESI) m/z 411.0 [M+H]⁺.

To a stirred solution of (S)-3-amino-5-(1-(3-ethoxy-4-methoxyphenyl)-2-(methylsulfonyl)ethyl)-4H-thieno[2,3-c]pyrrol-6(5H)-one (25 mg, 0.06 mmol) in DCM (1 mL) and pyridine (1 mL) was added a solution of trifluoroacetylchloride (38 mg, 0.18 mmol) in DCM (0.1 mL) at 0° C. The mixture was stirred at 0° C. for 30 min then quenched with water and extracted with EA. The organic layer was washed with 1 N HCl then brine, and dried over Na₂SO₄, evaporated, and purified by prep-TLC (petroleum/EA, 1:1) to give the title compound (4 mg, 33%) as a white solid. MS (ESI) m/z 507.0 [M+H]⁺. ¹H NMR (400 MHz, DMSO-d6) δ 7.92 (s, 1H), 6.99-6.92 (m, 3H), 5.82-5.78 (m, 1H), 4.54 (d, J=19.2 Hz, 1H), 4.27-4.21 (m, 1H), 4.13-4.08 (m, 1H), 4.05-3.98 (m, 2H), 3.96-3.91 (m, 1H), 3.74 (s, 3H), 3.01 (s, 3H), 1.74-1.72 (m, 1H), 1.31 (t, J=6.8 Hz, 3H).

Example 23: Compound 31: (S)—N-(5-(1-(3-ethoxy-4-methoxyphenyl)-2-(methylsulfonyl) ethyl)-6-oxo-5,6-dihydro-4H-thieno[2,3-c]pyrrol-3-yl)-2-methoxyacetamide

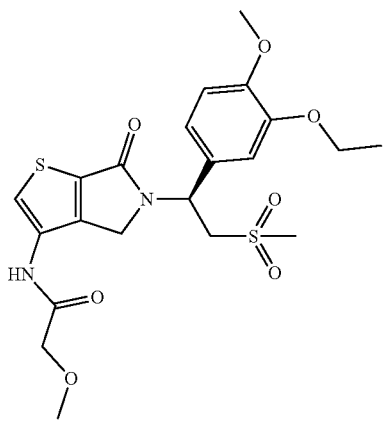 [SMILES: CCOc1cc([C@@H](CS(C)(=O)=O)N2Cc3c(NC(=O)COC)csc3C2=O)ccc1OC]

To a stirred solution of (S)-3-amino-5-(1-(3-ethoxy-4-methoxyphenyl)-2-(methylsulfonyl)ethyl)-4H-thieno[2,3-c]pyrrol-6(5H)-one (30 mg, 0.073 mmol) in DCM (1 mL) and pyridine (1 mL) was added a solution of 2-methoxyacetyl chloride (24 mg, 0.22 mmol) in DCM (0.1 mL) at 0° C. The mixture was stirred at 0° C. for 20 min then quenched with water and extracted with EA. The organic layer was washed with 1 N HCl, then brine, and dried by Na$_2$SO$_4$, evaporated, and purified by prep-TLC (petroleum/EA, 1:2) to give the title compound (18 mg, 57%) as a white solid. MS (ESI) m/z 483.1 [M+H]$^+$. $^1$H NMR (400 MHz, DMSO-d6) δ 10.24 (s, 1H), 7.77 (s, 1H), 6.98-6.91 (m, 3H), 5.81-5.77 (m, 1H), 4.49 (d, J=18.4 Hz, 1H), 4.24-4.18 (m, 1H), 4.12-4.08 (m, 1H), 4.05-3.92 (m, 5H), 3.74 (s, 3H), 3.35 (s, 3H), 3.00 (s, 3H), 1.31 (t, J=6.8 Hz, 3H).

Example 24: Compound 32: (S)—N-(5-(1-(3-ethoxy-4-methoxyphenyl)-2-(methylsulfonyl) ethyl)-6-oxo-5,6-dihydro-4H-thieno[2,3-c]pyrrol-3-yl)cyclopropanecarboxamide

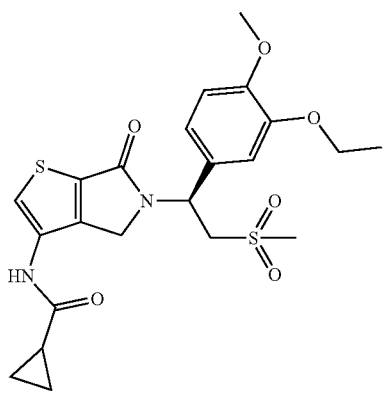 [SMILES: CCOc1cc([C@@H](CS(C)(=O)=O)N2Cc3c(NC(=O)C4CC4)csc3C2=O)ccc1OC]

To a stirred solution of (S)-3-amino-5-(1-(3-ethoxy-4-methoxyphenyl)-2-(methylsulfonyl)ethyl)-4H-thieno[2,3-c]pyrrol-6(5H)-one (40 mg, 0.098 mmol) in DCM (1 mL) and pyridine (1 mL) was added a solution of cyclopropanecarbonyl chloride (0.35 mmol) in DCM (0.2 mL) at 0° C. The mixture was stirred at 0° C. for 30 min then quenched with water and extracted with EA. The organic layer was washed with 1 N HCl then brine, and dried over Na$_2$SO$_4$, evaporated, and purified by prep-TLC (petroleum/EA, 1:2) to give (S)—N-(5-(1-(3-ethoxy-4-methoxyphenyl)-2-(methylsulfonyl)ethyl)-6-oxo-5,6-dihydro-4H-thieno[2,3-c]pyrrol-3-yl) cyclopropanecarboxamide (7 mg, 22%) as a white solid. MS (ESI) m/z 479.1 [M+H]$^+$. $^1$H NMR (400 MHz, DMSO-d6) δ 10.55 (s, 1H), 7.73 (s, 1H), 6.98-6.91 (m, 3H), 5.79-5.76 (m, 1H), 4.74 (d, J=18.8 Hz, 1H), 4.21-4.14 (m, 1H), 4.06-3.93 (m, 4H), 3.74 (s, 3H), 3.00 (s, 3H), 1.74-1.72 (m, 1H), 1.34-1.31 (m, 3H), 0.85-0.78 (m, 4H).

Cell-Based TNFα Inhibition Assay

PBMCs induced with LPS (lipopolysaccharide): Frozen primary blood mononuclear cells (PBMCs) are purchased from AllCells. Cells are quick thawed, washed once with Roswell Park Memorial Institute medium (RPMI)-1640/10% FBS/1% Penicillin/1% Streptomycin and plated in 96 well plates at 200,000 cells per well. Cells are pretreated with DMSO only or the indicated compounds for 1 hr and then induced with 100 ng/mL for 18-24 hrs. The supernatant is analyzed for TNF-α using Meso Scale assay according to manufacturer's protocol. The negative control wells are treated with DMSO. Compound activity is measured as a percentage of the DMSO control.

CHART 1

| | TNFα Inhibition | |
|---|---|---|
| Compound No. | % TNFα Inhibition (0.1 μM) | % TNFα Inhibition (1 μM) |
| 1 | B | A |
| 2 | D | A |
| 3 | B | A |
| 4 | D | B |
| 5 | C | A |
| 6 | B | A |
| 7 | D | D |
| 8 | D | A |
| 9 | D | B |
| 10 | D | B |
| 11 | D | C |
| 12 | D | D |
| 13 | D | D |
| 14 | D | D |
| 15 | D | D |
| 16 | D | D |
| 17 | D | D |
| 18 | D | D |
| 19 | D | D |
| 20 | D | D |
| 21 | D | D |
| 22 | C | C |
| 23 | C | B |
| 24 | D | D |
| 25 | D | C |
| 26 | D | D |
| 27 | D | D |
| 28 | D | D |
| 29 | D | D |
| 30 | D | D |
| 31 | D | D |
| 32 | D | C |

For TNFα inhibition assay: A = a single percent inhibition value ≥60%; B = a single percent inhibition value <60% and >40%; C = a single percent inhibition value ≤40% and >20%; and D = a single percent inhibition value ≤20%.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

It will be further understood by those within the art that if a specific number of an introduced claim recitation is intended, such an intent will be explicitly recited in the claim, and in the absence of such recitation no such intent is present.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A compound of Formula (I), or a pharmaceutically acceptable salt thereof,

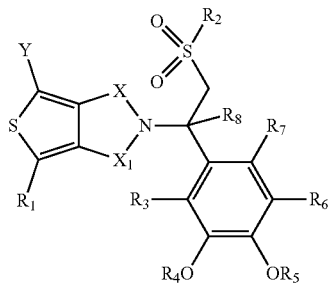

(I)

wherein:
Y is H, deuterium, halogen, or an optionally substituted $C_1$-$C_6$ alkyl;
X and $X_1$ are each independently $CH_2$, C=O, SO, $SO_2$, or $CH_2CO$;
$R_1$ is deuterium, hydroxy, halogen, cyano, optionally substituted $C_1$-$C_6$ alkoxy, —$NHR_{1A}$, —$NR_{1A}R_{1B}$, —$NHC(O)R_{1C}$, —$NR_{1A}C(O)R_{1C}$, —$NHSO_2R_{1C}$, —$NR_{1A}SO_2R_{1C}$, —$N[C(O)R_{1A}][C(O)R_{1C}]$, —$NHC(O)CH_2OCH_3$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
$R_{1A}$ and $R_{1B}$ are independently an optionally substituted $C_3$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
$R_{1C}$ is $CF_3$, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
$R_2$ is hydroxy, —$NH_2$, —$NHR_{1A'}$, —$NR_{1A'}R_{1B'}$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
$R_{1A}'$ and $R_{1B}'$ are independently an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
$R_3$, $R_6$, and $R_7$ are independently selected from the group consisting of a hydrogen, a deuterium, a halogen, an optionally substituted $C_1$-$C_6$ alkyl, an optionally substituted $C_1$-$C_6$ alkoxy, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl;
$R_4$ and $R_5$ are independently selected from the group consisting of an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, and an optionally substituted 5 to 10 membered heteroaryl; or
$R_4$ and $R_5$, together with the atoms to which they are attached, form an optionally substituted 5 or 6 membered heterocyclyl; and
$R_8$ is hydrogen or deuterium.

2. The compound of claim 1,
wherein:
$R_1$ is deuterium, hydroxy, halogen, cyano, optionally substituted $C_1$-$C_6$ alkoxy, —$NHR_{1A}$, —$NR_{1A}R_{1B}$, —$NHC(O)R_{1C}$, —$NR_{1A}C(O)R_{1C}$, —$NHSO_2R_{1C}$, —$NR_{1A}SO_2R_{1C}$, an optionally substituted $C_1$-$C_6$ alkyl, an optionally substituted $C_3$-$C_6$ cycloalkyl, an optionally substituted 3 to 10 membered heterocyclyl, an optionally substituted $C_6$-$C_{10}$ aryl, or an optionally substituted 5 to 10 membered heteroaryl;
wherein, when a $C_1$-$C_6$ alkyl, a $C_1$-$C_6$ alkoxy, a $C_3$-$C_6$ cycloalkyl, a $C_6$-$C_{10}$ aryl, a 3 to 10 membered heterocyclyl, or a 5 to 10 membered heteroaryl is substituted, the substituted substituents are independently selected from the group consisting of a deuterium, an oxo, a halogen, cyano, a nitro, an optionally substituted $C_1$-$C_6$ alkyl, an optionally substituted $C_1$-$C_6$ haloalkyl, an optionally substituted $C_1$-$C_6$ alkoxy, an optionally substituted $C_3$-$C_6$ cycloalkyl, an optionally substituted $C_6$-$C_{10}$ aryl, an optionally substituted 3 to 10 membered heterocyclyl, an optionally substituted 5 to 10 membered heteroaryl, $C(O)R_A$, $C(O)OR_A$, —$C(O)NR_BR_C$, —$OR_A$, —$OC(O)R_A$, —$OC(O)NR_BR_C$, —$OS(O)R_A$, —$OS(O)_2R_A$, —$OS(O)NR_BR_C$, —$OS(O)_2NR_BR_C$, —$NR_BR_C$, —$NR_AC(O)R_A$, —$NR_AC(O)OR_A$, —$NR_AC(O)NR_BR_C$, —$NR_AS(O)R_A$, —$NR_AS(O)_2R_A$, —$NR_AS(O)NR_BR_C$, —$NR_AS(O)_2NR_BR_C$, —$SR_A$, —$S(O)R_A$, —$S(O)_2R_A$, —$S(O)NR_BR_C$, and —$S(O)_2NR_BR_C$; and each $R_A$, $R_B$, and $R_C$ is independently selected from the group consisting of a hydrogen, a deuterium, an unsubstituted $C_1$-$C_6$ alkyl, an unsubstituted $C_2$-$C_6$ alkenyl, an unsubstituted $C_3$-$C_6$ cycloalkyl, an unsubstituted 3 to 10 membered heterocyclyl, an unsubstituted $C_6$-$C_{10}$ aryl, and an unsubstituted 5 to 10 membered heteroaryl; or $R_B$ and $R_C$, together with the nitrogen atom to which they are attached, form an optionally substituted 3 to 10 membered heterocyclyl.

3. The compound of claim 1, wherein one of X and $X_1$ is $CH_2$ and the other is C=O.

4. The compound of claim 1, wherein X is C=O and $X_1$ is $CH_2$.

5. The compound of claim 1, wherein X and $X_1$ are each C=O.

6. The compound of claim 1, wherein $R_1$ is —$NHR_{1A}$, —$NR_{1A}R_{1B}$, —$NHC(O)R_{1C}$, —$N[C(O)R_{1A}][C(O)R_{1C}]$, or —$NR_{1A}C(O)R_{1C}$.

7. The compound of claim 6, wherein $R_1$ is —NHC(O)$R_{1C}$.

8. The compound of claim 1, wherein $R_{1A}$ and $R_{1B}$ are independently an optionally substituted $C_3$-$C_6$ alkyl or an optionally substituted $C_3$-$C_6$ cycloalkyl, and wherein $R_{1C}$ is an optionally substituted $C_3$-$C_6$ cycloalkyl.

9. The compound of claim 1, wherein $R_3$, $R_6$, and $R_7$ are independently selected from the group consisting of a hydrogen, a halogen, and an optionally substituted $C_1$-$C_6$ alkyl.

10. The compound of claim 9, wherein $R_3$, $R_6$, and $R_7$ are each hydrogen.

11. The compound of claim 1, wherein $R_2$ is an optionally substituted $C_1$-$C_6$ alkyl.

12. The compound of claim 1, wherein $R_2$ is an unsubstituted $C_1$-$C_6$ alkyl.

13. The compound of claim 1, wherein $R_4$ and $R_5$, together with the atoms to which they are attached, form an optionally substituted 5 or 6 membered heterocyclyl.

14. The compound of claim 1, wherein $R_8$ is hydrogen.

15. A compound selected from the group consisting of:

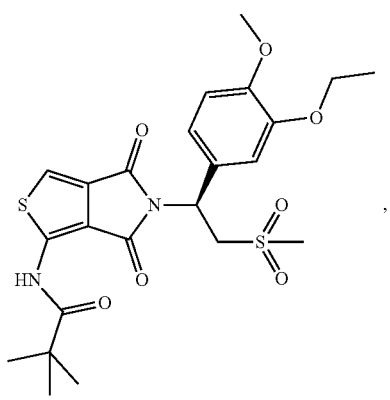

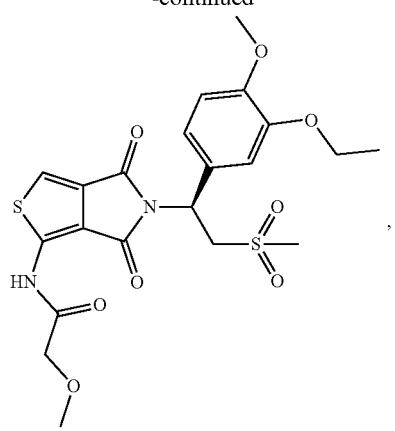

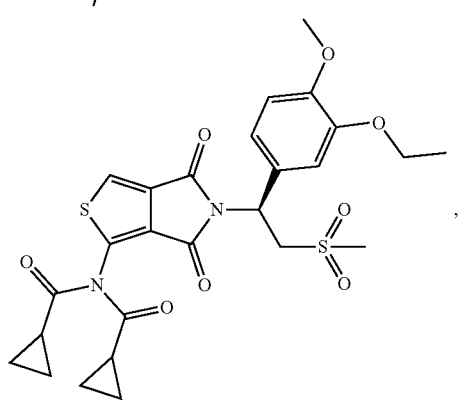

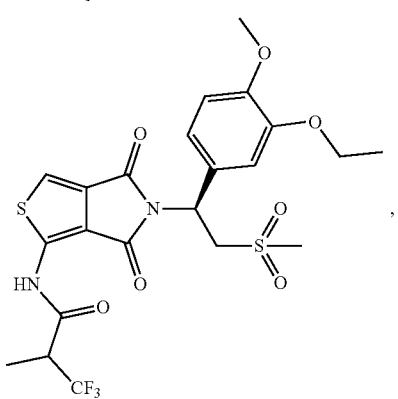

-continued

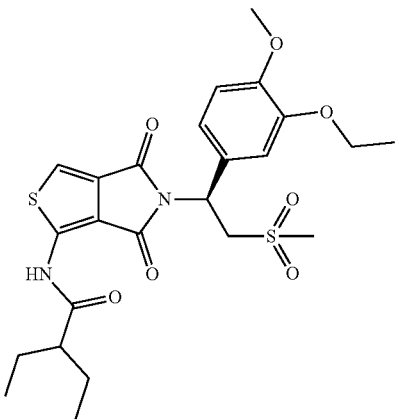

87
-continued
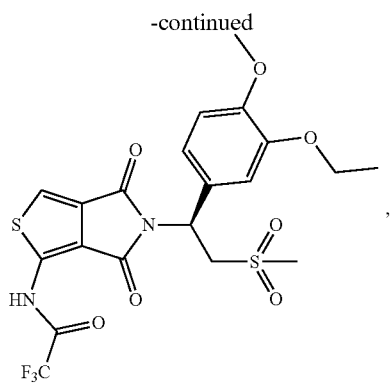
,
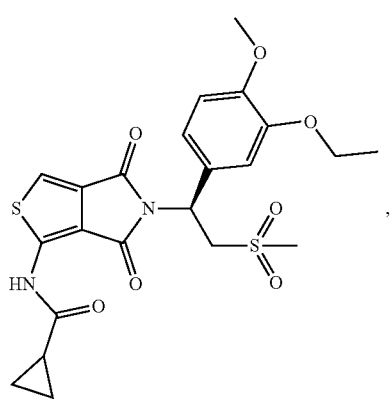
,
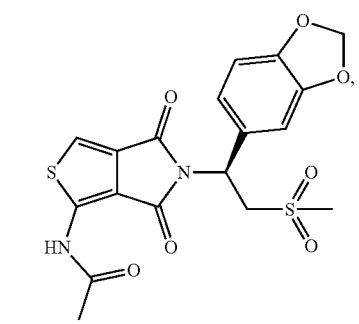 [SMILES: CC(=O)Nc1scc2c1C(=O)N([C@H](CS(C)(=O)=O)c1ccc3c(c1)OCO3)C2=O]
,
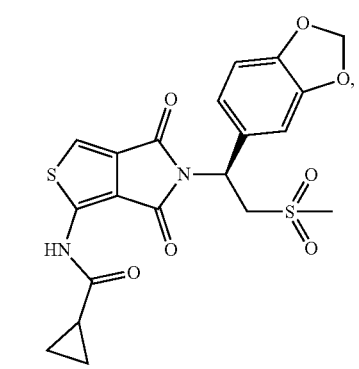
,
88
-continued
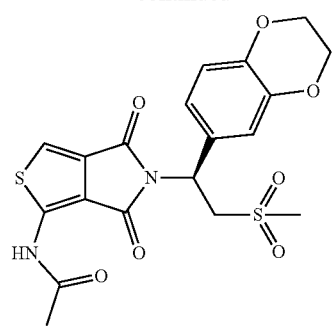
,
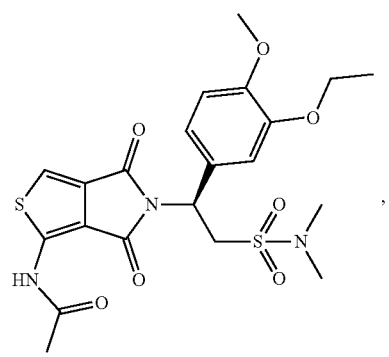
,
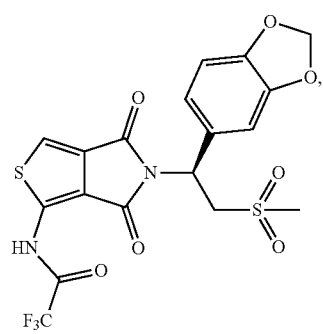
,
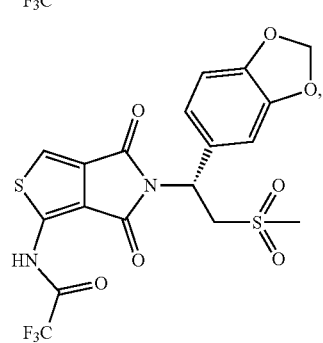
,
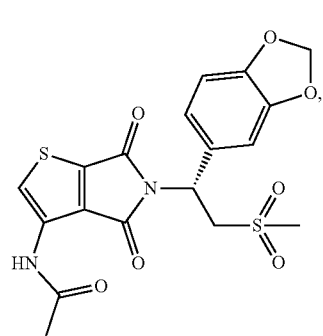

-continued

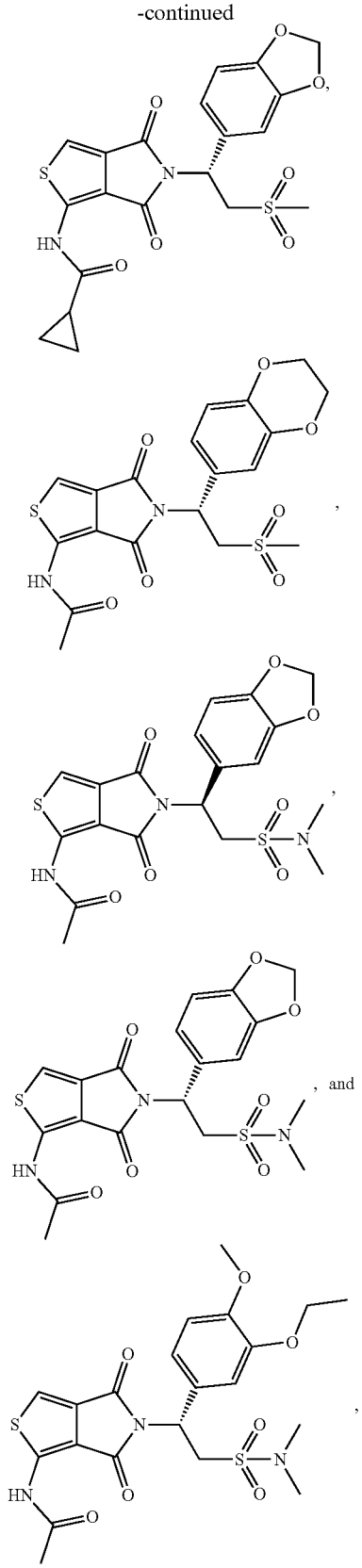

or a pharmaceutically acceptable salt thereof.

16. A pharmaceutical composition comprising a compound of claim 1, or a pharmaceutically acceptable salt thereof, and at least one pharmaceutically acceptable carrier.

17. A method of treating, or ameliorating a disease, disorder, or condition associated with TNF-α, INF-γ, IL-2, IL-17, or IL-23, or a combination thereof, to a subject in need thereof, comprising administering a therapeutically effective amount of a compound of claim 1, or a pharmaceutically acceptable salt thereof, to the said subject; wherein the disease, disorder, or condition is selected from the group consisting of arthritis, ankylosing spondylitis, osteoarthritis, rheumatoid arthritis, Behcet's disease, an inflammatory bowel disease, psoriasis, psoriatic arthritis, atopic dermatitis, and contact dermatitis, or combinations thereof.

18. A method of treating, or ameliorating a disease, disorder, or condition associated with PDE4, to a subject in need thereof, comprising administering a therapeutically effective amount of a compound of claim 1, or a pharmaceutically acceptable salt thereof, to the said subject; wherein the disease, disorder, or condition is selected from the group consisting of arthritis, ankylosing spondylitis, osteoarthritis, rheumatoid arthritis, Behcet's disease, an inflammatory bowel disease, psoriasis, psoriatic arthritis, atopic dermatitis, and contact dermatitis, or combinations thereof.

19. A method of decreasing expression of a protein selected from TNF-α, INF-γ, IL-2, IL-17, IL-23, or a combination thereof, comprising contacting a cell with a compound of claim 1, or a pharmaceutically acceptable salt thereof.

20. The method of claim 19, wherein the protein is TNF-α.

21. A method of inhibiting PDE4 activity, comprising contacting a cell with a compound of claim 1, or a pharmaceutically acceptable salt thereof.

22. A method of treating psoriasis to a subject in need thereof, comprising topically administering a therapeutically effective amount of a pharmaceutical composition of claim 16, to the said subject.

23. The compound of claim 5, wherein $R_1$ is —$NHR_{1A}$, —$NR_{1A}R_{1B}$, —$NHC(O)R_{1C}$, —$N[C(O)R_{1A}][C(O)R_{1C}]$, or —$NR_{1A}C(O)R_{1C}$.

24. The compound of claim 23, wherein $R_{1A}$ and $R_{1B}$ are independently an optionally substituted $C_3$-$C_6$ alkyl or an optionally substituted $C_3$-$C_6$ cycloalkyl, and wherein $R_{1C}$ is $CF_3$ or an optionally substituted $C_3$-$C_6$ cycloalkyl.

25. The compound of claim 24, wherein $R^2$ is an optionally substituted $C_1$-$C_6$ alkyl, —$NH(C_{1-6}$ alkyl), or —$N(C_{1-6}$ alkyl)$_2$.

26. The compound of claim 25, wherein $R_3$, $R_6$, and $R_7$ are independently a hydrogen, a halogen, or an optionally substituted $C_1$-$C_6$ alkyl.

27. The compound of claim 26, wherein $R_4$ and $R_5$ are independently an optionally substituted $C_1$-$C_6$ alkyl.

28. The compound of claim 26, wherein $R_4$ and $R_5$, together with the atoms to which they are attached, form an optionally substituted 5 or 6 membered heterocyclyl.

29. The compound of claim 1, wherein $R_{1C}$ is —$CF_3$ or an optionally substituted $C_3$-$C_6$ cycloalkyl.

30. The compound of claim 7, wherein $R_{1C}$ is an optionally substituted $C_3$-$C_6$ cycloalkyl.

* * * * *

UNITED STATES PATENT AND TRADEMARK OFFICE
CERTIFICATE OF CORRECTION

PATENT NO. : 10,570,147 B2  
APPLICATION NO. : 16/000108  
DATED : February 25, 2020  
INVENTOR(S) : Robert Sullivan et al.

Page 1 of 4

It is certified that error appears in the above-identified patent and that said Letters Patent is hereby corrected as shown below:

In the Specification

In Column 9, Lines 1-13 (approx.), delete

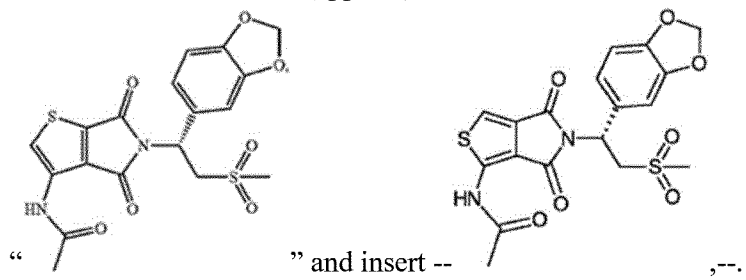

" and insert --                    ,--.

In Column 11, Lines 30-46 (approx.), delete

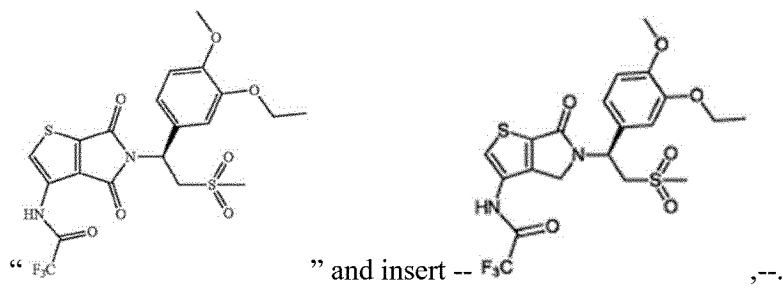

" and insert --                    ,--.

Signed and Sealed this  
Second Day of June, 2020

Andrei Iancu  
*Director of the United States Patent and Trademark Office*

In Column 11, Lines 48-67 (approx.), delete

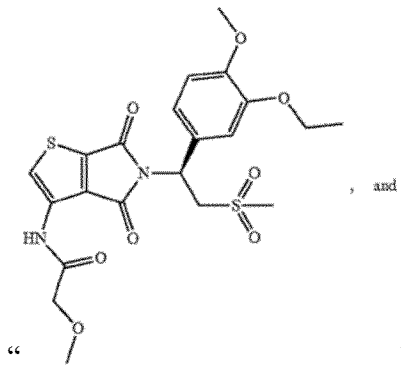 " and insert -- 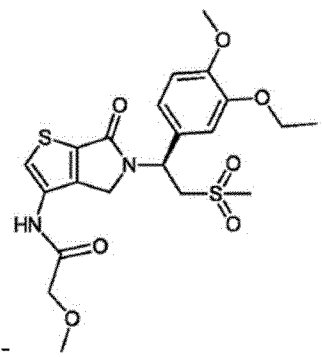 , and--.

In Column 12, Lines 1-15 (approx.), delete

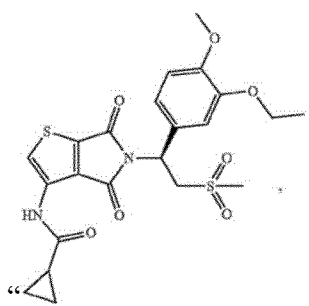 " and insert -- 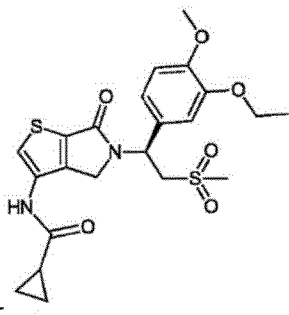 ,--.

In Column 17, Line 13, delete "diazidiridine," and insert --diaziridine,--.

In Column 18, Lines 39-40, delete "heteroalicyclylic" and insert --heteroalicyclic--.

In Column 18, Line 44, delete "tetrahydro" and insert --(tetrahydro--.

In Column 22, Line 4, delete "p-toluensulfonic" and insert --p-toluenesulfonic--.

In Column 32, Line 13, delete "sec-buty," and insert --sec-butyl,--.

In Column 32, Line 43, delete "sec-buty," and insert --sec-butyl,--.

In Column 33, Line 1, delete "sec-buty," and insert --sec-butyl,--.

In Column 38, Line 10, delete "sec-buty," and insert --sec-butyl,--.

In Column 38, Line 40, delete "sec-buty," and insert --sec-butyl,--.

In Column 38, Line 65, delete "sec-buty," and insert --sec-butyl,--.

In Column 42, Line 41, delete "sec-buty," and insert --sec-butyl,--.

CERTIFICATE OF CORRECTION (continued)
U.S. Pat. No. 10,570,147 B2

In Column 42, Line 66, delete "sec-buty," and insert --sec-butyl,--.

In Column 43, Line 24, delete "sec-buty," and insert --sec-butyl,--.

In Column 43, Line 55, delete "sec-buty," and insert --sec-butyl,--.

In Column 44, Line 13, delete "sec-buty," and insert --sec-butyl,--.

In Column 44, Line 21, delete "sec-buty," and insert --sec-butyl,--.

In Column 44, Line 43, delete "sec-buty," and insert --sec-butyl,--.

In Column 45, Line 8, delete "sec-buty," and insert --sec-butyl,--.

In Column 48, Line 8, delete "sec-buty," and insert --sec-butyl,--.

In Column 48, Line 33, delete "sec-buty," and insert --sec-butyl,--.

In Column 48, Line 58, delete "sec-buty," and insert --sec-butyl,--.

In Column 49, Line 22, delete "sec-buty," and insert --sec-butyl,--.

In Column 49, Line 48, delete "sec-buty," and insert --sec-butyl,--.

In Column 49, Line 52, delete "sec-buty," and insert --sec-butyl,--.

In Column 50, Line 10, delete "sec-buty," and insert --sec-butyl,--.

In Column 50, Line 42, delete "sec-buty," and insert --sec-butyl,--.

In Column 52, Line 61, delete "74%, 74%, 75%," and insert --74%, 75%, 76%,--.

In Column 53, Line 61, delete "mytomycin;" and insert --mitomycin;--.

In Column 54, Line 12, delete "ytarabine;" and insert --cytarabine;--.

In Column 54, Line 33, delete "vorinosta;" and insert --vorinostat;--.

In Column 54, Line 56, delete "zolimoma;" and insert --zolimomab;--.

In Column 62, Line 1, delete "S)" and insert --(S)--.

In Column 63, Lines 15-16, delete "carbonyldiimidazol" and insert --carbonyldiimidazole--.

In Column 69, Lines 63-64, delete "Carbonyldiimidazol" and insert --carbonyldiimidazole--.

In Column 71, Line 32, delete "Carbonyldiimidazol" and insert --carbonyldiimidazole--.

In Column 74, Line 20 (approx.), delete "carbonyldiimidazol" and insert --carbonyldiimidazole--.

In Column 78, Line 5 (approx.), delete "carbonyldiimidazol" and insert --carbonyldiimidazole--.

In Column 79, Lines 31-46 (approx.), delete

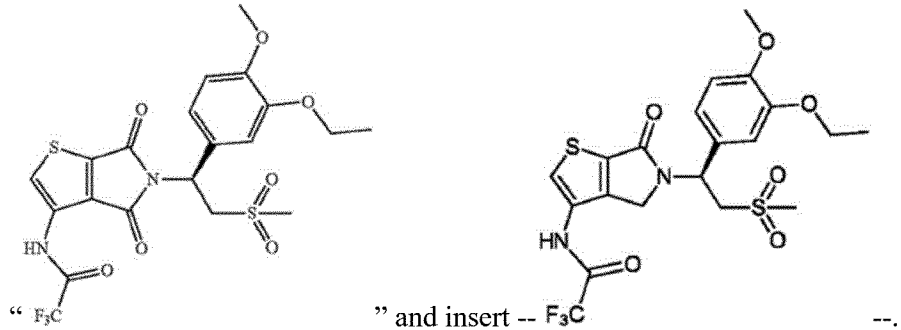

" and insert -- -- .

In the Claims

In Column 84, Line 20 (approx.), Claim 1, delete "is CF$_3$," and insert --is —CF$_3$,--.

In Column 85, Line 3, Claim 2, delete "heteroaryl, C(O)R$_A$, C(O)OR$_A$," and insert --heteroaryl, —C(O)R$_A$, —C(O)OR$_A$,--.

In Column 88, Lines 54-67 (approx.), Claim 15, delete

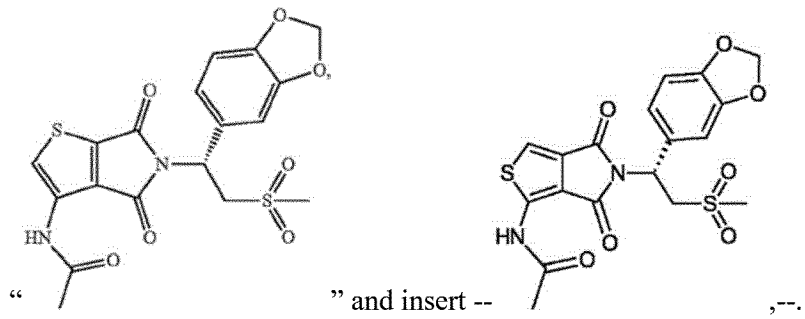

" and insert -- ,--.

In Column 90, Lines 48-49, Claim 24, delete "is CF$_3$" and insert --is —CF$_3$--.

In Column 90, Line 50, Claim 25, delete "wherein R$^2$ is" and insert --wherein R$_2$ is--.